US011617660B2

(12) United States Patent
Alden

(10) Patent No.: US 11,617,660 B2
(45) Date of Patent: Apr. 4, 2023

(54) FEMORAL COMPONENT EXTRACTOR

(71) Applicant: Dana Andrew Alden, Osprey, FL (US)

(72) Inventor: Dana Andrew Alden, Osprey, FL (US)

(73) Assignee: Tri-Sphere Holdings, LLC, Osprey, FL (US)

( * ) Notice: Subject to any disclaimer, the term of this patent is extended or adjusted under 35 U.S.C. 154(b) by 173 days.

(21) Appl. No.: 16/900,612

(22) Filed: Jun. 12, 2020

(65) Prior Publication Data

US 2021/0386558 A1 Dec. 16, 2021

(51) Int. Cl.
*A61F 2/46* (2006.01)

(52) U.S. Cl.
CPC .... *A61F 2/4607* (2013.01); *A61F 2002/4619* (2013.01); *A61F 2002/4629* (2013.01)

(58) Field of Classification Search
CPC ........... A61B 17/921; A61F 2002/4619; A61F 2002/4628; A61F 2/4607; A61F 2002/4681; B25B 27/02; B25B 27/023; B25B 27/062; Y10T 24/44291; F16B 2/10; F16B 2/065
See application file for complete search history.

(56) References Cited

U.S. PATENT DOCUMENTS

| 4,222,382 | A | * | 9/1980 | Antonsson | ............ | A61F 2/4607 606/100 |
| 4,601,289 | A | * | 7/1986 | Chiarizzio | ......... | A61B 17/1659 606/85 |
| 4,993,410 | A | * | 2/1991 | Kimsey | ................. | A61F 2/4607 606/100 |
| 5,064,427 | A | * | 11/1991 | Burkinshaw | .......... | A61F 2/4612 606/99 |
| 5,514,136 | A | * | 5/1996 | Richelsoph | ........... | A61F 2/4607 606/86 R |
| 5,534,006 | A | * | 7/1996 | Szabo | .................... | A61F 2/4607 606/100 |
| 5,735,857 | A | * | 4/1998 | Lane | ..................... | A61F 2/4607 81/418 |

(Continued)

FOREIGN PATENT DOCUMENTS

| EP | 3799841 A1 * | 4/2021 | ............. A61B 17/92 |
| WO | WO 2019/169357 A1 | 6/2019 | |

OTHER PUBLICATIONS

Shukla Medical; Shukla Hip Universal Hip Implant Extraction Solution and MOD Shukla Hip Universal Implant Extraction Solution; 2002 (Year: 2002).*

(Continued)

*Primary Examiner* — David W Bates

(57) ABSTRACT

Briefly, the invention herein is an extractor for clamping and extracting the femoral component from a patient's femur, comprising a body, a lever, a fulcrum, and a strike plate, wherein:
(a) defined within the body is an opening for the lever and a threaded surface that cooperates with a threaded fastener to lock the extractor on the femoral component;
(b) the lever extends through the lever opening and includes a clamping surface and a locking surface;
(c) the locking surface cooperates with the threaded surface of the body to lock the lever in place;
(d) the fulcrum comprises a stainless steel pin extending through the body and the lever; and
(e) the strike plate is configured to receive the blows of a mallet.

25 Claims, 35 Drawing Sheets

(56) References Cited

U.S. PATENT DOCUMENTS

| | | | | |
|---|---|---|---|---|
| 5,743,910 | A * | 4/1998 | Bays | A61F 2/4607 606/99 |
| 5,951,564 | A * | 9/1999 | Schroder | A61F 2/4607 606/100 |
| 7,022,141 | B2 * | 4/2006 | Dwyer | A61F 2/4657 623/22.12 |
| 8,690,880 | B2 * | 4/2014 | Bastian | A61B 17/164 606/85 |
| 9,089,440 | B2 * | 7/2015 | Mueller | A61F 2/461 |
| 9,526,512 | B2 * | 12/2016 | Sharp | A61B 17/164 |
| 10,987,231 | B2 * | 4/2021 | Sweitzer | A61F 2/461 |
| 2008/0033444 | A1 * | 2/2008 | Bastian | A61B 17/1668 606/85 |
| 2008/0172061 | A1 * | 7/2008 | Ragbir | A61F 2/4603 606/208 |
| 2008/0262503 | A1 * | 10/2008 | Muller | A61F 2/4612 606/99 |
| 2014/0207123 | A1 * | 7/2014 | Mueller | A61F 2/4607 606/1 |
| 2018/0028249 | A1 * | 2/2018 | Jaumard | A61F 2/4601 |
| 2019/0336307 | A1 * | 11/2019 | Sungu | A61B 17/8872 |

OTHER PUBLICATIONS

Stryker; Rejuvenate Total Hip System Surgical Protocol; 2011 (Year: 2011).*
International Search Report for PCT/US2020/000029 (Year: 2020).*
Innomed; Innovations in Orthopedic Instruments (Year: 2016).*
Lafosse, J. M.; Removal of well-fixed femoral stems; Elsevier (Year: 2015).*
DePuy extractor manufactured and sold before the filing date of U.S. Appl. No. 16/900,492. Photographs attached.

* cited by examiner

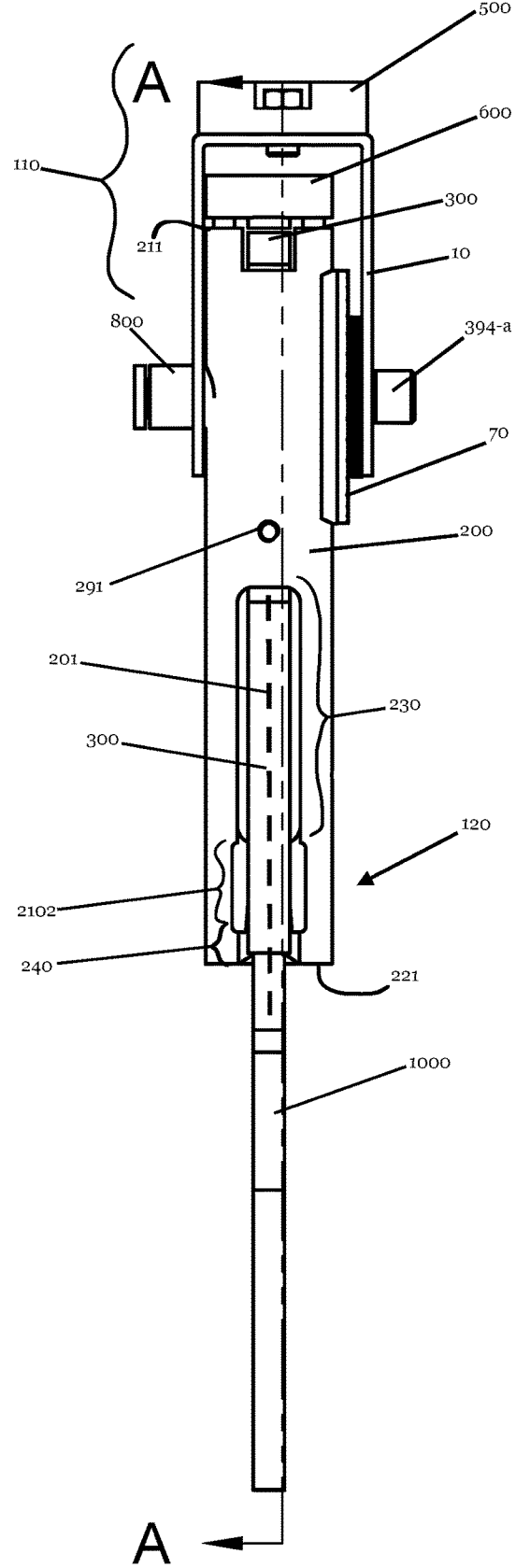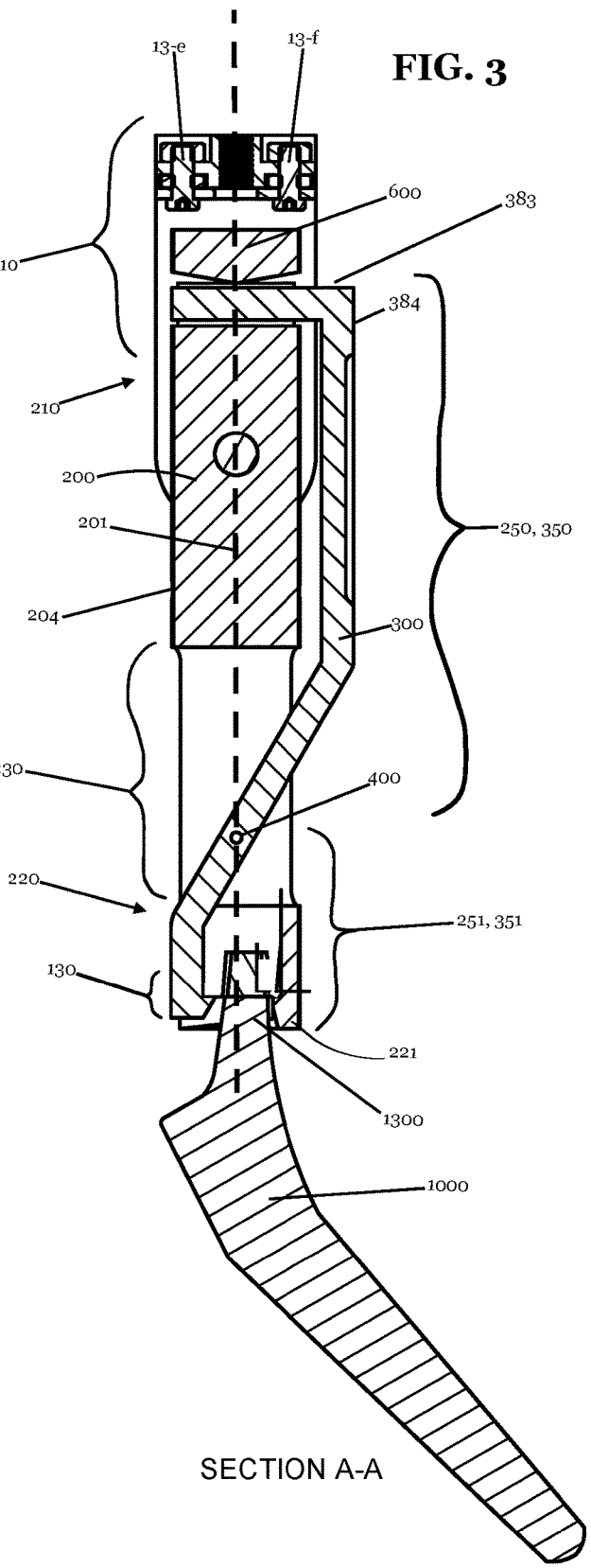

SECTION A-A

SECTION A-A

DETAIL B

SECTION A-A

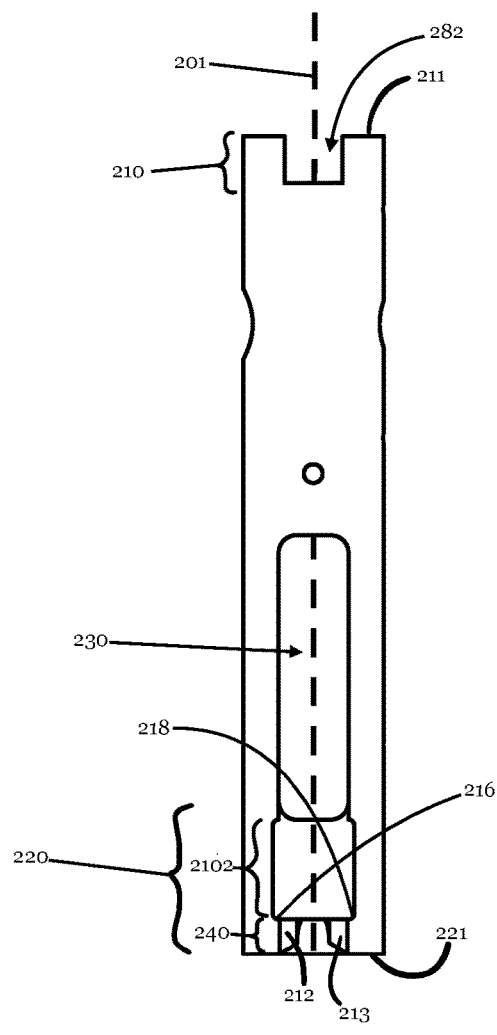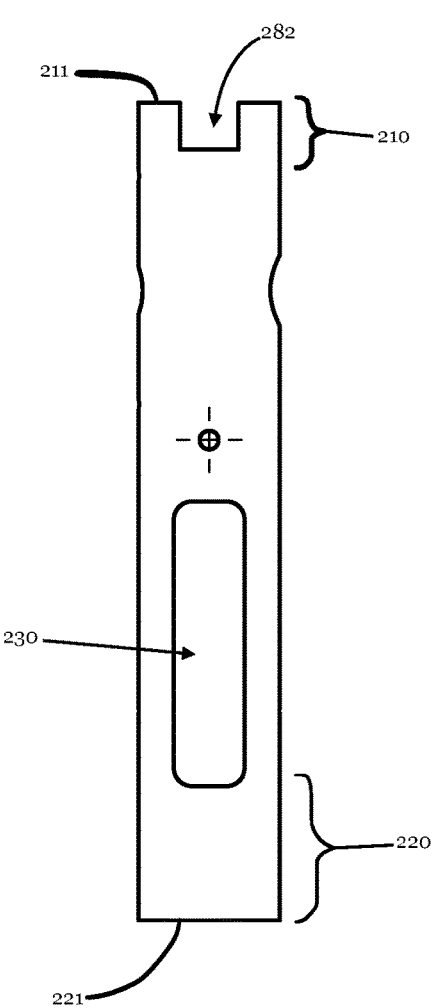
FIG. 14
FIG. 15

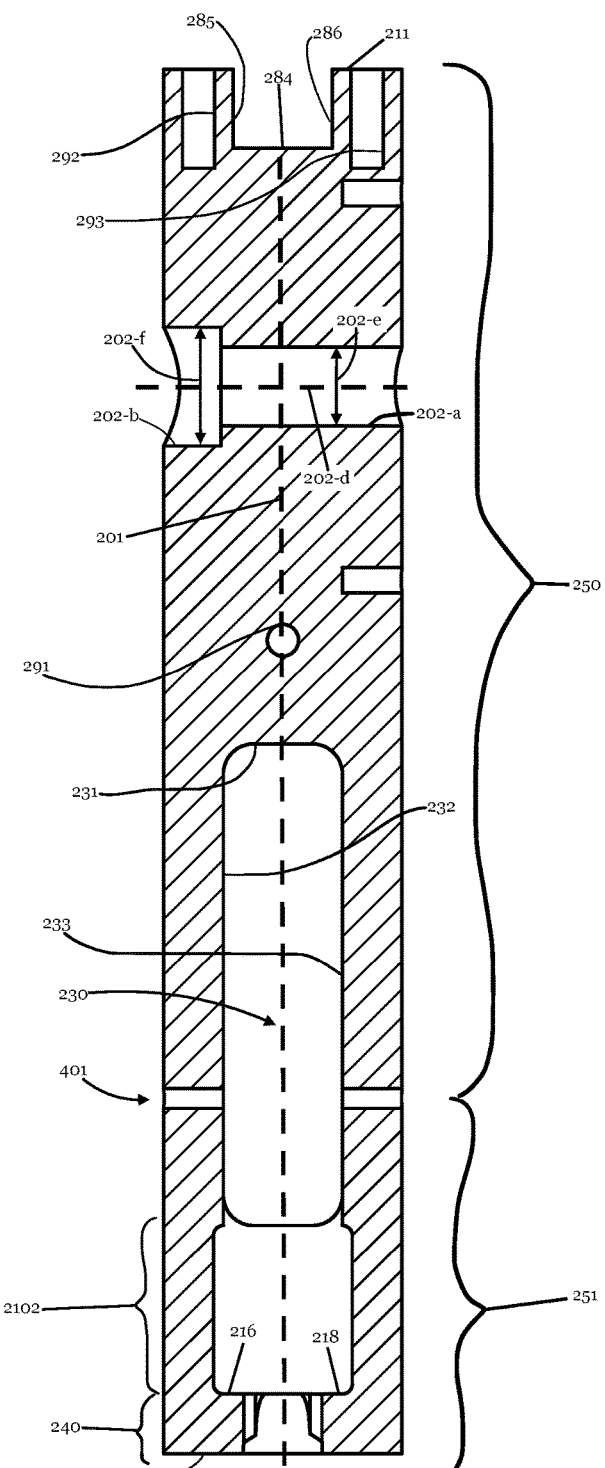
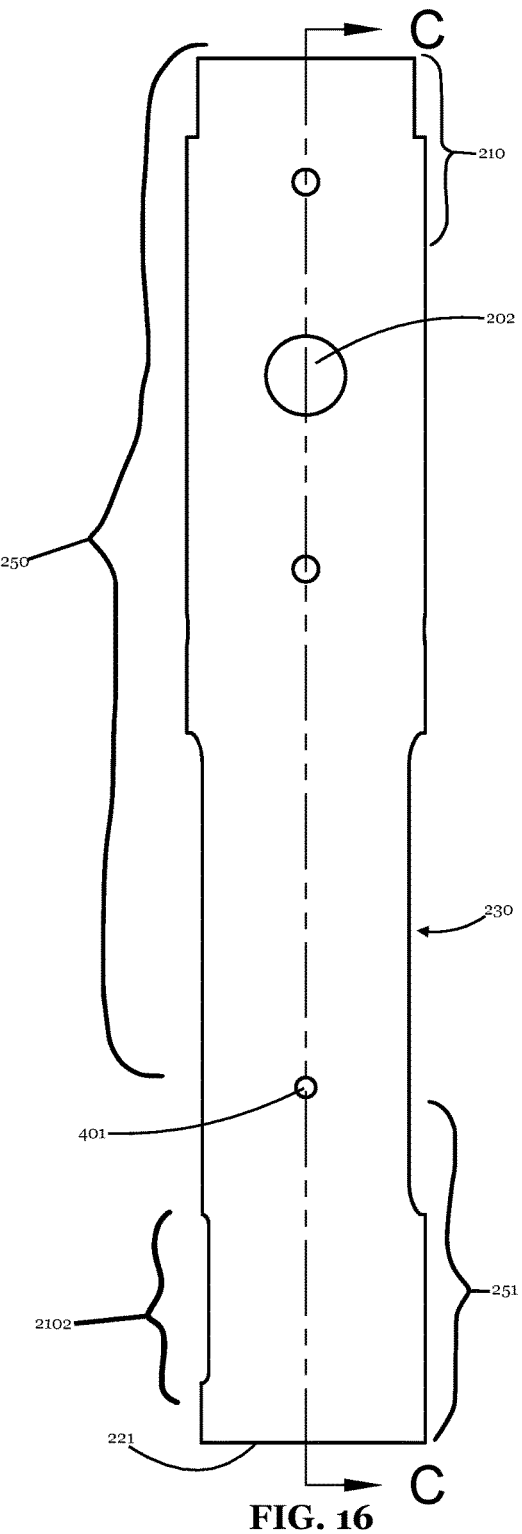
FIG. 17
SECTION C-C
FIG. 16

FIG. 18
FIG. 19
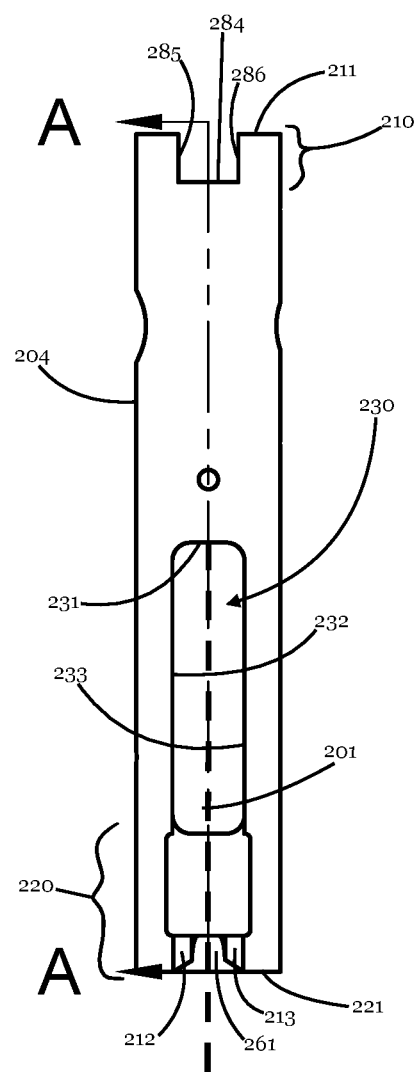
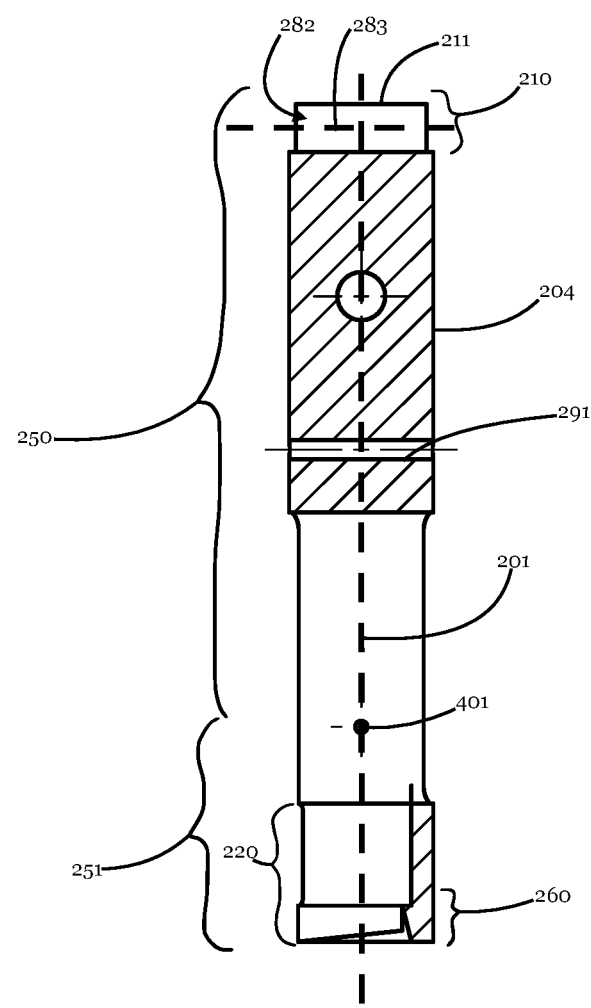
SECTION A-A

SECTION B-B

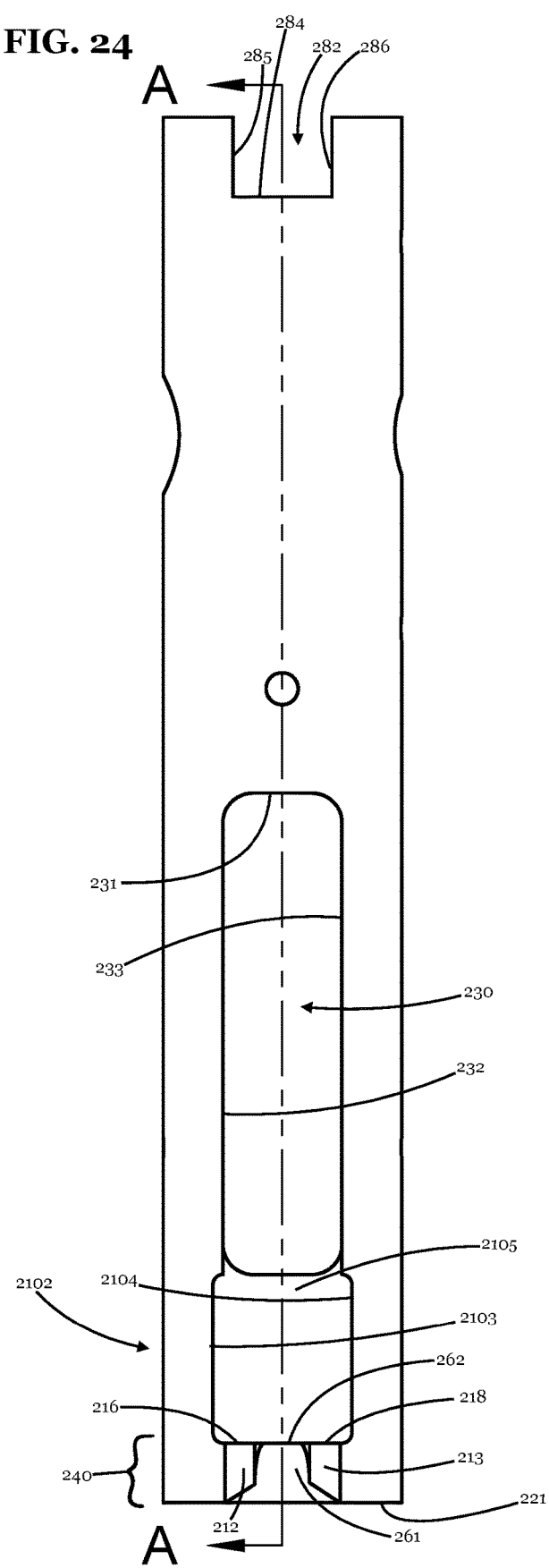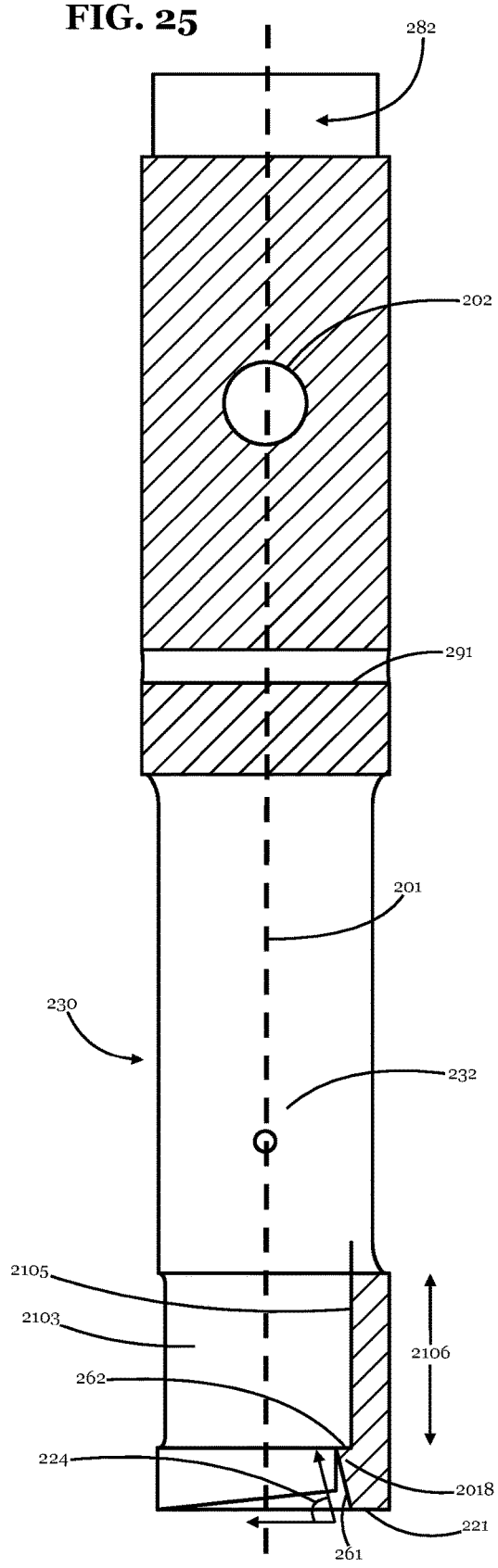

DETAIL A

FIG. 29
FIG. 30
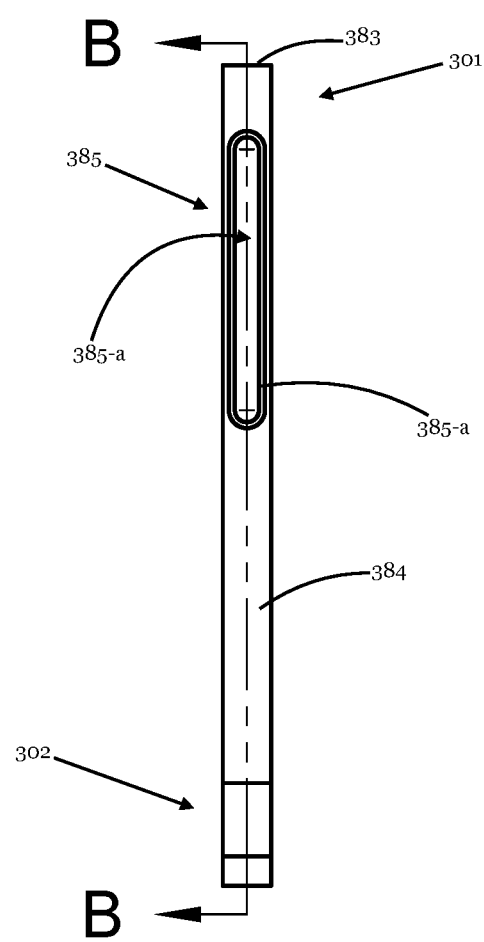
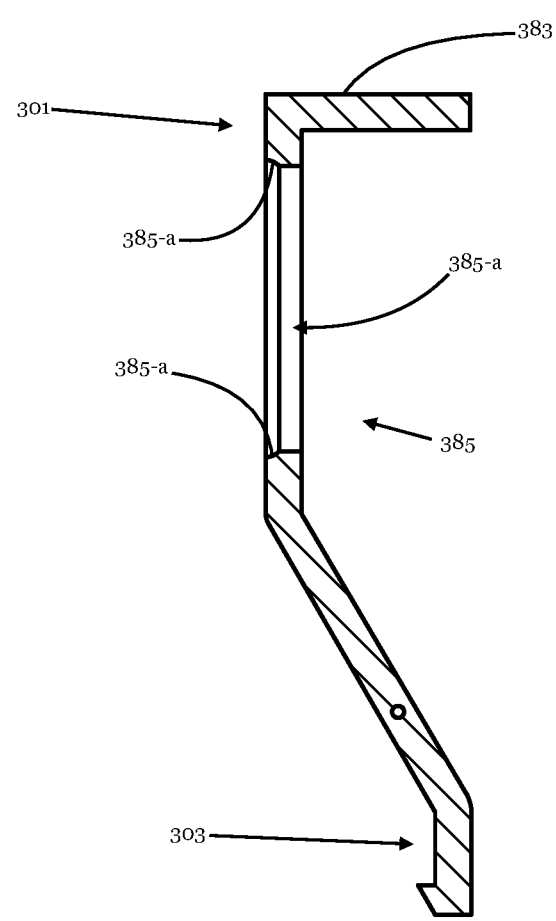
SECTION B-B

SECTION A-A

SECTION B-B

SECTION A-A

SECTION A-A

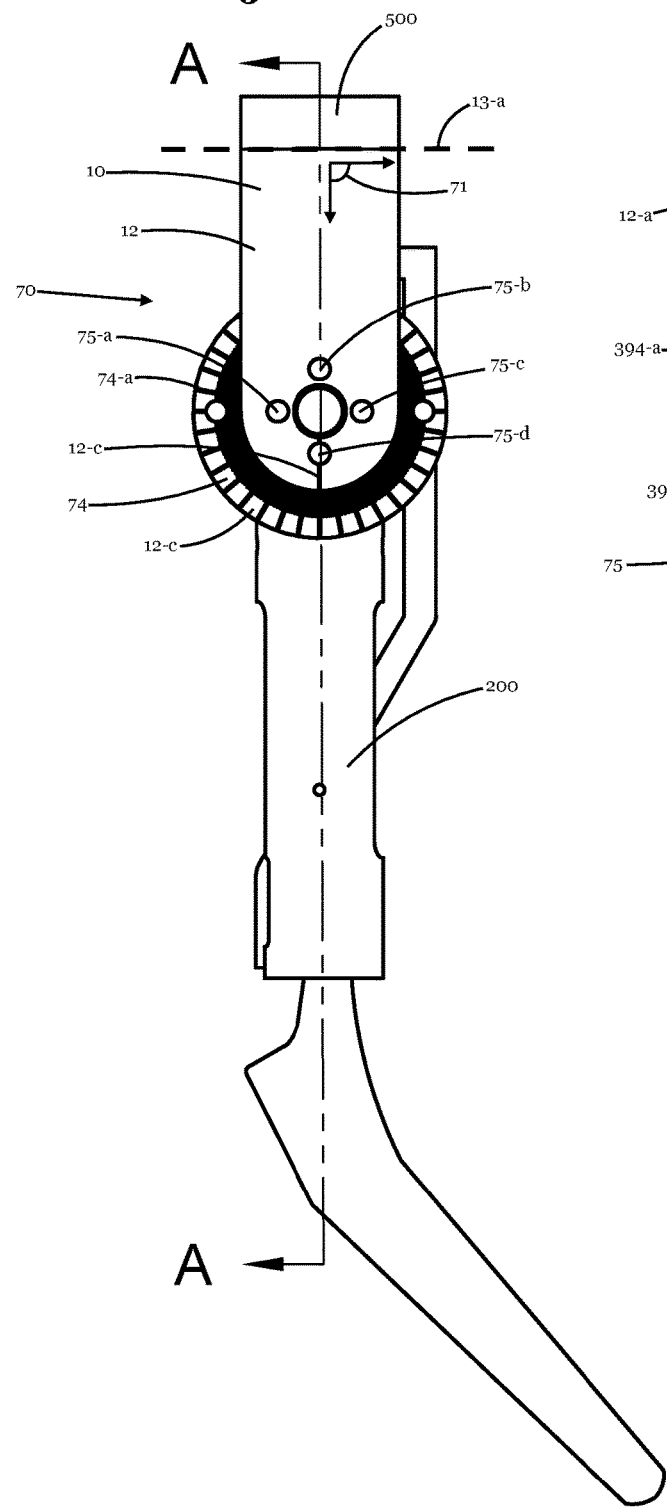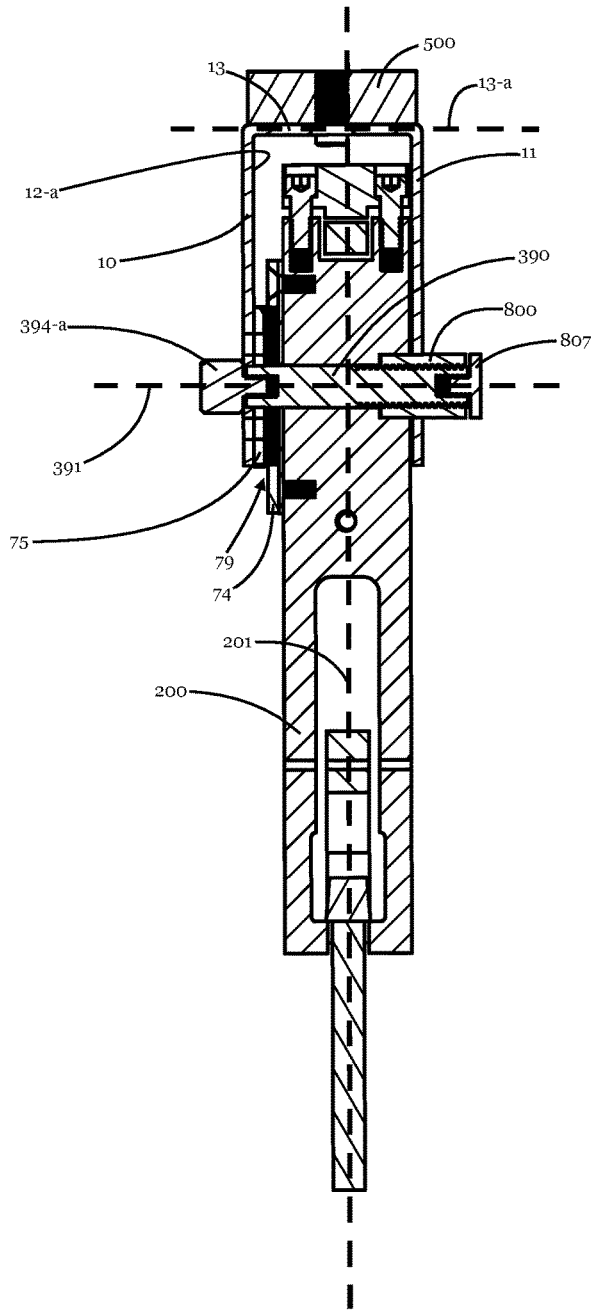
FIG. 50
FIG. 51
SECTION A-A

SECTION A-A

DETAIL A 394-a

FEMORAL COMPONENT EXTRACTOR

FIELD OF THE INVENTION

This patent application relates to surgical instruments used to extract the femoral component of an artificial hip.

BACKGROUND OF THE INVENTION

It has been known in orthopedic surgical practices to implant artificial hips. Such prosthetic devices include a femoral component and an acetabular component, which together function as a ball and socket joint. The femoral component is often fabricated from metallic biomaterials with a surface finish that is highly polished. The smooth surfaces of the femoral component inhibit corrosion and bacterial growth. FIG. 67 of the drawings provided herein depicts such a femoral component, and, as shown, the femoral component includes a stem provided with an axis and a spherically-shaped head that extends from the axis of the stem at an irregular angle (i.e. an angle that is not 90 degrees).

The stem is shaped to be inserted axially into a patient's femur. Naturally, before the femoral component can be implanted, the patient's existing femoral head must be removed and the femur prepared to receive the prosthesis. The surgeon accomplishes this by broaching a cavity within the femoral canal that is shaped according to the stem. Often, surgeons undersize the cavity and impact the femoral component into the femur so that the prosthesis is firmly secured without any voids where bacteria and other infection causing agents can grow. Alternatively, surgeons fill the cavity with a type of cement and then fix the stem of the femoral component within the cement.

Unfortunately, artificial implants loosen, components corrode and break, bio-compatibility degrades, and infections develop. Thus, patients with artificial hips sometimes require hip revision surgery. In such a procedure, the prosthetic implants must be removed, including the femoral component. However, as noted above, the femoral component is often well-fixed within the patient's femur. As noted above, the irregular geometric configuration combined with the polished surfaces render vice-grip instruments largely ineffective as they slip on the femoral component's smooth surfaces.

If the femoral component cannot be extracted, the surgeon must remove the femoral component surgically via an extended trochanteric osteotomy, a procedure that often has complications and extends patient recovery. Thus, there is a need for an extractor that can clamp onto the polished surfaces of the femoral component without slipping. There is also a need for an extractor that can remove a femoral component despite the irregular geometry associated with such prosthetic devices. There is also a need for an extractor that enables a surgeon to remove a well-fixed femoral component from a patient's femur without resorting to additional surgical procedures that have complications of their own and that extend a patient's recovery time.

The foregoing does not purport to be an exhaustive explication of all the disadvantages associated with prior art extractors; however, the present invention is directed to overcoming these (and other) disadvantages inherent in prior art systems. The advantages of the present invention will become readily apparent to those of ordinary skill in the art after reading the disclosure provided herein.

BRIEF DESCRIPTION OF THE DRAWINGS

FIG. 2 depicts a perspective view from one side of the extractor clamping onto a femoral component.

FIG. 3 depicts a cross-sectional view of the extractor in FIG. 2 clamping onto a femoral component.

FIG. 14 depicts a perspective view of the body of the extractor.

FIG. 15 depicts a perspective view of the body of the extractor.

FIG. 16 depicts a perspective view of the body of the extractor.

FIG. 17 depicts a cross-sectional view of the body of the extractor in FIG. 16.

FIG. 18 depicts a perspective view of the body of the extractor.

FIG. 19 depicts a cross-sectional view of the body of the extractor in FIG. 18.

FIG. 24 depicts a perspective view of the body of the extractor.

FIG. 25 depicts a cross-sectional view of the body of the extractor in FIG. 24.

FIG. 29 depicts a perspective view of the lever included in the extractor.

FIG. 30 depicts a cross-sectional view of the lever in FIG. 29.

FIG. 50 depicts a perspective view of the extractor with the bracket configured to rotate while the jaws clamp a femoral component.

FIG. 51 depicts a cross-sectional view of the extractor depicted in FIG. 50.

SUMMARY OF THE INVENTION

The invention is defined by the claims set forth herein; however, briefly, the invention herein is an extractor for clamping and extracting the femoral component from a patient's femur, comprising a body, a lever, a fulcrum, and a strike plate, wherein:

(a) defined within the body is an opening for the lever and a threaded surface that cooperates with a threaded fastener to lock the extractor on the femoral component;

(b) the lever extends through the lever opening and includes a clamping surface and a locking surface;

(c) the locking surface cooperates with the threaded surface of the body to lock the lever in place;

(d) the fulcrum comprises a stainless steel pin extending through the body and the lever; and (e) the strike plate is configured to receive the blows of a mallet.

DETAILED DESCRIPTION OF THE INVENTION

Figure 1:
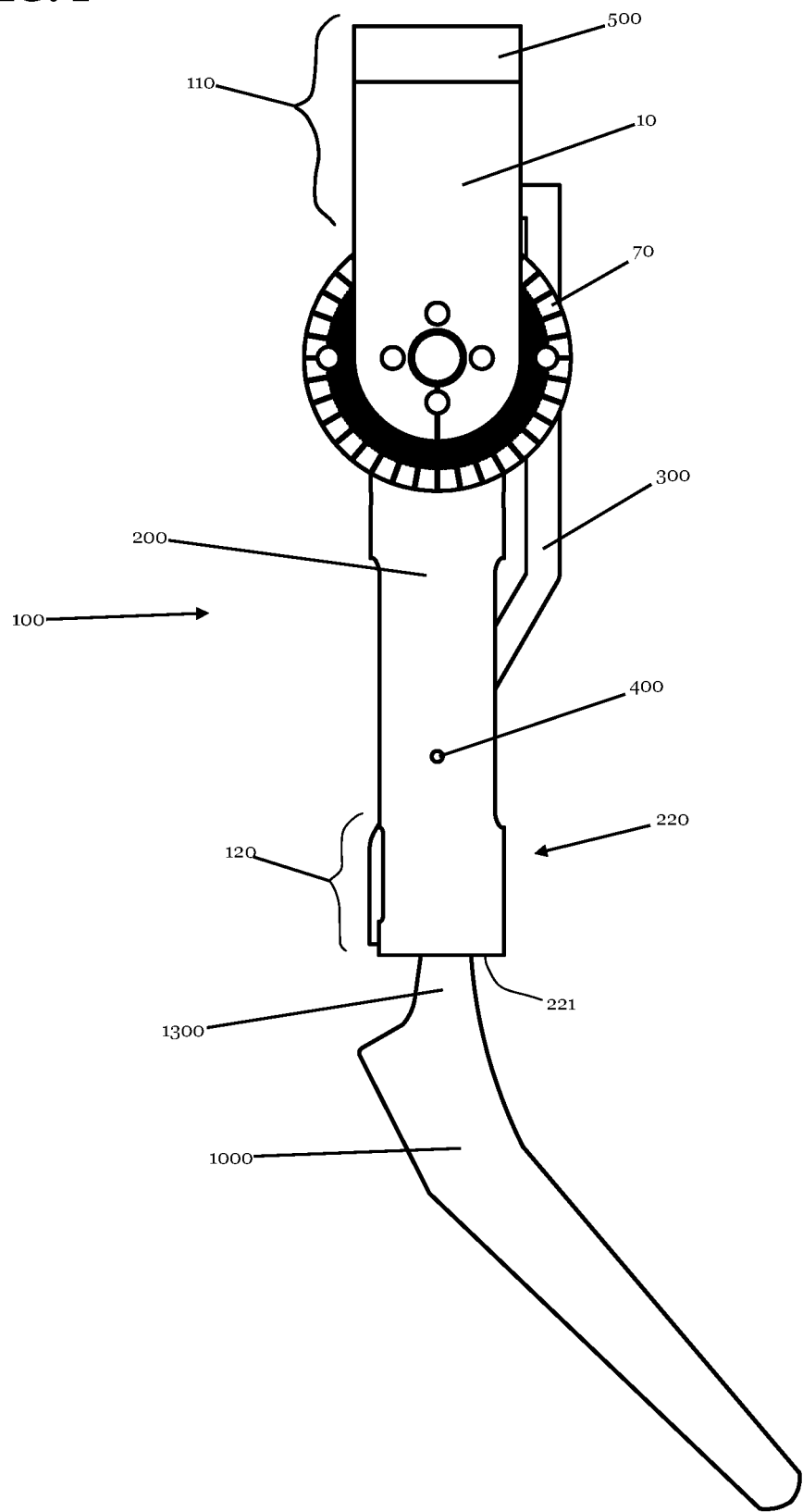
FIG. 1 depicts a perspective view from one side of the extractor clamping onto a femoral component.

FIG. 1 depicts an extractor 100 constituting a presently preferred embodiment of the invention disclosed herein. The extractor 100 is provided with a first end 110 and a second end 120, and, in FIG. 1, is depicted clamping a femoral component 1000. As used herein, the term "end" is defined to include the extreme end, as well as a portion extending from the extreme end. As FIG. 1 also depicts, the extractor 100 is provided with a bracket 10, a locking component 600 (shown in FIGS. 2 and 3), a fulcrum 400, a lever 300, a body 200, and an angle selector 70.

Figure 67:
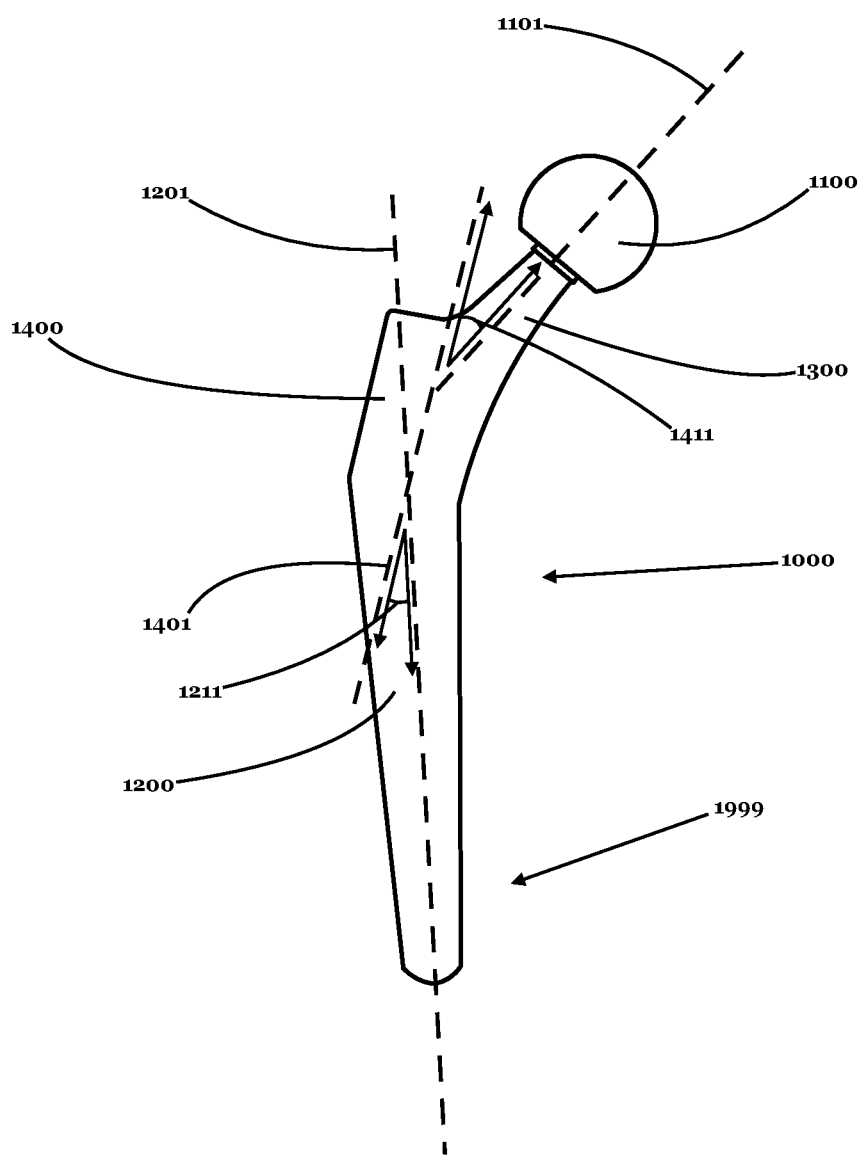
FIG. 67 is a perspective view of the femoral component.
Figure 68:
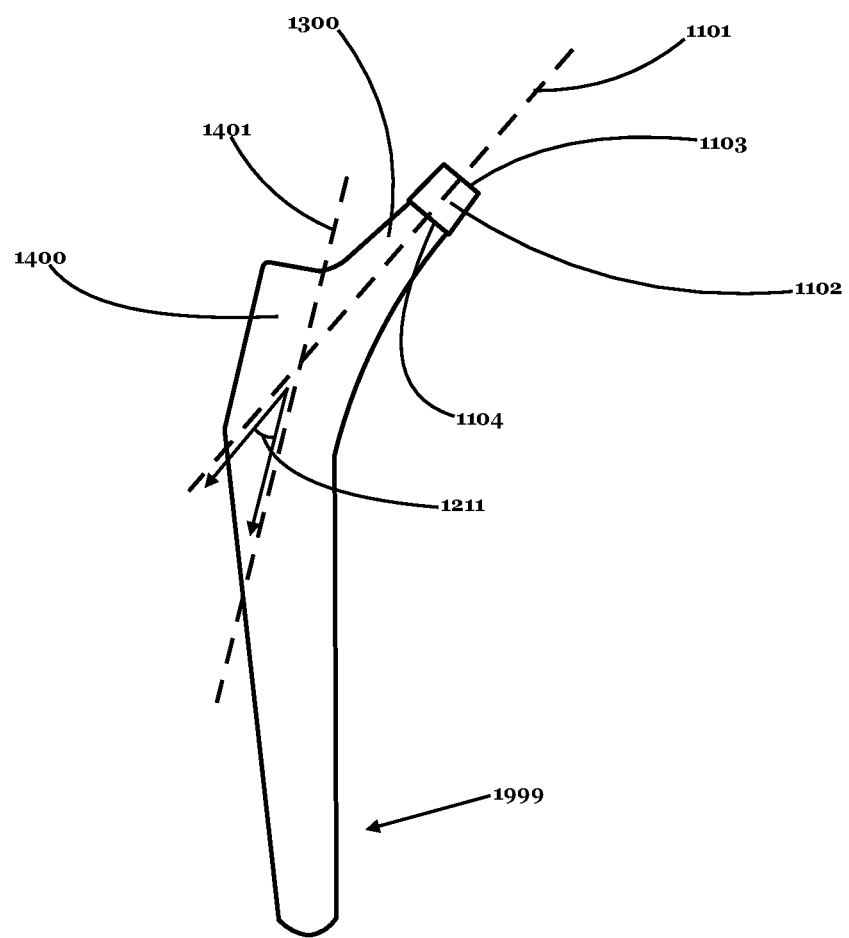
FIG. 68 is a perspective view of the femoral component.
Figure 69:
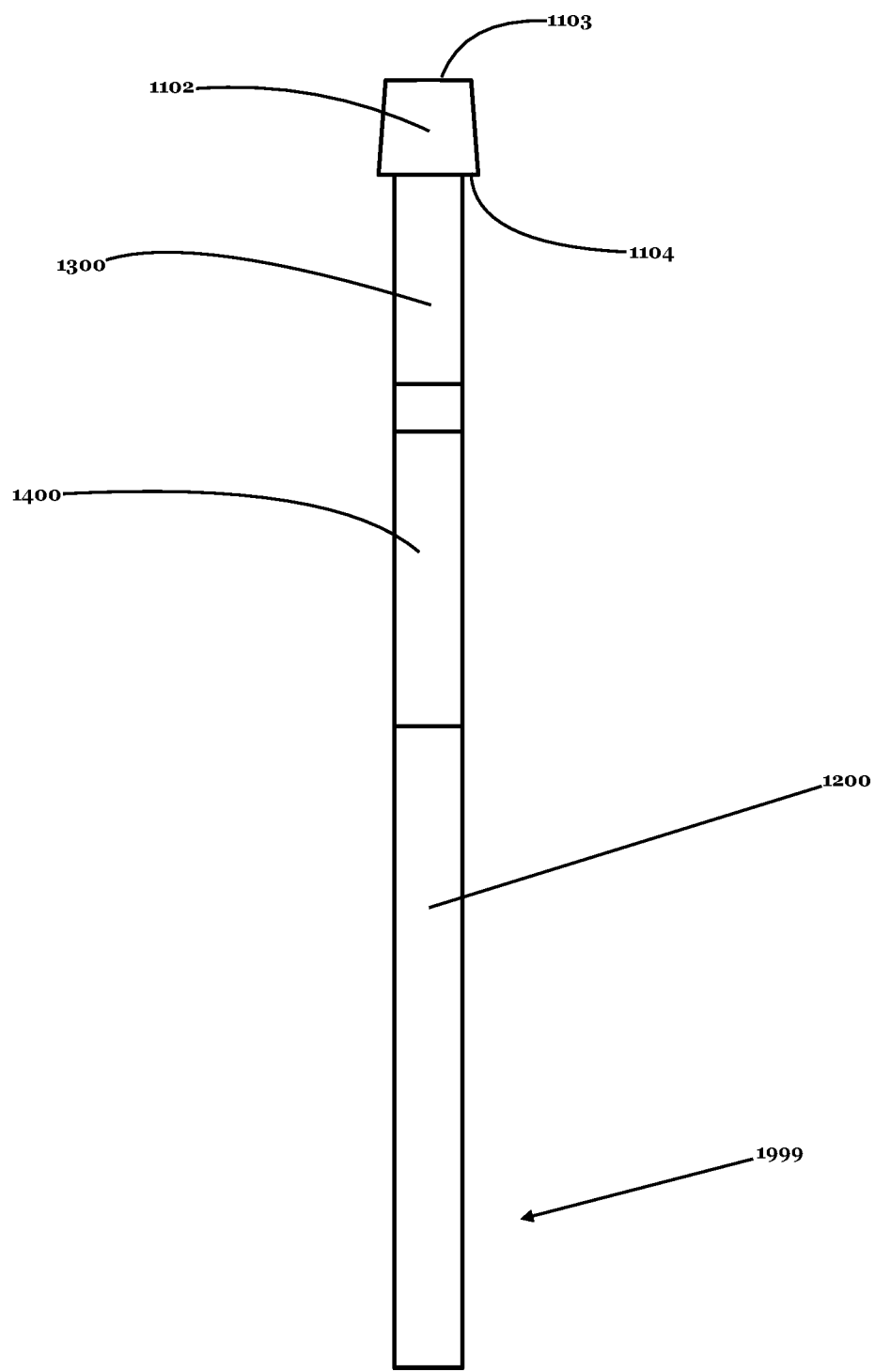
FIG. 69 is a perspective view of the femoral component.

The femoral component referred to above is depicted in FIGS. 67, 68, and 69. As FIG. 67 illustrates, the femoral component 1000 is provided with a head 1100, a trunnion axis 1101, a stem 1200 (which includes a stem axis 1201), and a component end 1999. As FIGS. 67, 68, and 69 further show, the head 1100 (shown in FIG. 67) is disposed on a trunnion 1102 (shown in FIGS. 68 and 69). The trunnion 1102 is generally cylindrical about the trunnion axis 1101 but tapers from the top trunnion surface 1103 to the bottom trunnion surface 1104. The top and bottom surfaces 1103, 1104 are oriented to be generally orthogonal to the trunnion axis 1101.

Extending from the bottom surface 1104 of the trunnion 1102 is a trunnion neck 1300, which is generally co-axial with the axis 1101 of the trunnion 1102 and generally rectangular when cross-sectioned axially. The trunnion neck 1300 of the femoral component 1000 usually tapers to a larger dimension as it blends into an impacted section 1400 (which includes an impacting axis 1401). Extending from the impacted section 1400, the stem 1200 tapers along a stem axis 1201 to the end 1999 of the femoral component 1000.

As FIGS. 67 and 68 illustrate, the stem axis 1201 is oriented at an angle 1211 relative to the trunnion axis 1101, and, in similar fashion, the impacting axis 1401 is also oriented at an angle 1411 relative to the trunnion axis 1101. Though the foregoing angles 1211, 1411 vary with each manufacturer of femoral components, the angles 1211, 1411 provided in each make and model are well known to surgeons practicing joint replacement. The impacting axis 1401 generally defines the direction in which the femoral component 1000 is inserted into a patient's femur, and those of ordinary skill in the art will understand that the femoral component 1000 is often provided with a cylindrical hole that is axially parallel with the impacting axis 1401 for a tool that impacts the femoral component 1000 into patient's femur.

Figure 6:
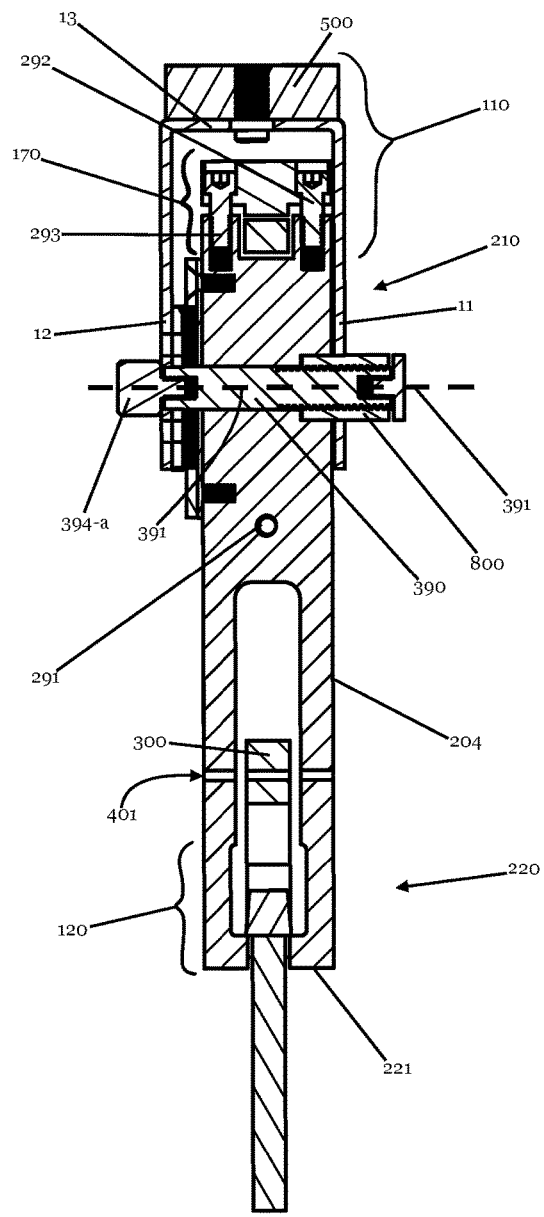
FIG. 6 depicts a cross-sectional view of the extractor in FIG. 7 clamping onto a femoral component.

As noted above, the extractor 100 is provided with a body 200, which is shown in FIGS. 2 and 3. As FIGS. 2 and 3 illustrate, the body 200 is provided with an outer body surface 204 that is generally cylindrical about an axis 201. The body 200 is also provided with a first end 210 and a second end 220 (which are also shown in FIGS. 6. and 7). Each of the ends 210, 220 includes an end surface and a portion of the body extending from the end surface. To distinguish the end surfaces from one another, the end surface located at the first end 210 shall be referred to as the "first" end surface 211, and the end surface located at the second end 220 shall be referred to as the "second" end surface 221. As FIG. 2 illustrates, the cylindrically-shaped body 200 extends axially and terminates at each of the end surfaces 211, 221, and each of the end surfaces 211, 221 extends at least partially in a radial direction from the axis 201 and generally terminates at the outer body surface 204.

Located between the first end surface 211 and the second end surface 221, a wedging structure 240, a trunnion accepting structure 2102, and a lever opening 230 are defined within the body 200. The wedging structure 240 extends axially from the second end surface 221 and is dimensioned so that the neck 1300 of the femoral component 1000 is wedged therewithin. The wedging structure 240 is located axially adjacent to the trunnion accepting structure 2102, which is dimensioned to accommodate the trunnion 1102 of the femoral component 1000.

Figure 4:
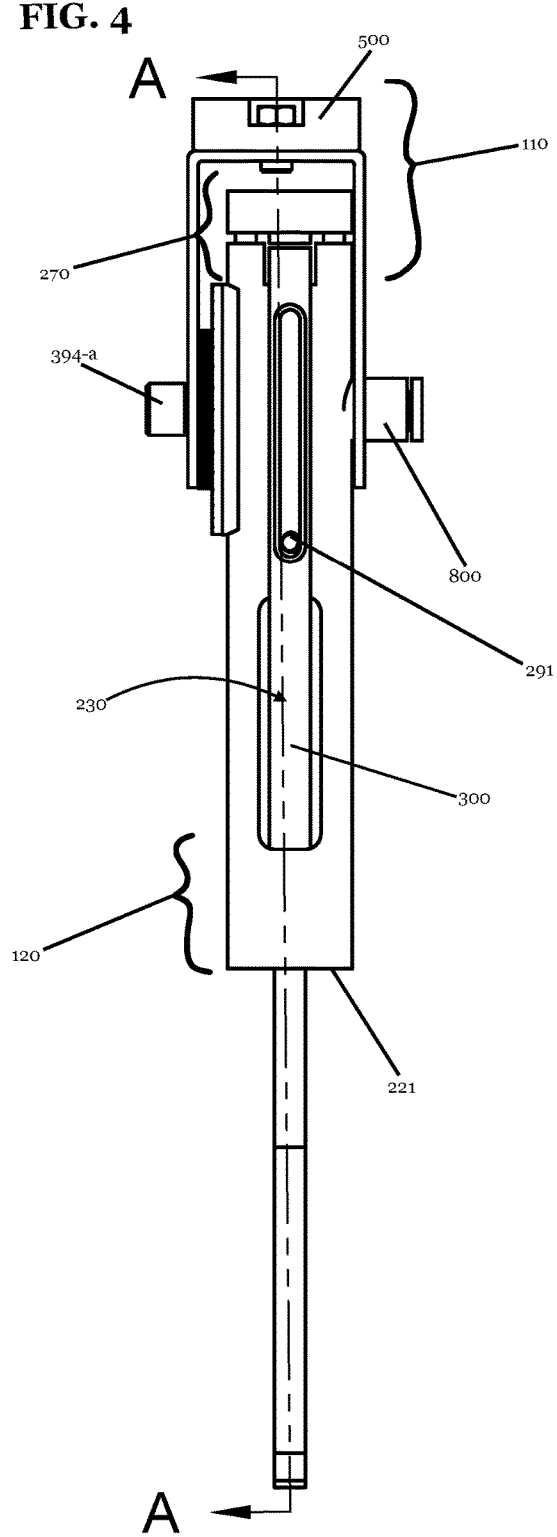
FIG. 4 depicts a perspective view from one side of the extractor clamping onto a femoral component.
Figure 5:
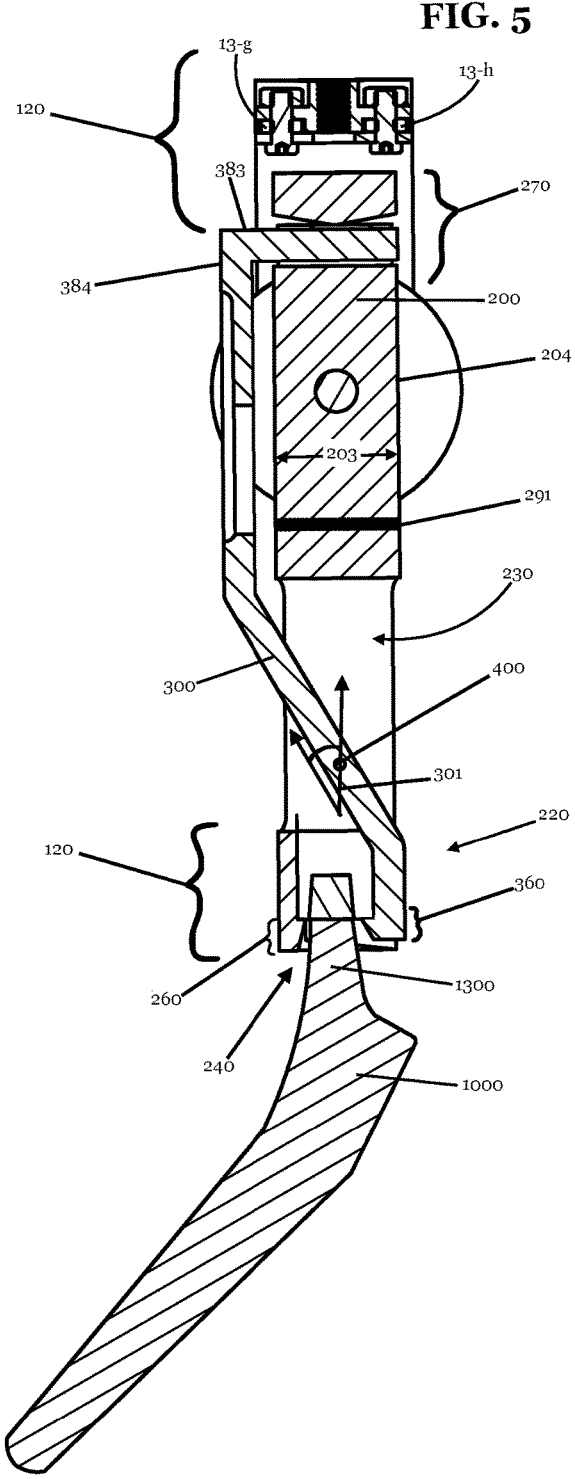
FIG. 5 depicts a cross-sectional view of the extractor in FIG. 4 clamping onto a femoral component.
Figure 7:
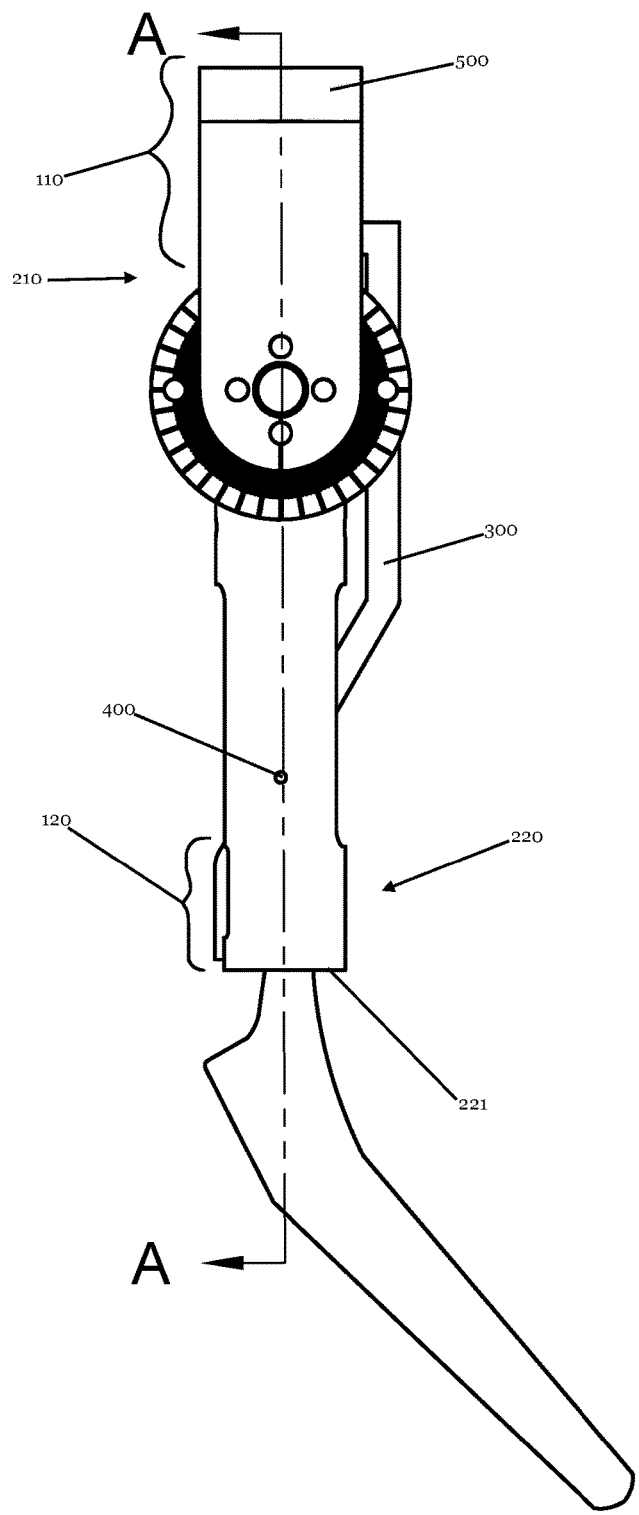
FIG. 7 depicts a perspective view of the extractor clamping onto a femoral component.

Located adjacent to the trunnion accepting structure 2102 is the lever opening 230. In the preferred embodiment, the lever opening 230 is in the form of a generally rectangular hole extending through the body 200 (though other shapes, such as an ovoid shape, are within the scope of the present invention). As FIGS. 3 and 4 illustrate, the lever opening 230 is shaped to accommodate the lever 300. As FIG. 5 illustrates, the lever 300 extends through the opening 230 at an angle 301 relative to the axis 201 of the body 200; preferably, the angle 301 measures 30 degrees (though it is within the scope of the present invention that the angle 301 measures between 25 and 65 degrees.

Turning now to FIG. 18, the lever opening 230 is provided with a lever ceiling 231 and two opposing lever walls 232, 233 (designated a "first" lever wall 232 and a "second" lever wall 233 to distinguish one from the other). The lever walls 232, 233 form two opposing planes that extend parallel to the axis 201 of the body 200. The lever walls 232, 233 terminate at the lever ceiling 231, which extends between the two opposing lever walls 232, 233 in a plane that is generally orthogonal to the axis 201 of the body 200.

Figure 26:
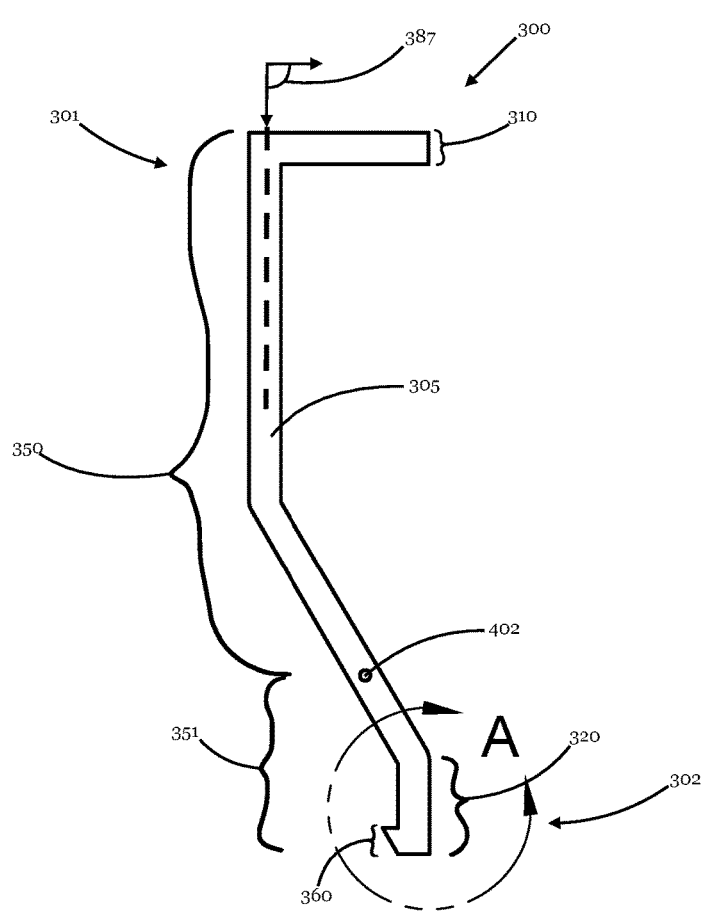
FIG. 26 depicts a perspective view of the lever included in the extractor.

The lever 300 is secured within the opening 230 of the body 200 via the fulcrum 400 which is in the form of a cylindrically-shaped stainless steel pin extending through an appropriately-sized, cylindrically-shaped, hole 401 defined within the body 200, as shown in FIG. 6 (also referred to as a "first fulcrum hole 401"), and an appropriately-sized, cylindrically-shaped, hole 402 defined within the lever 300, as shown in FIG. 26 (also referred to as a "second fulcrum hole 402"). As FIGS. 6, 7, 19 and 23 illustrate, the fulcrum hole 401 extends through the body 200 orthogonally relative to the first and second lever walls 232, 233 and the axis 201 of the body 200. As FIG. 23 also illustrates, the fulcrum hole 401 is located so that it extends across the lever opening 230 and through the axis 201 of the body 200 (and hence generally extends through the center of the body 200). Because a cylindrically-shaped stainless steel pin extends through both the first and second fulcrum holes 401, 402, the fulcrum holes 401, 402 are axially aligned. Naturally, one of ordinary skill in the art will appreciate that the foregoing positioning of the fulcrum hole 401 is only preferred and that the fulcrum hole 401 can be off-center and still function as a fulcrum 400 within the scope of the present invention.

The body 200 is configured to cooperate with the lever 300, which as shown in FIG. 26, is provided with a first end 310 and a second end 320. The body 200 and the lever 300 are also configured to cooperate with the natural gripping action applied by a surgeon's hand. As noted above, the outer surface 204 of the body 200 is cylindrically-shaped and therefore includes a diameter 203 (which is shown in FIG. 5). The diameter 203 of the body 200 is dimensioned to cooperate with a surgeon's hand; consequently, the diameter 203 of the body 200 measures between (and including) 1 and 3 inches. In the preferred embodiment, the diameter 203 is 1.5 inches.

Because the diameter 203 includes a dimension that ranges between 1 and 3 inches, the surgeon is able to encircle (at least in part) the body 200 with his or her hand and properly grip the extractor 100 while maintaining the surgeon's wrist in general alignment with the forearm (with minimal flexion, extension, or radial or ulnar deviation). Thus, the diameter 203 of the body 200 is dimensioned so that the body 200 and the lever 300 fit within a power gripping arrangement. As used herein, the term "power gripping arrangement" refers to the arrangement of the body 200 and the lever 300 that provide a grip wherein the fingers oppose the position of the thumb while curled about the outer surface 204 of the body 200.

The body 200, the lever 300, and the fulcrum 400 cooperate so that the body 200 and the lever 300 each act as a class 1 lever about the fulcrum 400. Accordingly, the extractor 100 is provided with a first force section 250 and a second force section 350 (as is shown in FIG. 3). The extractor 100 is also provided with a first resistance section 251 and a second resistance section 351 (as is also shown in FIG. 3).

The first force section 250 and the first resistance section 251 are located on the body 200 (as FIGS. 12, 16, 17, 19, 22, and 23 illustrate) while the second force section 350 and the second resistance section 351 are located on the lever 300 (as FIG. 26 illustrates). As shown in FIGS. 16, 17, 19, and 23, the first force section 250 extends from the fulcrum hole 401 toward the first end 210 of the body 200 while the first resistance section 251 extends from the fulcrum hole 401 to the second end 220 of the body 200. Similarly, as FIG. 26 illustrates, the second force section 350 extends from the fulcrum hole 402 toward the first end 310 of the lever 300 while the second resistance section 351 extends from the fulcrum hole 402 toward the second end 320 of the lever 300. Each of the force sections 250, 350 is positioned so that each opposes the other while rotating about the fulcrum 400 (as FIG. 3 depicts).

As FIG. 3 further depicts, the extractor 100 is provided with a clamping arrangement 130, which is located at the second end 120 of the extractor 100. Referring now to FIG. 5, the clamping arrangement 130 includes opposing clamping sections, a clamping section 260 located on the body 200 and a clamping section 360 located on the lever 300. (To distinguish the clamping section 360 of the lever 300 from the clamping section 260 of the body 200, the clamping section 260 of the body 200 shall be referred to as the "first" clamping section 260 while the clamping section 360 of the lever 300 shall be referred to as the "second" section 360 or "second clamping" section 360.)

The first clamping section 260 is located at the second end 220 of the body 200 while the second clamping section 360 is located at the second end 320 of the lever 300. As FIG. 5 illustrates, the first and second clamping sections 260, 360 cooperate with each other to clamp the neck 1300 of the femoral component 1000. The first and second clamping sections 260, 360 also cooperate with the gripping force of a surgeon's hand to clamp the neck 1300 of the femoral component 1000.

With the force sections 250, 350 acting about the fulcrum 400, the extractor 100 cooperates with the gripping force of the surgeon's hand to clamp the neck 1300 of the femoral component 1000 at the second end 220 of the body 200. The mechanical advantage obtained from the first and second force sections 250, 350 is further increased by the positioning of the fulcrum 400 towards the second end 220 of the body 200. As FIGS. 3 and 5 illustrate, the fulcrum 400 is positioned towards the second end 220 to provide the extractor 100 with increased force sections 250, 350.

Turning now to FIGS. 24 and 25, the extractor 100 is provided with an upper clamping surface 262 located in the clamping section 260 of the body 200 (which is shown in FIG. 5). The extractor 100 is also provided with an upper clamping surface 362 located on the lever 300 (shown in FIGS. 26 and 27). To distinguish one from the other, the upper clamping surface 262 located in the clamping section 260 of the body 200 shall be referred to as the "first" upper clamping surface 262 while the upper clamping surface 362 located on the lever 300 shall be referred to as the "second" upper clamping surface 362.

The first upper clamping surface 262 of the body 200 is oriented to be generally parallel with the second end surface 221 and generally orthogonal relative to the axis 201 of the body 200. The first upper clamping surface 262 abuts a body clamping surface 261, which, in turn, extends axially from the second end surface 221 and preferably at an angle 224 relative to the axis 201 of the body 200. As FIGS. 3 and 5 illustrate, the angle 224 measures 75 degrees; however, in alternative embodiments, the angle 224 ranges between 45 and 60 degrees. The first upper clamping surface 262 is generally co-planar with upper wedging surfaces 216, 218 (which are themselves co-planar with each other), and, in such a configuration, the first upper clamping surface 262 and the co-planar upper wedging surfaces 216, 218 form a single plane and thus a single surface which is oriented to be generally orthogonal to the axis 201 of the body 200.

Referring now to FIGS. 24 and 25, the upper wedging surfaces 216, 218 are configured to be placed into contact with the bottom surface 1104 of the trunnion 1102 and partially define the trunnion accepting structure 2102, which is located axially within the body 200 between the upper wedging surfaces 216, 218 and the lever opening 230. The trunnion accepting structure 2102 is provided with a plurality of trunnion accepting walls 2103, 2104, 2105 (referred to as "first," "second," and "third" trunnion accepting walls respectively). The first trunnion accepting wall 2103 is orthogonal to the first upper wedging surface 216 and extends axially from the first upper wedging surface 216 to the lever opening 230. The first trunnion accepting wall 2103 is generally parallel to the axis 201 of the body 200 and the first lever wall 232.

A second trunnion accepting wall 2104 is orthogonal to the second wedging surface 218 and extends axially from the second upper wedging surface 218 to the lever opening 230. Similar to the first trunnion accepting wall 2103, the second trunnion accepting wall 2103 is generally parallel to the axis 201 of the body 200 and the second lever wall 233. The first and second trunnion accepting walls 2103, 2104 are generally parallel to each other and spaced apart from each other so that the trunnion 1102 of a femoral component 1000 can fit between the two walls 2103, 2104.

Abutting the first and second trunnion accepting walls 2103, 2104 is a third trunnion accepting wall 2105. The third trunnion accepting wall 2105 is orthogonal to the first upper clamping surface 262 and extends axially from the from the first upper clamping surface 262 and terminates at the lever opening 230. The third trunnion accepting wall 2105 is oriented to be generally orthogonal to the first and second trunnion accepting walls 2103, 2104 and thus provides spacing between the first and second trunnion accepting walls 2103, 2104. In the preferred embodiment, the third trunnion accepting wall is at least 14 mm in width so that the first and second trunnion accepting walls 2103, 2104 are at least 14 mm apart. The preferred width of the third trunnion accepting wall 2105 is 22.222 mm so that the first and second trunnion accepting walls 2103, 2104 are spaced 22.222 mm apart.

The trunnion accepting walls 2103, 2104 extend from lever walls 232, 233 (with the first trunnion accepting wall 2103 extending from the first lever wall 232 and the second trunnion accepting wall 2104 extending from the second lever wall 233). As noted above, the first and second trunnion accepting walls 2103, 2104 terminate at the wedging structure 240 where the upper wedging surfaces 216, 218 are located.

Figure 12:
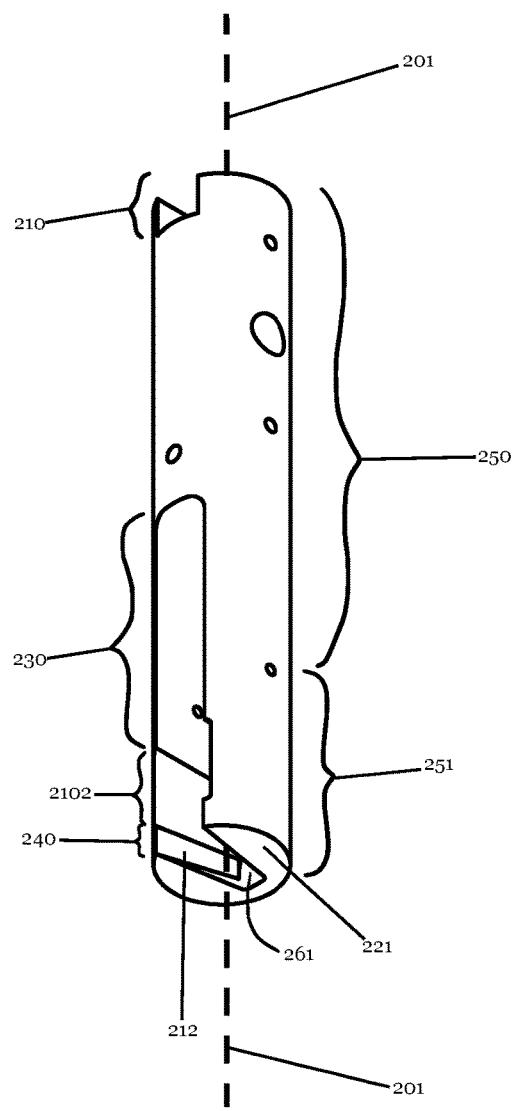
FIG. 12 depicts a perspective view of the body of the extractor.

Referring now to FIGS. 12, 14, and 18, the wedging structure 240 is located at the second end 220 of the body 200 (and the second end 120 of the extractor 100). As noted above, the wedging structure 240 is configured to wedge the second end 220 of the body 200 around the neck 1300 of the femoral component 1000 (at least partially). The wedging structure 240 is provided with a first wedging surface 212, a second wedging surface 213, a first upper wedging surface 216 and a second upper wedging surface 218. The wedging surfaces 212, 213 extend axially from the second end surface 221 and, in the preferred embodiment, abut the upper wedging surfaces 216, 218.

Figure 13:
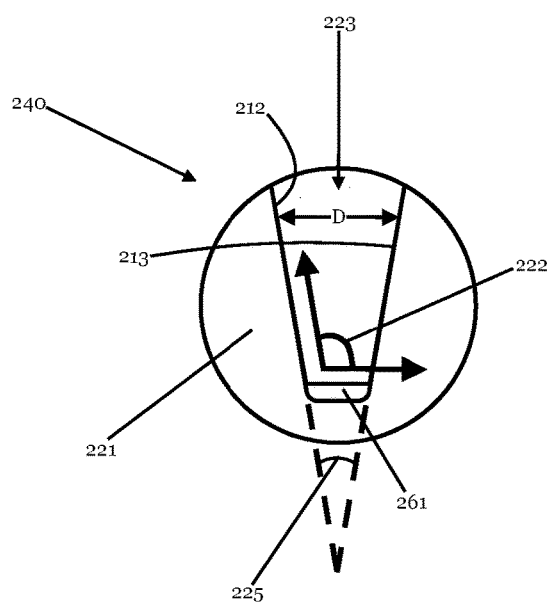
FIG. 13 depicts a perspective view of the body of the extractor.

Sandwiched between the wedging surfaces 212, 213 is a body clamping surface 261, as FIGS. 12, 13, and 18 illustrate. Each of the wedging surfaces 212, 213 extends from the body clamping surface 261 so that each of the wedging surfaces 212, 213 forms an angle 222 relative to the body clamping surface 261. As shown in FIG. 13, the angle 222 in the preferred embodiment measures 100 degrees; however, in an alternative embodiment, the angle measures between (and including) 90 and 110 degrees.

In the preferred embodiment, the wedging surfaces 212, 213 are of equal length and the angle 222 each wedging surface forms with the body clamping surface 261 is equal in magnitude (albeit in the opposite direction), as FIG. 13 illustrates. Consequently, as a matter of simple geometry, the wedging surfaces 212, 213 themselves form an angle 225 that preferably measures 20 degrees, but can range between 0 and 40 degrees (inclusively). Because each of the wedging surfaces 212, 213 extends from the body clamping surface 261 at an angle 222, the wedging surfaces are spaced from each other a distance (designated "D" in FIG. 13) that ranges between 0.2 and 0.85 inches, with the preferred range being between 0.2 and 0.75 inches.

As FIGS. 14, 17, and 24 illustrate, the wedging structure 240 includes the upper wedging surfaces 216, 218 which extend from the wedging surfaces 212, 213 in a generally orthogonal orientation. Because each of the wedging surfaces 212, 213 is oriented at an angle 222 and because the upper wedging surfaces 216, 218 extend from the wedging surfaces 212, 214, a spacing is created between the upper wedging surfaces 216, 218 that varies as the spacing between the wedging surfaces 212, 213 varies. Accordingly, the upper wedging surfaces 216, 218 are spaced from each other a distance "D" that ranges between 0.2 and 0.85 inches, with the preferred range being between 0.2 and 0.75 inches.

Because at least one of the wedging surfaces 212, 213 is oriented at an angle 222, the wedging surfaces 212, 213 provide the second end surface 221 of the body 200 with a tapered opening 223, as FIG. 13 illustrates. As noted above, the wedging surfaces 212, 213 abut the body clamping surface 261 located within the first clamping section 260. As FIG. 25 illustrates, the body clamping surface 261 is oriented to extend from the second end surface 221 at an angle 224 relative to the plane of the end surface 221 that measures 75 degrees. Though the angle 224 of the preferred embodiment measures 75 degrees, one of ordinary skill in the art will appreciate that the angle 224 in alternative embodiments ranges between 45 and 90 degrees. The body clamping surface 261 extends axially from the second end surface 221 and abuts the upper clamping surface 262 to form a tooth (which is designated "2018").

As noted above, the extractor 100 is provided with a lever 300 that includes a first end 301 and a second end 302. In the preferred embodiment, the lever 300 is an integral bar of stainless steel with a rectangular cross-sectional shape that has been bent to form a plurality of sections. Though the preferred embodiment is an integral bar of stainless steel that is rectangular in cross-sectional shape, alternative embodiments are circular or hexagonal in shape and formed by welding various sections together.

Figure 28:
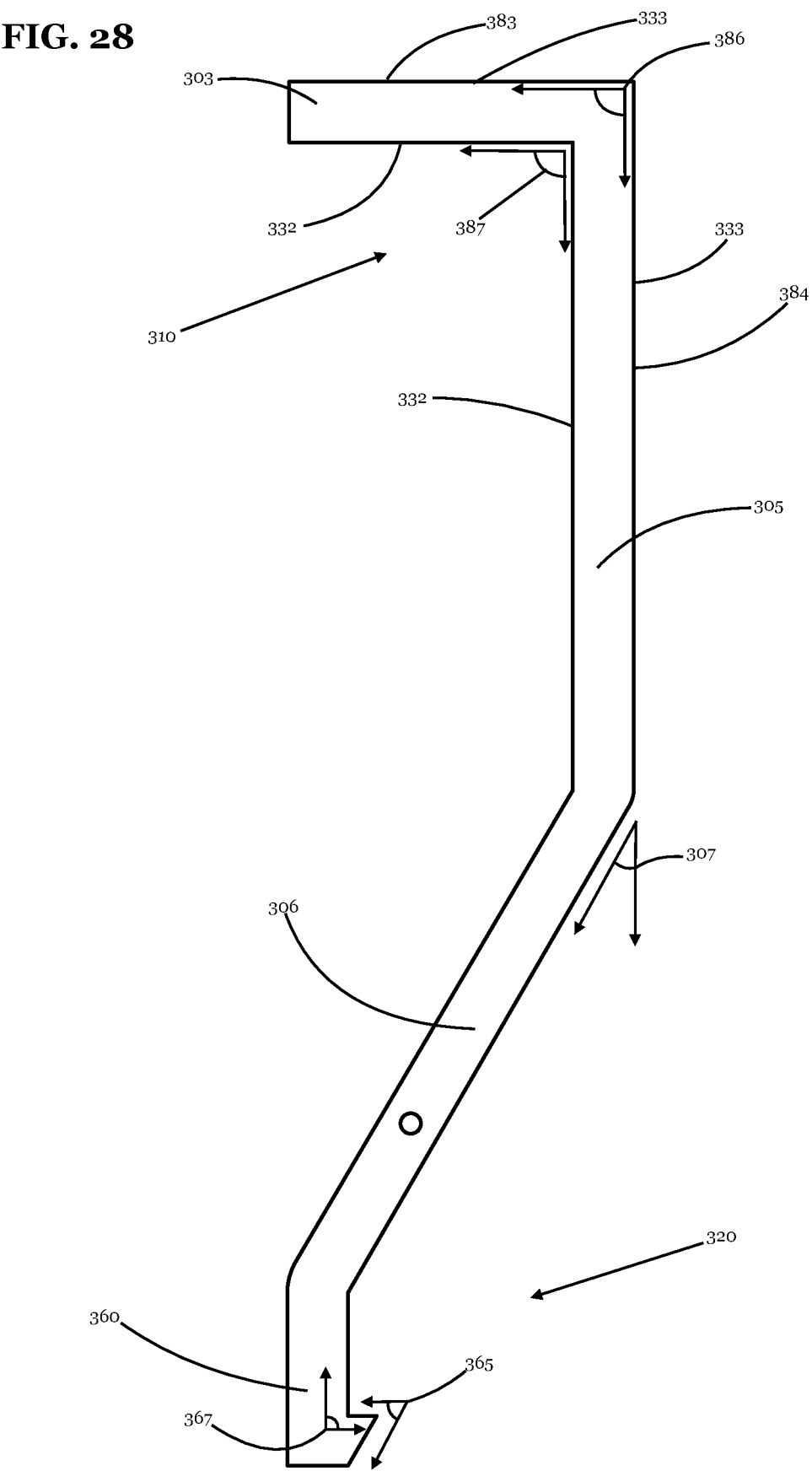
FIG. 28 depicts a perspective view of the lever included in the extractor.
Figure 31:
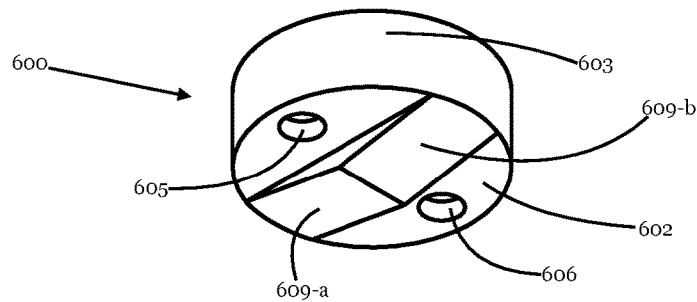
FIG. 31 depicts a perspective view of the locking component included in the extractor.

As FIG. 28 discloses, the lever 300 includes a first section 303, which extends from the first lever end 310, and a second section 360, which extends from the second lever end 320. (As noted above, the second section 360 is also referred to as the "second clamping section 360.") The lever 300 also includes a third section 305 and a fourth section 306. What has been identified as a "first" section 303 (and what shall also be referred to as a "locking" section 303) is provided with an orthogonal lever locking surface 383. The first section 303 (or locking section 303) abuts the third section 305 of the lever 300 to form an angle 387 that measures between 85 and 100 degrees. The third section 305 abuts the fourth section 306, which abuts the second section 360 (or the second clamping section 360).

The third section 305 of the lever 300 is located within the force section 350 (which is illustrated in FIG. 3) and is oriented to be generally parallel to the second section 360. As the foregoing implies, the third section 305 and the second section 360 (or second clamping section 360) are joined via the fourth section 306. Thus, the fourth section 306 extends between the third and second sections 305, 360 at an angle 307 that preferably measures 30 degrees, but, in alternative embodiments, ranges between 25 and 35 degrees. Consequently, the fourth section 306 is also referred to herein as the "angled" section 306 of the lever 300.

Figure 27:
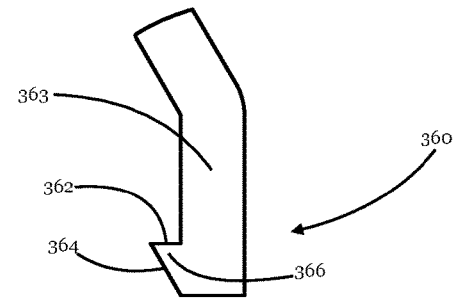
FIG. 27 depicts a detailed view of the lever in FIG. 26.

Extending from the fourth (or "angled") section 306 of the lever 300, the second section 360 (also referred to herein as the clamping section 360) functions as a clamp upon the neck 1300 of the femoral component 1000. As FIGS. 26 and 27 illustrate, the clamping section 360 of the lever 300 is provided with an upper lever clamping surface 362, and a trunnion clearance section 363. The trunnion clearance section 363 extends from the angled section 306 of the lever 300 and terminates at the upper lever clamping surface 362. As FIG. 28 illustrates, the upper lever clamping surface 362 extends from the trunnion clearance section 363 at an angle 367 that, in the preferred embodiment, measures 90 degrees. However, in an alternative embodiment, the upper lever clamping surface 362 is a curved surface that forms a plurality of angles with the trunnion clearance section 363 (in which case, the angle 367 measures between 0 and 90 degrees).

The upper lever clamping surface 362 terminates where it meets a lower lever clamping surface 364. The upper lever clamping surface 362 and the lower lever clamping surface 364 form an angle 365 that measures less than 90 degrees (though it is within the scope of the present invention for the angle to measure 90 degrees). In the preferred embodiment, the angle 365 measures 60 degrees. As FIG. 27 illustrates, the upper lever clamping surface 362 abuts the lower lever clamping surface 364 to form a tooth ridge that funtions as a tooth (and, as a result, the tooth ridge thus formed shall be referred to simply as a "tooth 366").

Figure 8:
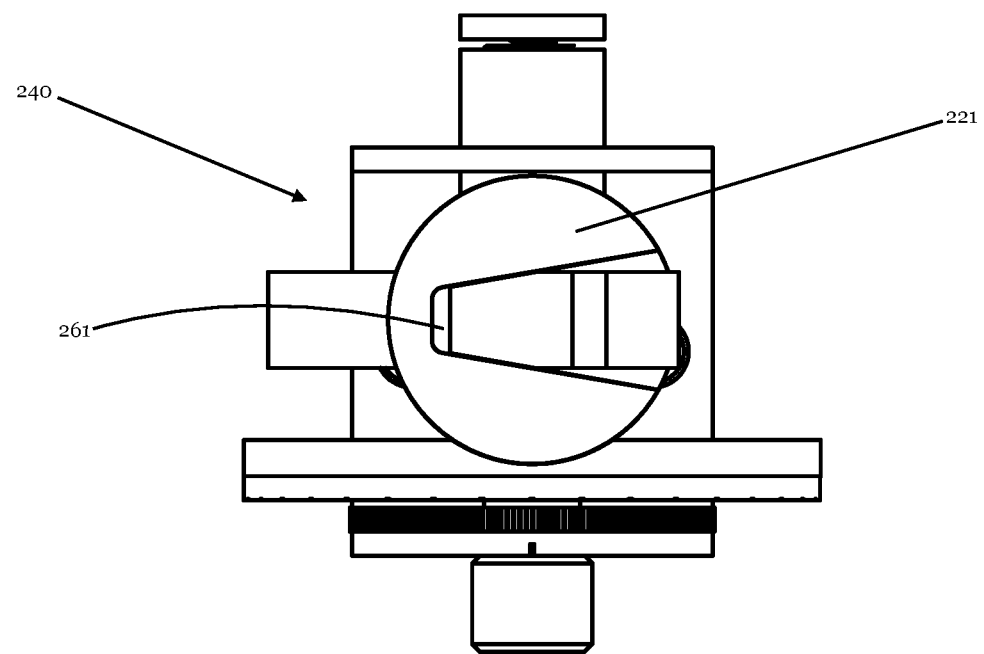
FIG. 8 depicts a perspective view of the extractor.
Figure 11:
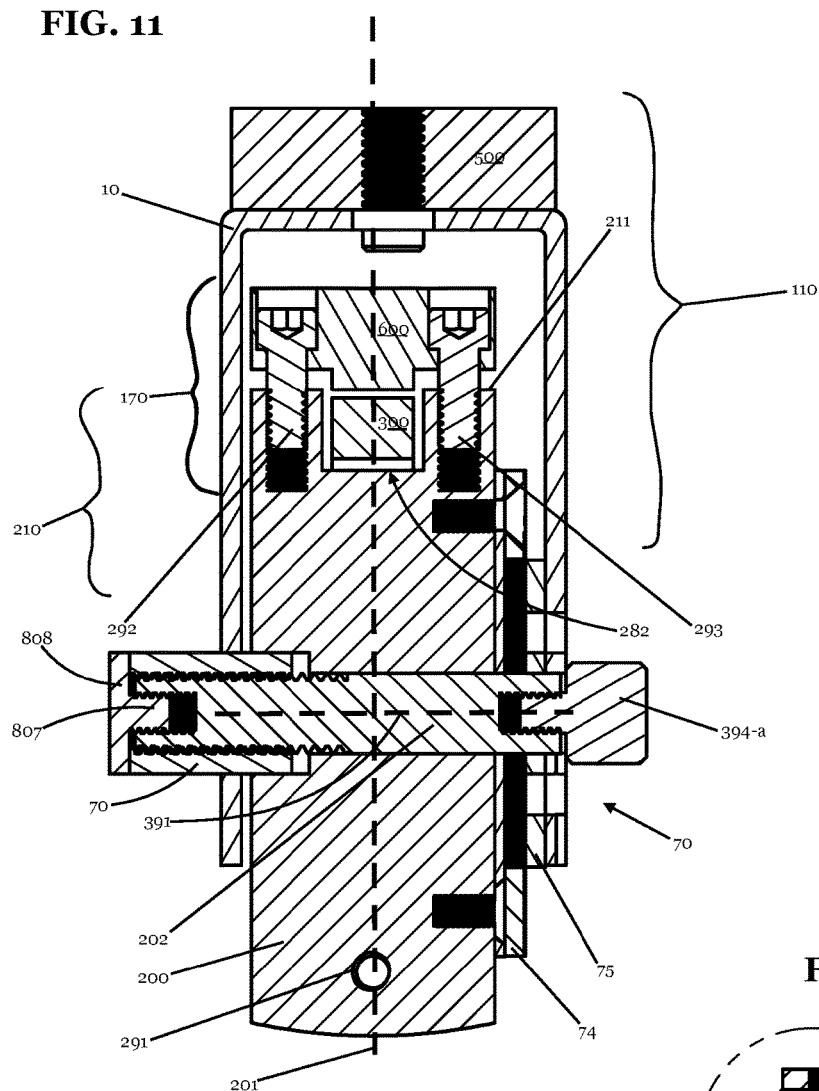
FIG. 11 depicts a detailed view of the cross-sectional view of the extractor in FIG. 10.
Figure 10:
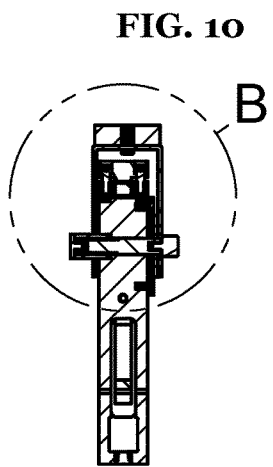
FIG. 10 depicts a cross-sectional view of the extractor in FIG. 9.
Figure 9:
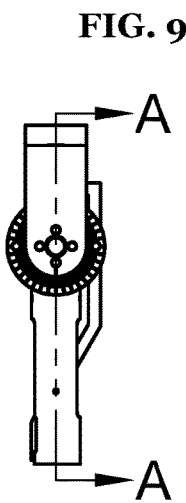
FIG. 9 depicts a perspective view of extractor.

Referring now to FIGS. 9-11, various views of the extractor 100 are shown. FIG. 10 is a cross-sectional view of the extractor 100 shown in FIG. 9, and FIG. 11 is a detailed cross-sectional view of the extractor 100 shown in FIG. 10. The foregoing figures depict the first end 210 of the body 200 configured to cooperate with the lever 300, (while FIGS. 5 and 8 depict the second end 220 of the body 200 configured to position the clamping arrangement 130 under the trunnion 1102 and onto the neck 1300 of the femoral component 1000).

As FIGS. 11 and 19 illustrate, the preferred embodiment is provided with a first threaded surface 291, which is defined within the force section 250 (and shown in FIG. 3). The first threaded surface 291 is coarsely threaded, preferably with a ¼-20 UNC thread profile, though a finely threaded profile (such as ¼-28 UNF) may also be used. Though the preferred embodiment is provided with a coarsely threaded surface 291 defined in the force section 250 of the extractor 100, in an alternative embodiment, the threaded surface 291 is in the form of a separate nut that receives a male threaded fastener, and though a coarse female thread is preferred, in an alternative embodiment, the body 200 is provided with a first threaded surface 291 that is in the form of a male threaded stud that is press-fit into an appropriately dimensioned hole within the body 200 (such as a stud with ¼-20 UNC or ¼-28 UNF thread profile).

As FIG. 19 shows, the first threaded surface 291 extends through the body 200 and is oriented to extend orthogonally through the axis 201 of the body 200. Though the first threaded surface 291 is oriented to be orthogonal to the axis 201, in an alternative embodiment, the first threaded surface 291 is oriented at an angle that measures less than 90 degree relative to the axis 201, such as 45 degrees, or greater than 90 degrees relative to the axis 201, such as 135 degrees. Though the first threaded surface 291 extends through the axis 201 of the body 200 in the preferred embodiment, in alternative embodiments, the first threaded surface 291 extends through the body 200 offset from the axis 201.

The first end 110 of the extractor 100 is provided with a fastener (preferably a plurality of fasteners) that are configured to lock the lever 300 into the first end 210 of the body 200 after the clamping arrangement 130 has been secured to the neck 1300 of the femoral component 1000. Accordingly, the first end 110 of the extractor 100 is provided with a locking arrangement 170, and, as FIG. 11 depicts, the locking arrangement 170 is provided with a threaded surface and a fastener. In the preferred embodiment, the locking arrangement 170 is provided with a plurality of threaded surfaces (referred to as a "second" threaded surface 292 and a "third" threaded surface 293 to distinguish one from the other).

As FIG. 11 illustrates, the threaded surfaces 292, 293 are defined within the body 200 and extend axially from the first end surface 211 towards the second end surface 221. The threaded surfaces 292, 293 are dimensioned according to a plurality of male threaded fasteners. In the preferred embodiment, the second and third threaded surfaces 292, 293 are blind holes that have been drilled on a bolt circle measuring 1 1/16 in diameter so that each of the threaded surfaces 292, 293 is located 180 degrees from the other and positioned on either side of a slot 282 defined within the first end 210 of the body 200 (as shown in FIGS. 14, 15, and 23-25). It is preferred that the second and third threaded surfaces 292, 293 are coarsely threaded with a 1/4-20 UNC thread profile; however, in an alternative embodiment, the threaded surfaces 292, 293 are finely threaded with a 1/4-28 UNF thread profile.

While the preferred embodiment is provided with threaded surfaces 292, 293 that accept male threaded fasteners, such as a socket head cap screw, in an alternative embodiment, the threaded surfaces 292, 293 accept female threaded fasteners such as nuts. In such an alternative embodiment, the threaded surfaces 292, 293 extend axially from the first end surface 211 in the form of threaded studs that have been press-fit into holes extending into the body 200.

Figure 23:
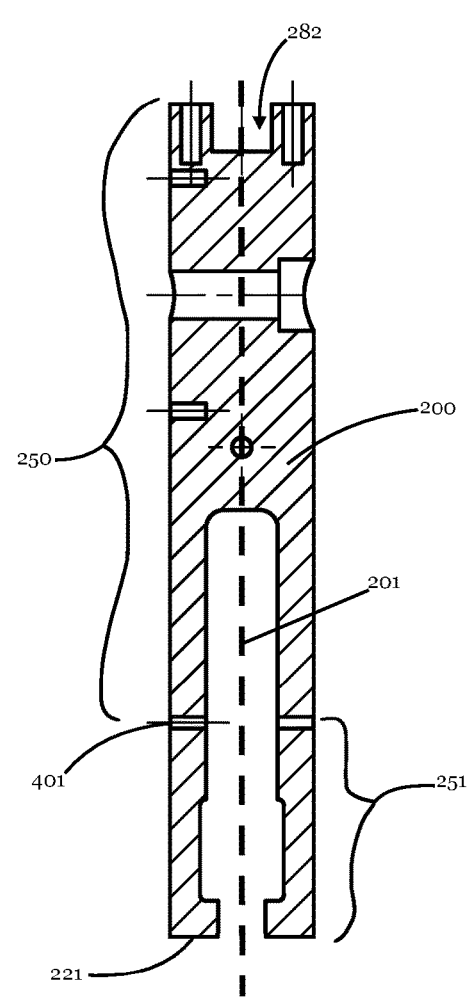
FIG. 23 depicts a cross-sectional view of the body of the extractor in FIG. 22.

Returning again to FIG. 11, the locking arrangement 170 includes a slot 282, which is defined within the first end 210 of the body 200. The slot 282 is both positioned and dimensioned according to the lever 300. In the preferred embodiment, the slot 282 is positioned so that it is in alignment with the lever 300. The slot 282 is dimensioned to accept at least a portion of the lever 300 therewithin as FIG. 11 depicts. Thus, the slot 282 extends both axially into the body 200 (as FIGS. 14 and 15 illustrate) and radially across the first end surface 211 (as FIGS. 19 and 23 illustrate). As FIGS. 19 and 23 further illustrate, the slot 282 is generally rectangular in cross-section and is provided with a slot axis 283 that is generally orthogonal to the axis 201 of the body 200. As FIGS. 17, 18, and 24 illustrate, the slot 282 is defined by a slot floor 284 that forms a plane that is generally parallel to the slot axis 283; the slot 212 is further defined by two opposing slot walls (designated a "first" slot wall 285 and a "second" slot wall 286 to distinguish one from the other) that extend orthogonally from the slot floor 284 with each terminating at the first end surface 211 of the body 200.

As FIGS. 17, 18, and 24 make clear, the plane of the slot floor 284 and the plane of the lever ceiling 231 are generally parallel to each other. Similarly, each of the slot walls 285, 286 forms a plane that is generally parallel to the plane of at least one of the lever walls 232, 233. In the preferred embodiment, the plane of the first slot wall 215 is generally parallel to the plane of the first lever wall 232; in the same vein, the plane of the second slot wall 286 is generally parallel to the plane of the second lever wall 233. Thus, the slot 282 and the lever opening 230 are oriented to extend through the body 200 so that each is generally parallel to the other.

As noted above, and as shown in FIG. 11, the slot 282 is shaped to accept at least a portion of the first end 310 of the lever 300. The lever 300 is provided with an angle 387 (shown in FIG. 26) formed from the locking section 303 and the third section 305 of the lever 300. The angle 387 is dimensioned so that the locking section 303 (shown in FIG. 28) extends into the slot 282 defined within the first end 210 of the body 200 when the extractor 100 is being clamped onto the femoral component 1000. As noted above, and as FIG. 28 further shows, the locking section 303 of the lever 300 extends from the first lever end 310 and abuts the third section 305 of the lever 300 so that angle 387 measures between 85 and 100 degrees.

As FIG. 28 additionally illustrates, the lever 300 is provided with a surface that is internal to the angle 387 between the locking section 303 and the third section 305 as well as a surface that is external to the angle 387 between the locking section 303 and the third section 305. The surface that is internal to the angle 387 between the locking section 303 and the third section 305 shall be referred herein to as an "interior lever surface 332" while the surface that is external to the angle 330 between the locking section 303 and the third section 305 shall be referred to herein as an "exterior lever surface 333." The exterior lever surface 333 is provided with a plurality of sub-surfaces, including the orthogonal lever locking surface 383 (which extends from the extreme end of the locking section 303 and terminates at the third section 305 of the lever 300), and a parallel lever locking surface 384 (which extends from where the orthogonal lever locking surface 383 terminates). The parallel lever locking surface 384 is located on the third section 305 of the lever 200 (within the force section 350) and extends to the fourth (or "angled") section 306.

Turning now to FIG. 3, the orthogonal lever locking surface 383 is configured to extend in a generally orthogonal orientation to the axis 201 of the body 200 when the lever 300 is clamped onto the neck 1300 of the femoral component 1000 and locked in place. In contrast, the parallel lever locking surface 384 is configured to extend in a generally parallel orientation relative to the axis 201 of the body 200 when the lever 300 is clamped onto the neck 1300 of the femoral component 1000. Thus, the orthogonal lever locking surface 383 forms an angle 386 with the parallel lever locking surface 384 that measures between 85 and 100 degrees with the preferred angle 386 measuring 95 degrees. To fabricate the angle 386 between the orthogonal lever locking surface 383 and the parallel lever locking surface 384, rectangular bar stock is bent so that the locking section 303 is generally perpendicular relative to the third section 305; then the orthogonal lever locking surface 383 is machined so that the preferred angle 386 with the parallel lever locking surface 384 is achieved.

Figure 20:
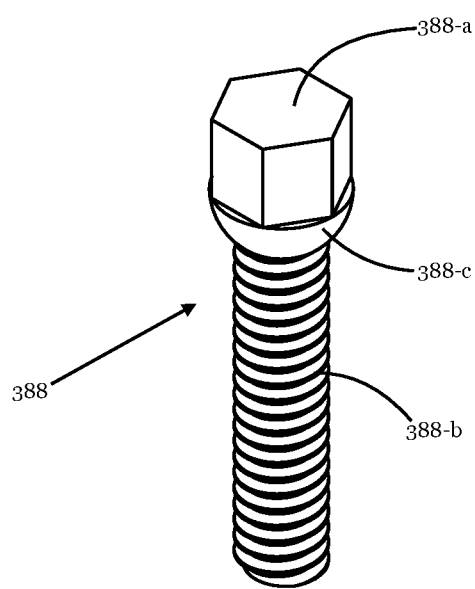
FIG. 20 depicts a perspective view of a fastener included in the extractor.
Figure 21:
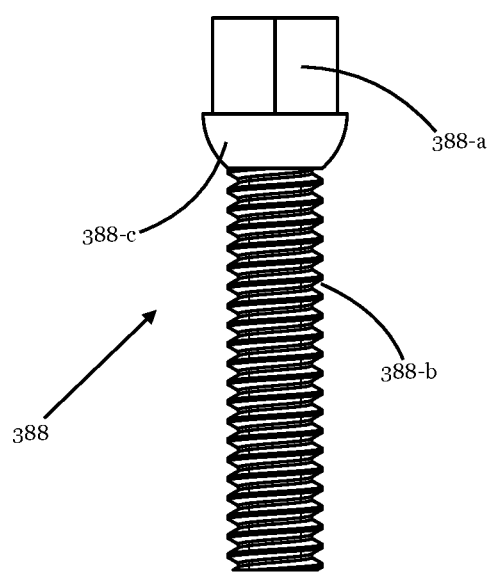
FIG. 21 depicts a perspective view of a fastener included in the extractor.
Figure 22:
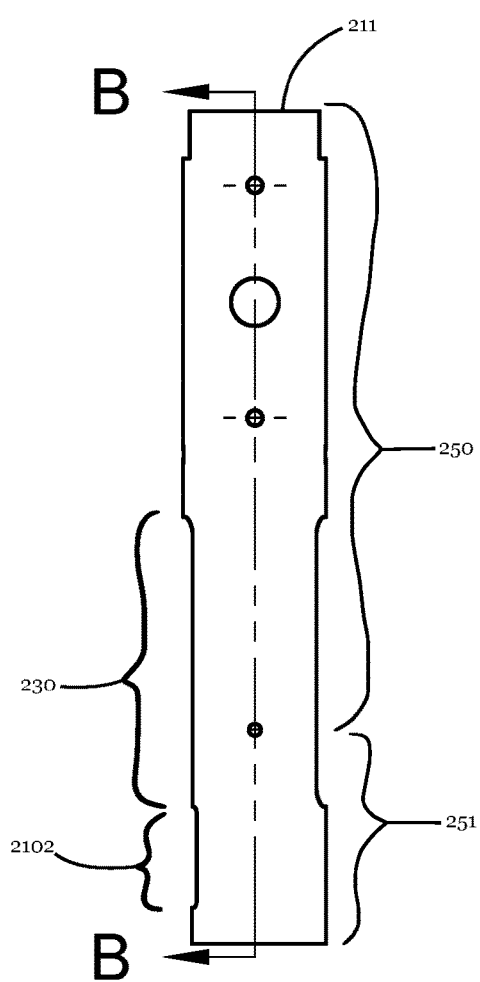
FIG. 22 depicts a perspective view of the body of the extractor.

The parallel lever locking surface 384 is provided with a grooved slot 385 that is shaped to cooperate with a male threaded fastener 388 (shown in FIGS. 20-21) with a head 388-a and a shank 388-b, preferably a bolt that is provided with a hexagonal head and a 1/4-20 UNC threaded shank. For ease of reference, the male threaded fastener 388 shall be referred simply as the "first fastener 388" in order to distinguish this fastener from other fasteners referred to herein. Referring now to FIGS. 29 and 30, the grooved slot 385 includes a groove 385-a that is semi-circular in cross-section and a slot 385-b that is defined within the groove 385-a. The groove is dimensioned so that the head 388-b of the first fastener 388 clamps the third section 305 of the lever 300 while the slot 385-b is dimensioned so that the shank 388-b passes through to engage the threads of the first threaded surface 291 defined within the body 200. Advantageously, the bearing surface 388-c of the first fastener 388 is spherically shaped to bear against the groove 385-a (which therefore functions as a bearing surface). Alternatively, a spherically or semi-spherically shaped washer could also be employed.

To clamp the extractor 200 onto the neck 1300 of the femoral component 1000, the lever 300 is rotated about the fulcrum 400 so that the clamping section 360 is moved to a position in closer proximity to the clamping section 260 of the body 200 and the locking section 303 enters the slot 282 defined within the body 200. Thus, the angle 386 between the orthogonal lever locking surface 383 and the third section 305 of the lever 300 is dimensioned according to the slot 282 defined within the first end 210 of the body 200. When the lever 300 is locked into place onto the body 200, the second section 304 (and the third section 305, which is parallel to the second section 304) are oriented relative to the body 200 so as to form an angle relative to the axis 201 measuring between +5 degrees and −5 degrees, with the preferred range being +5 degrees and −3 degrees.

As noted above, when the extractor 100 is being clamped onto the neck 1300 of the femoral component 1000, at least a portion of the lever 300 extends through the lever opening 230. As is also noted above, the lever 300 is rotatably secured to the body 200 via the fulcrum 400 so that the clamping section 360 of the lever 300 rotates towards the clamping section 260 of the body 200. Accordingly, when the clamping section 360 of the lever 300 is rotated towards the clamping section 260 of the body 200, the locking section 303 of the lever 300 is simultaneously rotated towards the locking arrangement 270 located at the first end 110 of the extractor 100. Conversely, when the extractor 100 releases the neck 1300 of the femoral component 1000, the clamping section 360 of the lever 300 is rotated away from the clamping section 260 of the body 200, and the locking section 303 of the lever 300 is simultaneously rotated away from the locking arrangement 270 located at the first end 110 of the extractor 100.

As the locking section 303 of the lever 300 is rotated towards the locking arrangement 270 located at the first end 110 of the extractor 100, the locking section 303 of the lever 300 enters the slot 282 at the first end 210 of the body 200 with the orthogonal lever locking surface 383 facing away from the slot floor 284. At the same time, the clamping section 360 of the lever 300 approaches the wedging structure 240 located within the clamping section 260 of the body 200. Consequently, the clamping section 360 of the lever 300 approaches the wedging structure 240, which is located within the clamping section 260 of the body 200 (and hence approaches the wedging surfaces 212, 213 which are located within the wedging structure 240). Thus, as the lever 300 pivots about the fulcrum 400, at least a portion of the lever 300 is accommodated within the slot 282, which is located at the first end 210 of the body 200, and, at least a portion of the lever 300 is accommodated within the wedging structure 240, which is located at the second end 220 of the body 200.

As noted above, the body 200 and the lever 300 are dimensioned to provide a power gripping arrangement; by squeezing the body 200 and the third section 304 of the lever 300 together, the surgeon rotates the clamping section 360 of the lever 300 and the clamping section 260 of the body 200 closer together. As is also noted above, in the foregoing power gripping arrangement, the body 200 itself and the lever 300 act as class 1 levers. Additionally, as is further noted above, the fulcrum 400 is positioned towards the clamping arrangement 130 of the extractor 100, thereby increasing the force sections 250, 350 of the extractor 100 and decreasing the resistance sections 251, 351 of the extractor 100.

With the force sections 250, 350 increased and the resistance sections 251, 351 decreased, the mechanical advantage of the extractor 100 is increased. Thus, the gripping force applied to the force sections 250, 350 of the extractor 100 yields a greater clamping force at the resistance sections 251, 351 where the clamping arrangement 130 of the extractor 100 is located.

The clamping force of the clamping arrangement 130 is further increased by the fastening structures included with the extractor 100. As FIGS. 2, 4, 5, 17, 19, and 25 illustrate, the body 200 is provided with a threaded surface, preferably a plurality of threaded surfaces in a plurality of orientations. As noted above, the body 200 is provided with a first threaded surface 291 that extends into the body 200 in an orientation that is generally orthogonal to the axis 201 of the body 200. The body 200 is also provided with second and third threaded surfaces 292, 293 that extend into the body 200 in an orientation that is generally parallel to the axis 201 of the body 200.

As noted above, the second and third threaded surfaces 292, 293 are oriented to be parallel to the axis 201 of the body 200. Though the second and third threaded surfaces 292, 293 are oriented to be parallel to the axis 201, in an alternative embodiment, the second and third threaded surfaces 292, 293 are oriented at an angle that measures less than 180 degrees relative to the axis 201, such as 135 degrees.

Figure 53:
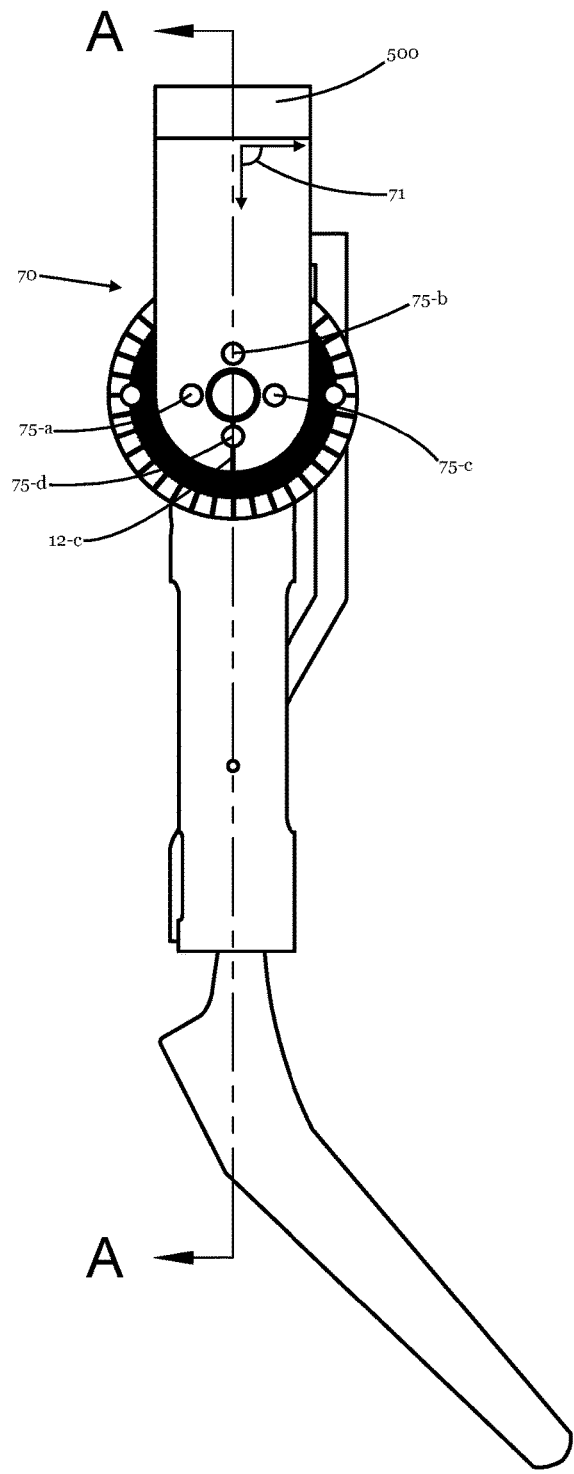
FIG. 53 depicts a perspective view of the extractor with the bracket configured to lock in place while the jaws clamp a femoral component.
Figure 54:
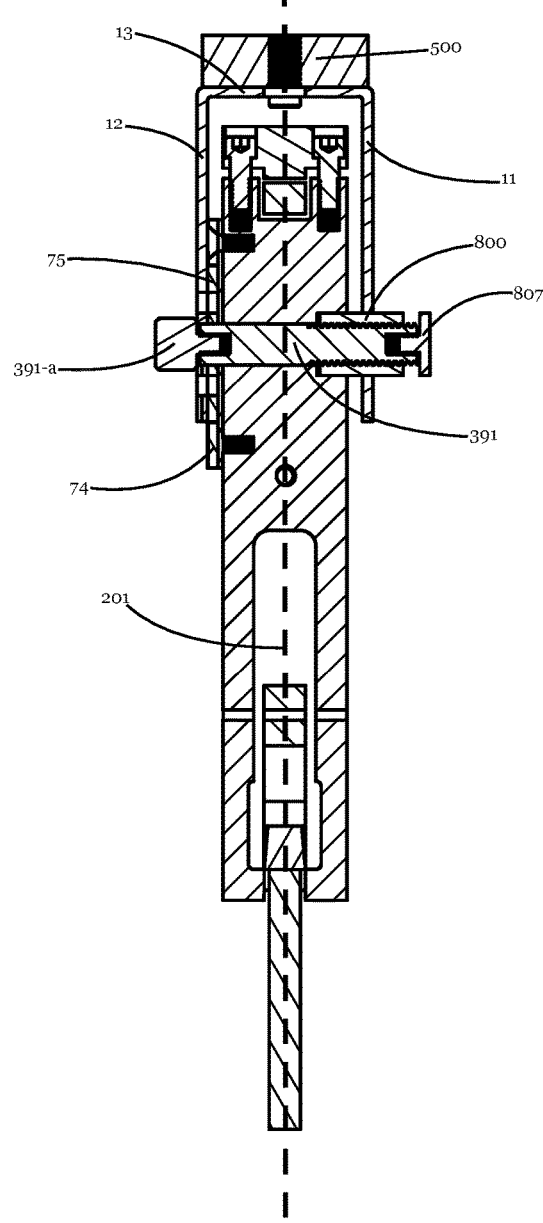
FIG. 54 depicts a cross-sectional view of the extractor depicted in FIG. 53.

Referring now to FIGS. 53 and 54, the preferred embodiment is shown clamped onto the neck 1300 of the femoral component 1000 and locked in place. To clamp the extractor 100 onto the neck 1300 of the femoral component 1000, the trunnion accepting structure 2102 is exposed by rotating the lever 300 so that the first end 310 rotates away from the first end 210 of the body 200 (and hence towards the second end 220). Because the lever 300 moves about the fulcrum 400, the second end 320 of the lever 300 is also rotated, albeit in the opposite direction (namely, away from the second end 220 of the body 200 and towards the first end 210 of the body 200). Thus, the second end 320 of the lever 300 is rotated away from the trunnion accepting structure 2102.

After the trunnion accepting structure 2102 is thus exposed, the trunnion accepting structure 2102 is then placed over the trunnion 1102 of the femoral component 1000 so that at least a portion of the upper wedging surfaces 216, 218 of the body 200 is in contact with the bottom surface 1104 of the trunnion 1102. By placing the upper wedging surfaces 216, 218 into contact with the bottom surface 1104 of the trunnion 1102, the upper wedging surfaces 216, 218 of the body 200 are oriented to be generally parallel with the bottom surface 1104 of the trunnion 1102. Because the bottom surface 1104 of the trunnion 1102 is generally orthogonal to the trunnion axis 1101 and because the upper wedging surfaces 216, 218 are generally orthogonal to the axis 201 of the body 200, the axis 201 of the body 200 is generally parallel with the axis 1101 of the trunnion 1102.

After the trunnion 1102 is placed within the trunnion accepting structure 2102, the lever 300 is rotated so that the first end 310 approaches the first end 210 of the body 200 (and, accordingly, the second end 320 of the lever 300 approaches the second end 220 of the body 200). As described above, the lever 300 and the body 200 are configured to clamp the neck 1300 of the femoral component 1000 and wedge the trunnion 1102 within the trunnion accepting structure 2102. As is further described above, the clamping section 360 of the lever 300, as well as the clamping section 260 of the body 200, are each provided with a tooth 366, 2018. The lever 300 is dimensioned to rotate about the fulcrum 400 so that the tooth 366 on the clamping section 360 of the lever 300 opposes the tooth 2018 on the clamping section 260 of the body 200. Thus, the opposing teeth 366, 2018 form a set of clamping jaws. (Consequently, the teeth 366, 2018 shall also be referred to herein as "clamping jaws" 366, 2018.)

With the upper wedging surfaces 216, 218 of the body 200 contacting the bottom surface 1104 of the trunnion 1102, the tooth 366 on the clamping section 360 of the lever 300 pushes the neck 1300 of the femoral component 1000 toward the opposing tooth 2018 on the clamping section 260 of the body 200 when the third section 304 of the lever 300 is pressed towards the body 200. Thus, when the force sections 250, 350 of the extractor 100 are pressed together, the resistance sections 251, 351 clamp the neck 1300 of the femoral component 1000.

As the tooth 366 on the clamping section 360 of the lever 300 pushes the neck 1300 toward the opposing tooth 2018, the neck 1300 is pushed into the wedging surfaces 212, 213 of the wedging structure 240 and at least a portion of the bottom surface 1104 of the trunnion 1102 is positioned axially so that it is generally parallel to a portion of at least one of the upper wedging surfaces 216, 218. With the bottom surface 1104 positioned axially over a portion of at least one of the upper wedging surfaces 216, 218, at least one of the upper wedging surfaces 216, 218 exerts a normal force upon at least a portion of the bottom surface 1104 of the trunnion 1102 when the extractor 100 is impacted. Naturally, it is preferred that the bottom surface 1104 of the trunnion 1102 be positioned axially over both of the upper wedging surfaces 216, 218 so that both upper wedging surfaces 216, 218 exert a normal force upon the bottom surface 1104 of the trunnion 1102 when the extractor 1000 is impacted.

To prevent the clamping sections 260, 360 from loosening, the extractor 100 is provided with a locking component 600. As FIGS. 31-35 illustrate, the locking component 600 is shaped according to the body 200 and includes a plurality of surfaces and structures. The locking component 600 is provided with a first outer surface 601, a second outer surface 602, and a third outer surface 603. The third outer surface 603 is cylindrical about an axis 604 and provided with a diameter 605 that is dimensioned according to the diameter 203 of the body 200. In the preferred embodiment, both diameters 203, 605 are 1.5 inches. The cylindrically-shaped third outer surface 603 abuts the first and second outer surfaces 601, 602, which generally extend radially from the axis 604.

Figure 32:
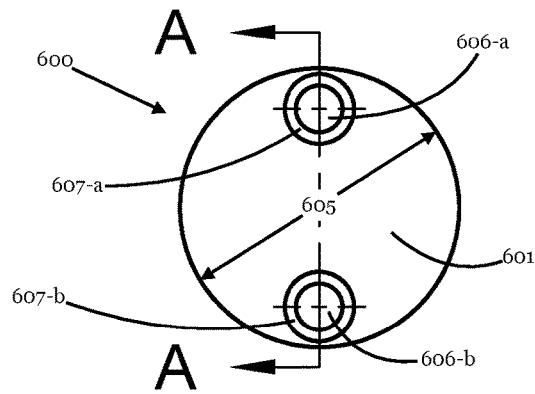
FIG. 32 depicts a perspective view of the locking component included in the extractor.
Figure 33:
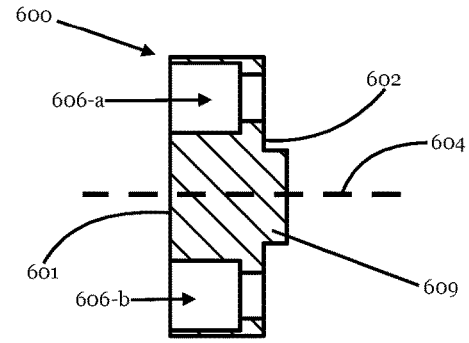
FIG. 33 depicts a cross-sectional view of the locking component in FIG. 32.
Figure 34:
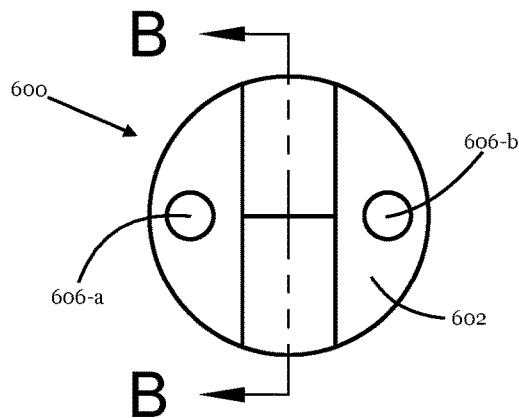
FIG. 34 depicts a perspective view of the locking component included in the extractor.
Figure 35:
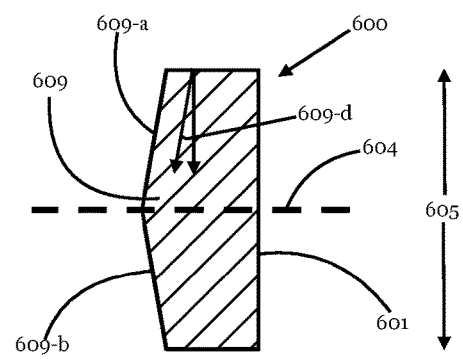
FIG. 35 depicts a cross-sectional view of the locking component in FIG. 34.

A through-hole extends from the first outer surface 601 to the second outer surface 602. As FIGS. 31-35 illustrate, the preferred embodiment is provided with a plurality of through-holes 606-a, 606-b that are circular and dimensioned to accept a male fastener; thus, as FIG. 32 illustrates, the first outer surface 601 is provided with a plurality of bearing surfaces 607-a, 607-b for the head of the male fastener. The second outer surface 602 is provided with a locking ridge 609 that is formed where two ramps 609-a, 609-b abut one another. Each of the ramps 609-a, 609-b extends radially from the axis 604 to the third outer surface 603. Each of the ramps 609-a, 609-b also extends axially from the second outer surface 602 as each ramp extends radially inward from the third outer surface 603 to form a crest 609-c where each ramp meets the other. Thus, each of the ramps 609-a, 609-b forms an angle 609-d with the second outer surface 602 of the locking component 600 that measures at least 5 degrees and preferably 10 degrees, as FIG. 35 illustrates.

In the preferred embodiment, the through-holes 606-a, 606-b have been drilled on a bolt circle extending around the axis 604 that matches the locations of the threaded surfaces 292, 293 defined within the body 200; consequently, the through-holes 606-a, 606-b are drilled on a bolt circle measuring 1 1/16 in diameter so that each of the through-holes 606-a, 606-b is located 180 degrees from the other and positioned on either side of the ramps 609-a, 609-b. The through-holes 606-a, 606-b are then counter-bored to provide bearing surfaces 607-a, 607-b for male threaded fasteners (which, in the preferred embodiment, are 1/4-20 UNC socket head cap screws). For ease of reference, the foregoing male threaded fasteners shall be referred to as "socket head cap screws."

As the foregoing indicates, the through-holes 606-a, 606-b are positioned to line up with the threaded surfaces 292, 293 of the body 200, and the ramps 609-a, 609-b and the locking ridge 609 are positioned to extend within the slot 282 of the body 200. Thus, when the socket head cap screws are passed through the through-holes 606-a, 606-b and torqued into the threaded surfaces 292, 293 of the body 200, the ramps 609-a, 609-b and the locking ridge 609 extend into the slot 282 of the body 200.

As noted above, the fulcrum 400 is positioned so that the mechanical advantage of the first and second force sections 250, 350 of the extractor 100 is increased. As a result, when the surgeon squeezes the first and second force sections 250, 350 together, the tooth 366 on the lever 300 exerts a greater force upon the neck 1300 of the trunnion 1102 thereby forcing the neck 1300 into the wedging surfaces 212, 213 of the body 200 thereby creating an interference fit between the second end 120 of the extractor 100 and the neck 1300 of the femoral component 1000. Much as the upper wedging surfaces 212, 213 exert a normal force upon the bottom trunnion surface 1104, the upper lever clamping surface 362 on the lever 300 contacts the bottom trunnion surface 1104 and exerts a normal force upon the bottom trunnion surface 1104 when the extractor 100 is impacted.

After the lever 300 and the body 200 are positioned so that the extractor 100 is in clamping and wedging engagement with the femoral component 1000, the lever 300 and the body 200 are locked in place. By torqueing the first fastener 388 into the first threaded surface 291 defined within the body 200, the head 388-a of the first fastener 388 clamps the parallel lever locking surface 384 of the lever 300 and draws the third section 305 of the lever 300 towards the body 200, placing tension upon the first fastener 388. Because the first threaded surface 291 is located in the first force section 250 of the extractor 100 and the parallel locking surface 384 of the third section 305 of the lever 300 is located in the second force section 350 of the extractor 100, the clamping force exerted by the tension placed upon the first fastener 388 exerts a greater clamping force upon the jaws 366, 2018 clamping the femoral component 1000.

The locking component 600 further locks in place the lever 300 and the body 200. As noted above, when the neck 1300 of the femoral component 1000 is clamped, the locking section 303 of the lever 300 is disposed (at least partially) within the slot 282 defined within the first end 210 of the body 200. Furthermore, when the locking section 303 of the lever 300 is disposed within the slot 282 of the body 200, the orthogonal lever locking surface 383 faces away from the slot floor 284 and therefore faces the locking ridge 609 of the locking component 600. As a result, when the socket head cap screws are passed through the holes 606-*a*, 606-*b* defined within the locking component 600 and torqued into the threaded surfaces 292, 293 of the body 200, the locking ridge 609 is pressed into the orthogonal lever locking surface 383 of the lever 300 (which places the socket head cap screws in tension). Thus, the tension placed on the socket head cap screws exerts a clamping force upon the lever 300, which then exerts a clamping force upon the neck 1300 of the femoral component 1000 while it is wedged within the wedging structure 240 of the body 200.

As FIG. 11 illustrates, the extractor 100 is provided with a bracket 10, which is supported by a shaft 390 extending through the body 200. The bracket 10 and the shaft 390 rotate together and are therefore configured to cooperate with the angle selector 70. As FIGS. 37-41 illustrate, the bracket 10 is provided with a plurality of sections. By stamping or bending a piece of ⅛ inch stainless steel plate, the bracket 10 is provided with a leg section and a plate section. Ideally, the bracket is provided with a plurality of leg sections; accordingly, as FIGS. 37-41 illustrate, the preferred embodiment is provided with a first leg section 11 and a second leg section 12. The leg sections 11, 12 of the bracket 10 extend from the plate section 13 at an angle 14 that measures 90 degrees; however, in alternative embodiments, the angle 14 measures between (and including) 85 and 95 degrees.

Figure 40:
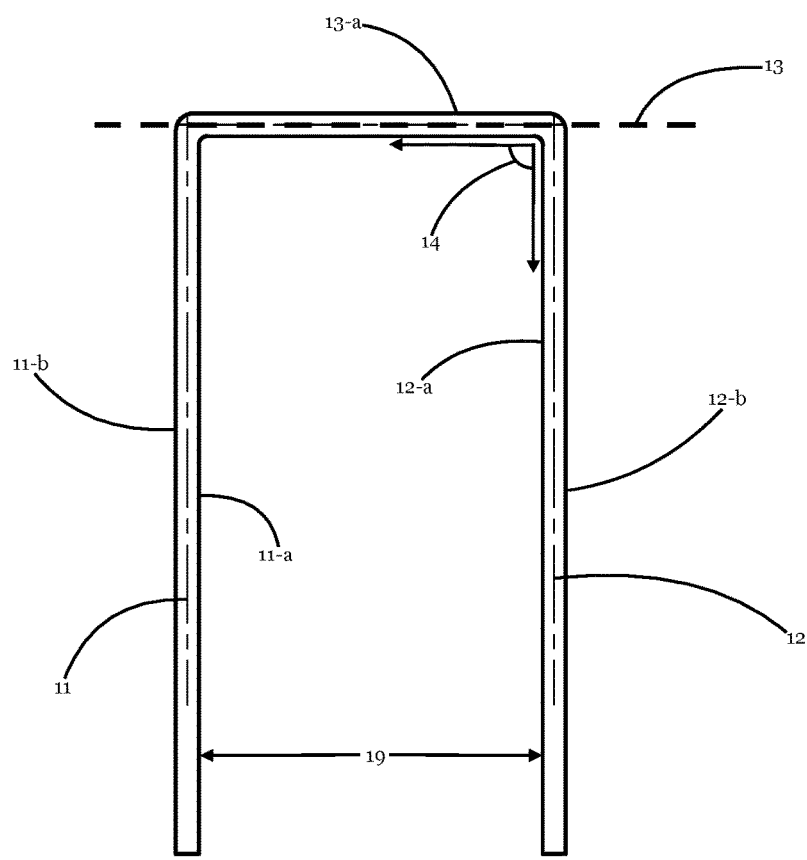
FIG. 40 depicts a perspective view of the bracket included in the extractor.
Figure 41:
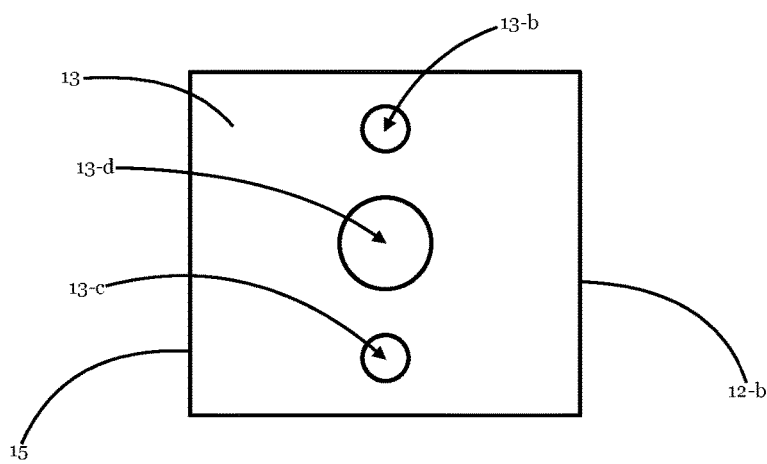
FIG. 41 depicts a perspective view of the bracket included in the extractor.
Figure 42:
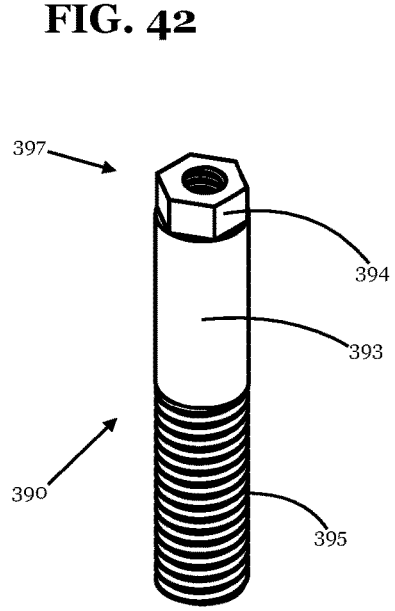
FIG. 42 depicts a perspective view of the shaft included in the extractor.

As FIG. 40 illustrates, the bracket 10 is provided with a "U" shape with the plate section 13 located between the leg sections 11, 12. According to one aspect, the leg sections 11, 12 are dimensioned, at least in part, according to the body 200. According to another aspect, the leg sections 11, 12 are dimensioned to provide clearance for the plate section 13 to rotate about the first end 210 of the body 200.

Each of the leg sections 11, 12 is provided with an inner leg surface and an outer leg surface. Thus, the first leg section 11 is provided with a "first" inner leg surface 11-*a* and a "first" outer leg surface 11-*b* while the second leg section 12 is provided with a "second" inner leg surface 12-*a* and a "second" outer leg surface 12-*b*. (Consistent with the ordinal number convention used herein, the "first" and "second" monikers are used simply to distinguish one surface from another.)

The first and second inner surfaces 11-*a*, 12-*a* extend from the plate section 13 of the bracket 10 generally parallel to each other. Located within the "U" shape of the bracket 10, the first and second inner surface 11-*a*, 12-*a* face one another. In contrast, the first and second outer leg surfaces 11-*b*, 12-*b* are located outside the "U" shape of the bracket 10 and face away from one another.

Each of the leg sections 11, 12 extends from the plate section 13 and terminates at leg ends 15, 16. (As used herein, the term "leg end" is to be understood broadly to include both the extreme end, as well as a portion of the leg section adjacent to the extreme end.) FIGS. 37-41 illustrate an opening defined within each of the leg ends 15, 16. Accordingly, the first leg end 15 is provided with a first leg opening 17 that is circular in shape and dimensioned according to a tightening collar 800. The second leg end 16 is provided with a second leg opening 18 that is out-of-round in shape (preferably hexagonal) and dimensioned to transmit torque between the bracket 10 and the shaft 390.

As the foregoing implies, the second leg opening 18 is shaped according to the shaft 390, which is slidably and rotatably secured within the body 200 of the extractor 100. As FIGS. 42-46 illustrate, the shaft 390 is provided with a shaft axis 391, an out-of-round shaft section 394, and a threaded shaft section 395. Though the foregoing may imply that the shaft 390 is composed of a plurality of sections that are assembled together (and it is within the scope of the present invention that the shaft be fabricated in such a manner), an assembly of discrete shaft sections is not preferred. Rather, it is preferred to manufacture the shaft 390 from round stainless steel rod that has been cut to length, turned to a circular diameter, and then milled and threaded to shape.

Accordingly, the shaft 390 constituting the preferred embodiment includes a cylindrical shaft section 393 that has been turned to a diameter 392 measuring ½ inches. The shaft diameter 392 is dimensioned to provide the shaft 390 and the body 200 with a close fit wherein the shaft 390 rotates and slides axially within the body 200. The cylindrical shaft section 393 and at least a portion of the threaded shaft section 395 are disposed within the body 200 so that the shaft axis 391 extends through the axis 201 of the body 200 in a generally orthogonal orientation. The cylindrical shaft section 393 is located between the out-of-round shaft section 394 and the threaded shaft section 395. Thus, the out-of-round shaft section 394 and the threaded shaft section 395 extend axially from the cylindrical shaft section 393 to extreme the ends 398, 399 of the shaft 390 itself.

Figure 39:
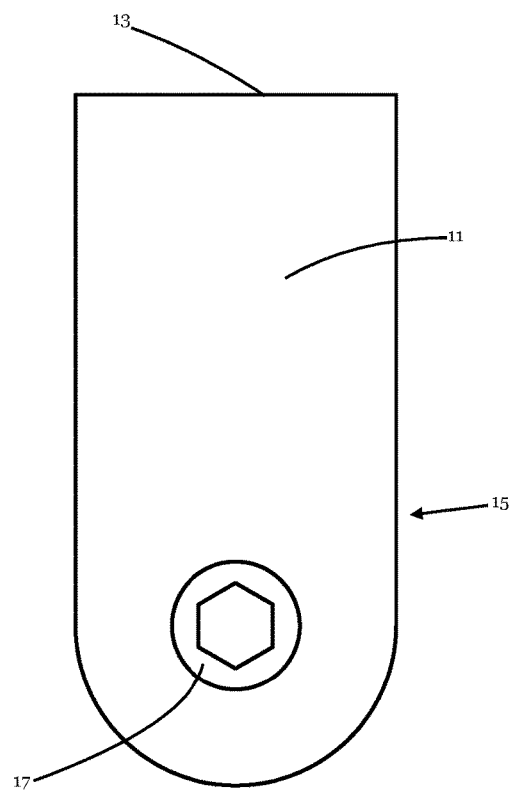
FIG. 39 depicts a perspective view of the bracket included in the extractor.
Figure 43:
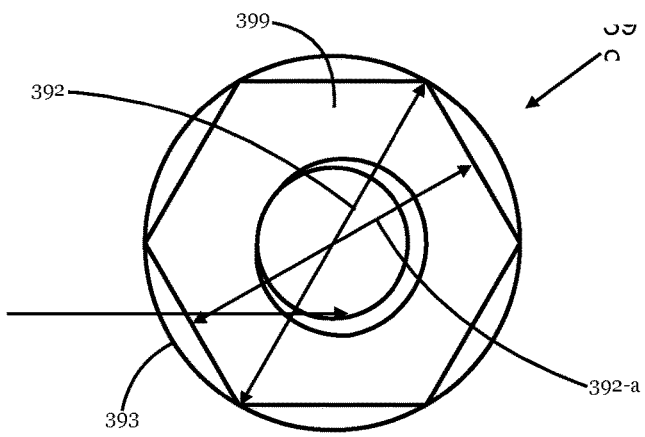
FIG. 43 depicts a perspective view of the shaft included in the extractor.
Figure 45:
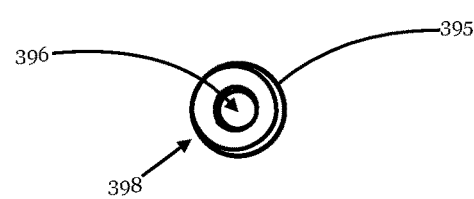
FIG. 45 depicts a perspective view of the shaft included in the extractor.
Figure 44:
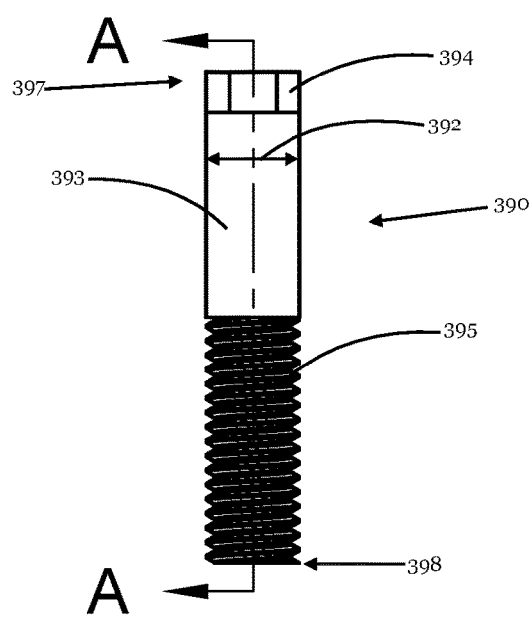
FIG. 44 depicts a perspective view of the shaft included in the extractor.
Figure 46:
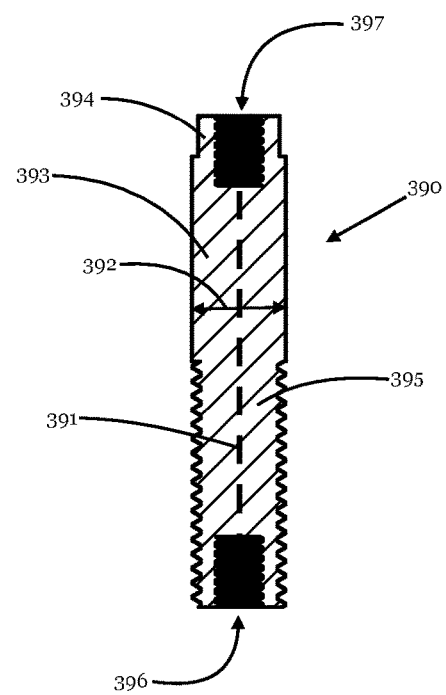
FIG. 46 depicts a cross-sectional view of the shaft depicted in FIG. 44.

As noted above, the out-of-round shaft section 394 extends axially from the cylindrical shaft section 393 and terminates to provide one of the extreme ends 398, 399 to the shaft 390; thus, the extreme end 399 of the shaft 390 is provided with an out-of-round cross-sectional shape, preferably an out-of-round cross-sectional shape that is hexagonal. As is also noted above, the out-of-round shaft section 394 is shaped so that torque applied to the out-of-round shaft section 394 is transmitted to the shaft 390. As FIGS. 43 and 39 illustrate, the out-of-round shaft section 394 is also shaped to fit within the second leg opening 18 so that torque applied to the bracket 10 is transmitted to the shaft 390 (and torque applied to the shaft 390 is transmitted to the bracket 10). As a result, the out-of-round shaft section 394 closely fits within the out-of-round shape of the second leg opening 18.

In contrast to the out-of-round shaft section 394, the threaded shaft section 395 is generally circular in cross-sectional shape, and therefore, the extreme end 398 of the shaft 390 is circular in cross-sectional shape. (To distinguish each of the extreme ends 398, 399 from the other, the extreme end 398 that terminates the threaded shaft section 395 shall also be referred to as the "circular extreme end 398" while the other extreme end 399 that terminates the out-of-round shaft section 394 shall be referred to as the "out-of-round extreme end 399.")

A blind hole is defined within the shaft 390 and extends from an extreme end. In the preferred embodiment, the shaft 390 is provided with a plurality of shaft holes 396, 397 defined within the extreme ends 398, 399. To distinguish each of the shaft holes 396, 397 from the other, the shaft hole 396 extending from the circular extreme end 398 shall be referred to as the "first shaft hole 396" while the other shaft hole 397, which extends from the out-of-round extreme end 399, shall be referred to as the "second shaft hole 397." In the preferred embodiment, the shaft holes 396, 397 extend axially into the shaft 390 in alignment with the shaft axis 391 and are threaded to receive male threaded fasteners. However, in an alternative embodiment, each of the shaft holes 396, 397 is unthreaded to receive a fastening pin.

Figure 37:
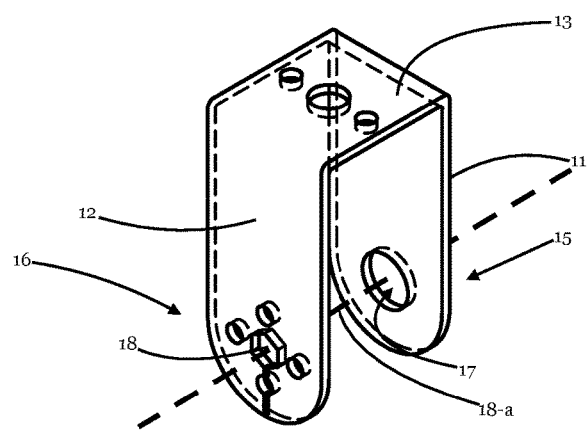
FIG. 37 depicts a perspective view of the bracket included in the extractor.
Figure 38:
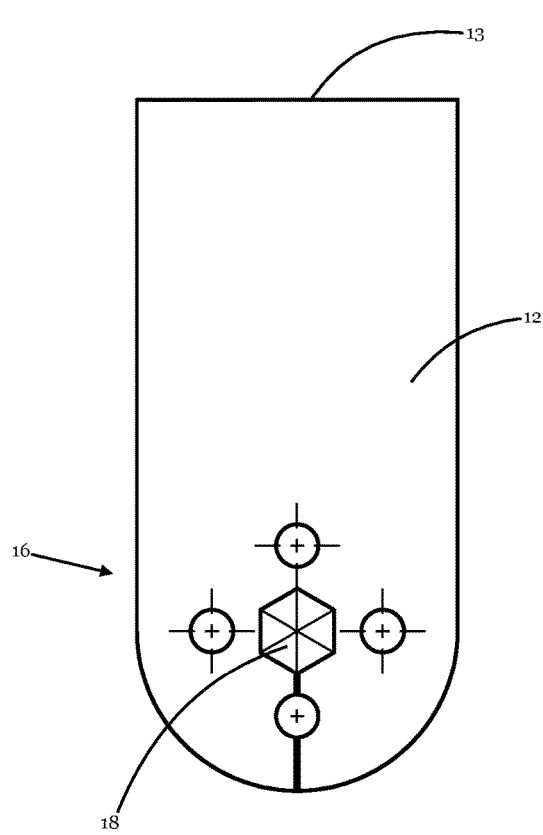
FIG. 38 depicts a perspective view of the bracket included in the extractor.

As noted above, the bracket 10 rotates on the shaft 390 and thus is provided with an axis 18-*a* of rotation (as shown in FIG. 37). The leg openings 17, 18 are defined within the ends 15, 16 of the legs 11, 12 so that they are co-axial with each other and the axis 18-*a* of rotation of the bracket 10 (also shown in FIG. 37). The plate section 13 forms a plane (designated "13-*a*") and is dimensioned so that the leg sections 11, 12 are generally parallel to each other and spaced apart a predetermined distance (referred to herein as a "spacing distance" and designated "19" in FIG. 40). The spacing distance 19 extends linearly along the plane 13-*a* of the plate section 13 in an orientation that is parallel to the axis 391 of the shaft 390. Because the axis 391 of the shaft 390 is oriented to be orthogonal relative to the lever walls 232, 233 of the body 200, the plane 13-*a* of the plate section 13 is also oriented to be orthogonal relative to the lever walls 232, 233 of the body 200. The spacing distance 19 is dimensioned so that the bracket 10 and the shaft 390 move in line with the axis 391 and orthogonally relative to the axis 201 of the body 200.

Figure 47:
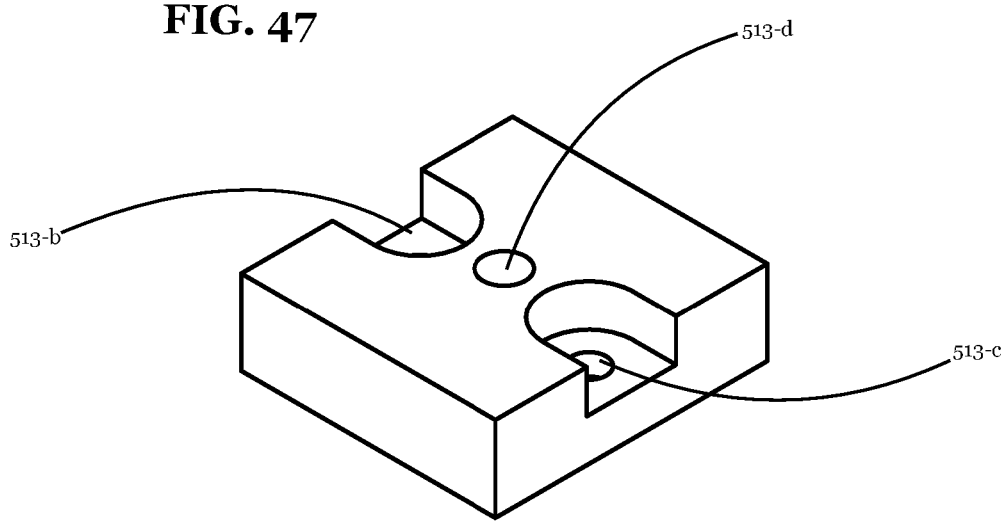
FIG. 47 depicts a perspective view of the strike plate included in the extractor.
Figure 48:
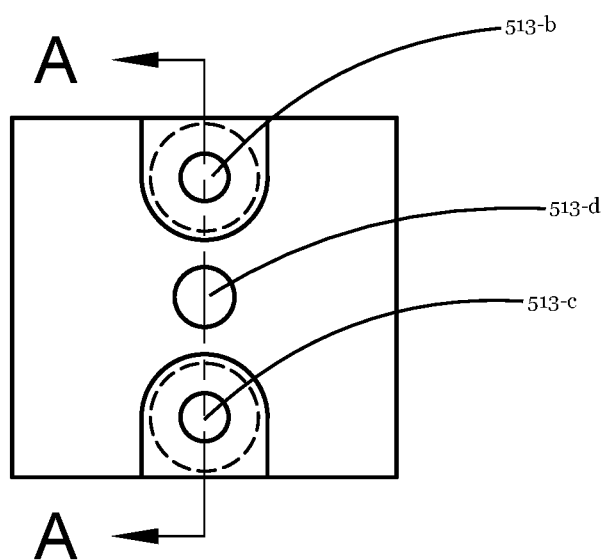
FIG. 48 depicts a perspective view of the strike plate included in the extractor.
Figure 49:
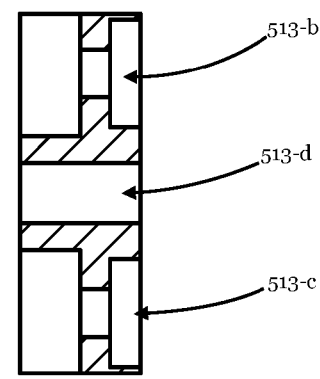
FIG. 49 depicts a cross-sectional view of the strike plate depicted in FIG. 48.

The plate section 13 provides the extractor 100 with a generally flat surface that is configured to receive the blows of a mallet, and therefore the plate section 13 itself provides the extractor 100 with a strike plate; however, it is preferred that the plate section 13 cooperate with an attachment, such as a separate strike plate 500 (shown in FIGS. 47-49). Defined within the plate section 13 is a hole, preferably a plurality of holes 13-*b*, 13-*c*, 13-*d*, configured to cooperate with an attachment. The holes 13-*b*, 13-*c*, 13-*d* are configured to cooperate with a fastener. In FIG. 3, the holes 13-*b*, 13-*c*, 13-*d* are shown cooperating with a fastener; as shown therein, the holes 13-*b*, 13-*c* are shown cooperating with a plurality of threaded fasteners 13-*e*, 13-*f*. The fasteners 13-*e*, 13-*f* are male threaded fasteners, which are secured to the plate section 13 by corresponding female threaded fasteners 13-*g*, 13-*h* (shown in cross-section in FIG. 5) in the form of hex nuts (though in an alternative embodiment, the fasteners 13-*e*, 13-*f* are secured to the plate section by welding). The fasteners 13-*e*, 13-*f* are evenly spaced about a bolt circle and provide the extractor 100 with means for securing an attachment, which in the preferred embodiment is the strike plate 500 depicted in FIGS. 47-49.

Figure 36:
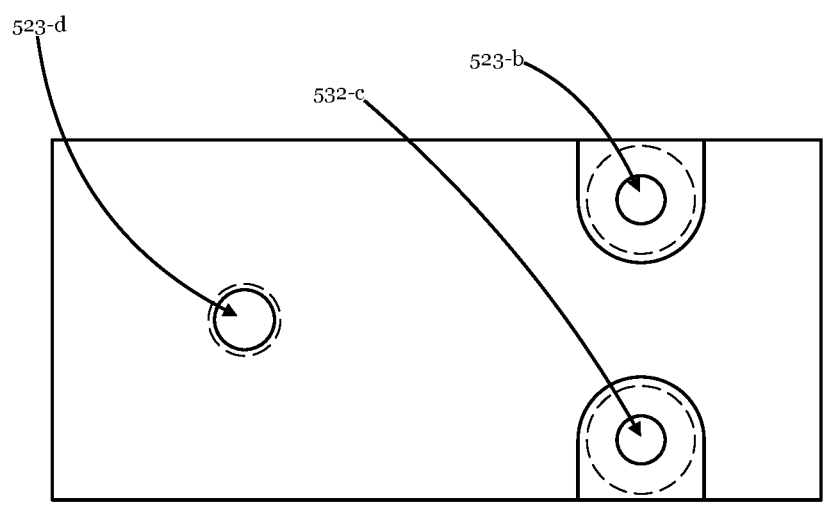
FIG. 36 depicts a perspective view of the strike plate that is offset from the axis of the body.

The bracket 10 is also provided with a hole 13-*d* defined within the center of the plate section 13 (and hence shall be referred to as the "center hole" 13-*d* to distinguish it from other holes 13-*b*, 13-*c* in the plate section 13). The center hole 13-*d* is circular in shape and generally co-axial with the axis 201 of the body 200 when the bracket 10 is locked in place, thereby enabling an appropriately dimensioned male threaded attachment to be passed through the center hole 13-*d* and aligned with the axis 201 of the body. Thus, through the use of a simple nut, a male threaded attachment can be secured to the plate section 13 of the bracket 10. Consequently, the center hole 13-*d* provides the extractor 100 with means for fastening a male threaded attachment with a nut. In the preferred embodiment, the male threaded attachments include a slap hammer (not shown), a Whelan extractor strike plate (not shown) or a strike plate provided with holes 523-*b*, 523-*c* that are co-axial with holes 13-*b*, 13-*c* in the plate section and a third hole 523-*d* that has been offset from the axis 201 of the body 200 (as shown in FIG. 36).

Referring again to FIGS. 47-49, the strike plate 500 is provided with a hole that cooperates with the plate section 13 of the bracket 10. As the figures illustrate, the strike plate 500 is provided with a plurality of holes 513-*b*, 513-*c*, 513-*d* that are positioned to be co-axial with the holes 13-*b*, 13-*c*, 13-*d* defined within the plate section 13 of the bracket 10. As FIGS. 6 and 11 illustrate, the strike plate 500 is provided with a center hole 513-*d* that is threaded and co-axial with the center hole 13-*d* defined within the plate section 13 of the bracket 10. By threading the strike plate 500 onto a male threaded attachment, the strike plate 500 and the attachment can be secured to the plate section 13 of the bracket 10 via nuts and fasteners 13-*e*, 13-*f* passed through the holes 513-*b*, 513-*c* in the strike plate 500 (as FIG. 5 shows).

Figure 52:
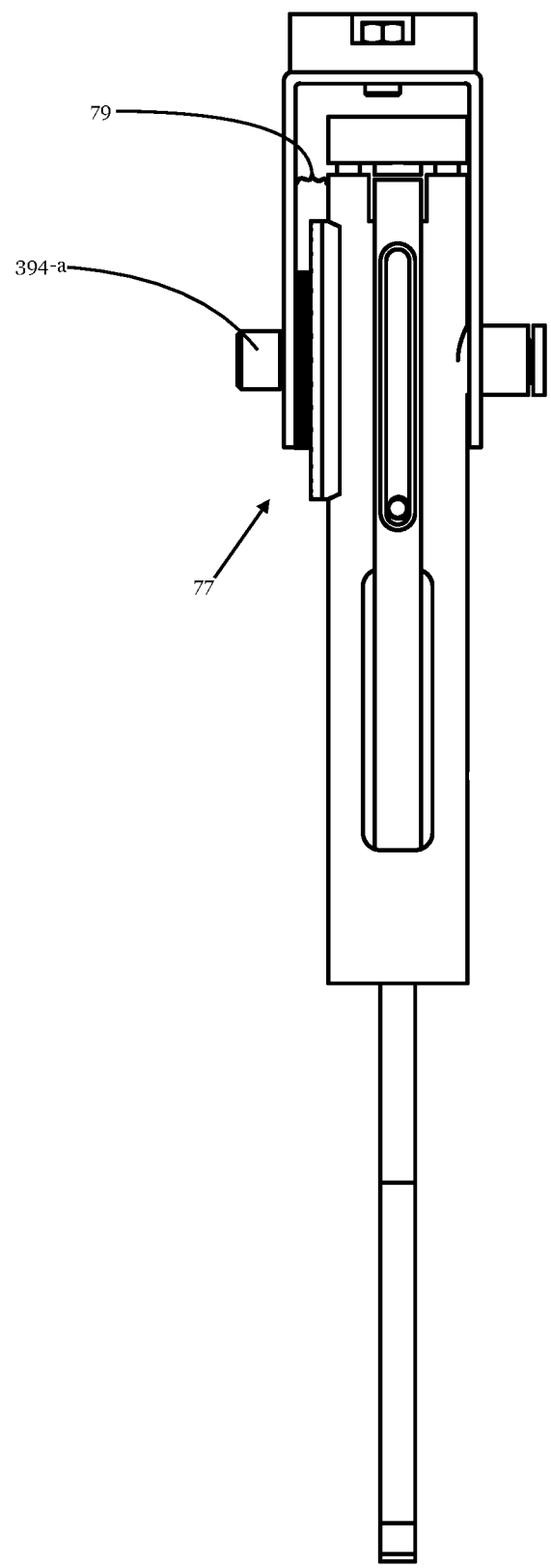
FIG. 52 depicts a perspective view of the extractor with the bracket configured to rotate while the jaws clamp a femoral component.
Figure 55:
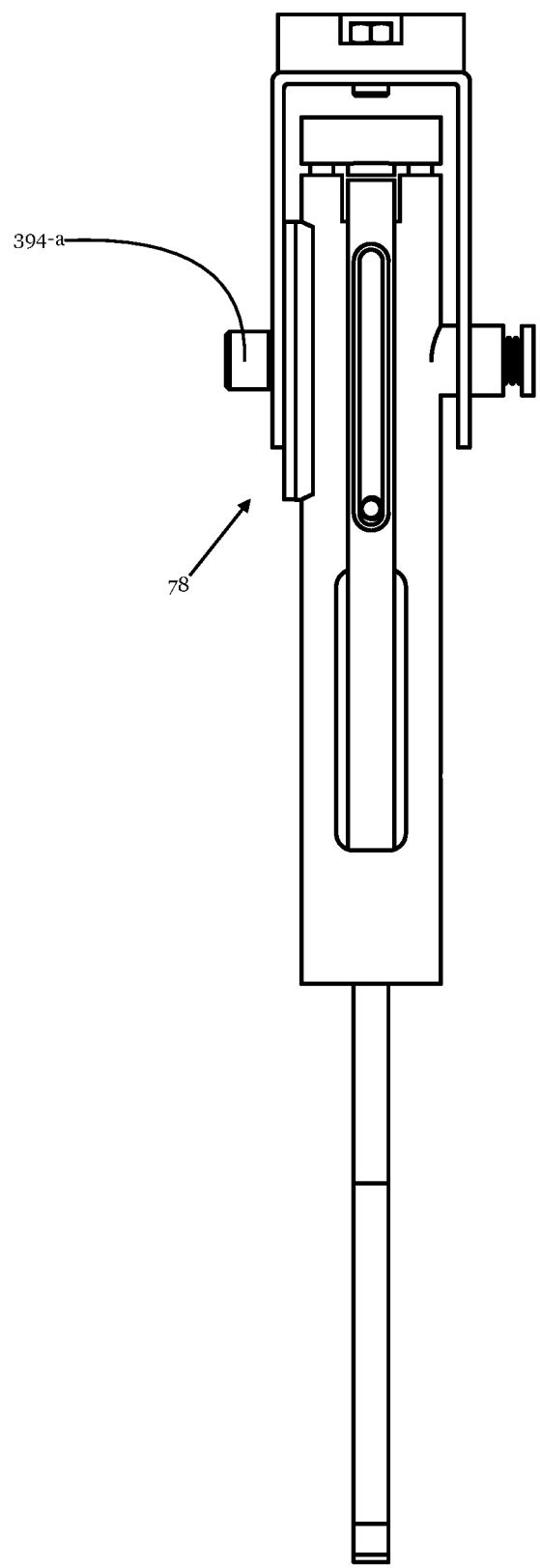
FIG. 55 depicts a perspective view of the extractor with the bracket configured to rotate while the jaws clamp a femoral component.

As noted above, the extractor 100 is provided with an angle selector 70. The angle selector 70 is configured to rotate about the axis 391 of the shaft 390 so that the plane 13-*a* of the plate section 13 of the bracket 10 and the axis 201 of the body 200 form a plurality of angles between each other. In addition to rotating the angle selector 70, the shaft 390 moves the angle selector 70 along its axis 391 between two locations, referred to herein as a "rotating configuration 77" (depicted in FIGS. 50-52) and a "locking configuration 78" (depicted in FIGS. 53-55). In the preferred embodiment, the angle selector 70 is provided with a "locking distance," a dimension designated "79" in FIGS. 51 and 52 that separates the rotating configuration 77 from the locking configuration 78.

Figure 57:
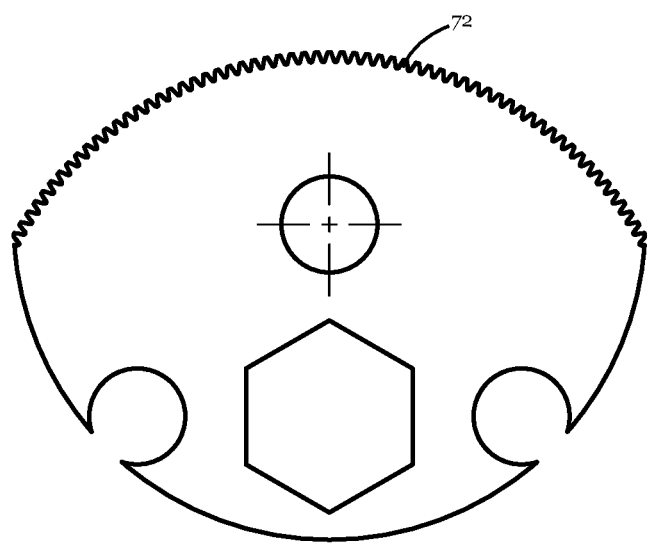
FIG. 57 depicts a detailed view of the gear depicted in FIG. 56.
Figure 58:
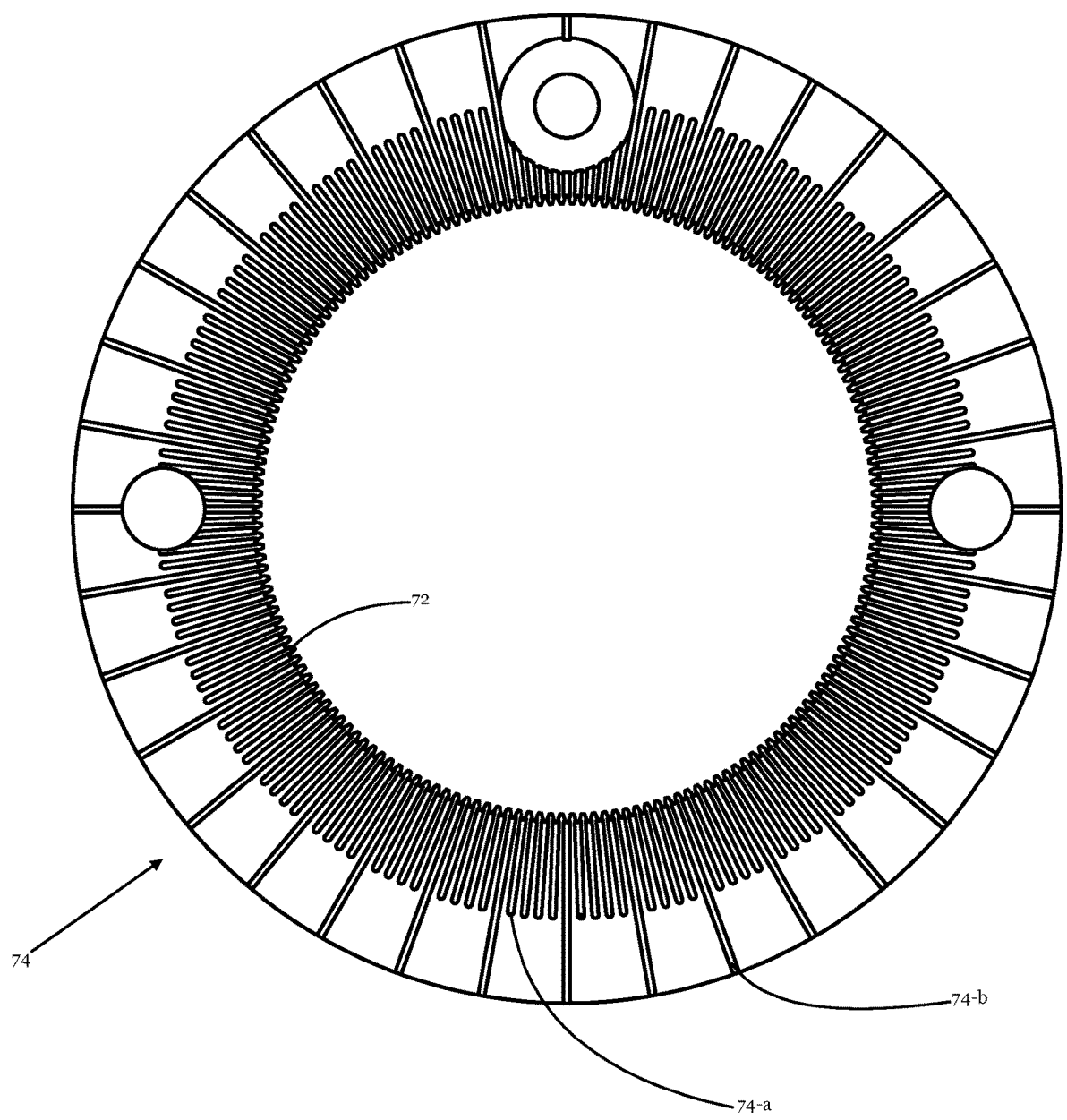
FIG. 58 depicts a perspective view of the gear included with the angle selector, which is itself included with the extractor.
Figure 59:
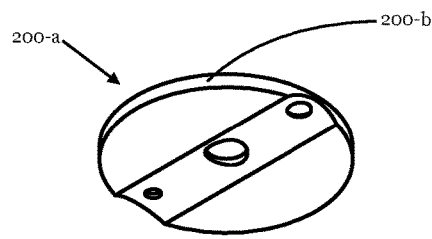
FIG. 59 is a perspective view of the mounting plate included with the extractor.
Figure 61:
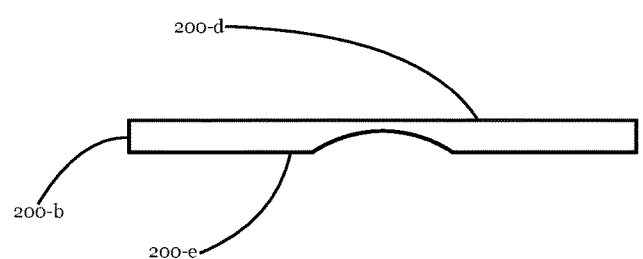
FIG. 61 is a perspective view of the mounting plate included with the extractor.
Figure 62:
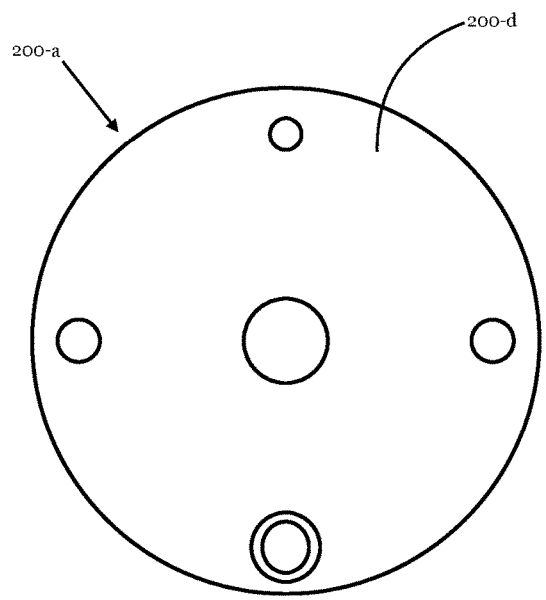
FIG. 62 is a perspective view of the mounting plate included with the extractor.
Figure 60:
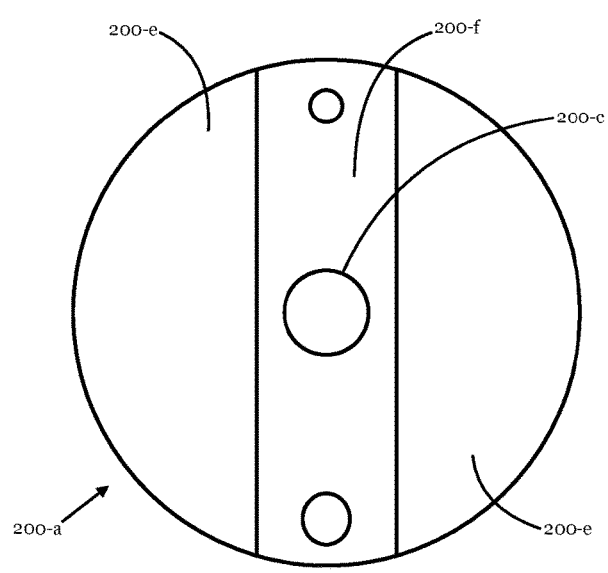
FIG. 60 is a perspective view of the mounting plate included with the extractor.

The angle selector 70 is also provided with a plurality of angle settings 72 that fix the angle between the plane 13-*a* of the plate section 13 of the bracket 10 and the axis 201 of the body 200. In the preferred embodiment, the angle settings 72 are in the form of teeth on interlocking gears 74, 75 (as is shown in FIGS. 57 and 58). However, in an alternative embodiment, the angle settings 72 are in the form of splines on interlocking internal and external splines. In yet another alternative embodiment, the angle settings 72 are in the form of sides on a polygonal shaft that fits within a correspondingly-shaped polygonal opening formed within the body 200.

Returning to the preferred embodiment, however, the angle selector 70 is illustrated in FIG. 11. As shown therein, the angle selector 70 is provided with a first gear 74 and a second gear 75. The first and second gears 74, 75 are provided with teeth that mesh with each other. The first gear 74 is secured to the body 200 while the second gear 75 is secured to the bracket 10. The first gear 74 is in the form of a ring gear that is secured to the body 200 in axial alignment with a hole 202 defined within the body 200 and a tooth in axial alignment with the axis 201 of the body 200. As FIGS. 16 and 17 illustrate, the hole 202 is circular in shape and extends orthogonally through the axis 201 of the body 200.

Figure 56:
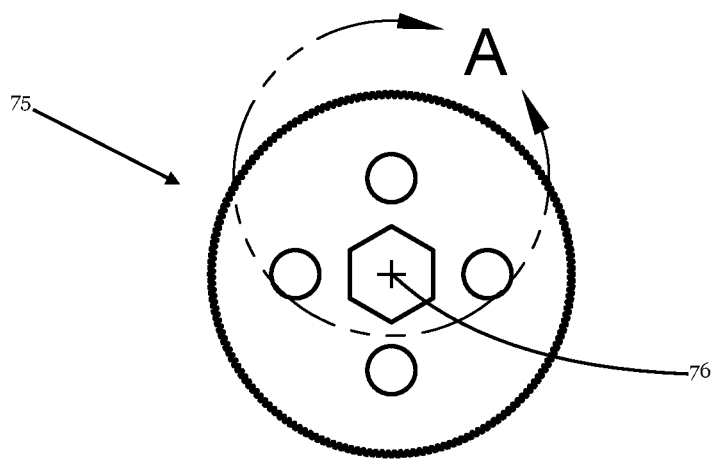
FIG. 56 depicts a perspective view of the gear included with the angle selector, which is itself included with the extractor.

The second gear 75 is in the form of a spur gear that is provided with an axis 76 of rotation. The second gear 75 is attached to the second inner leg surface 12-*b* of the second leg 12 of the bracket 10 so that the axis 76 of the second gear 75 (shown as "+" in FIG. 56) is in alignment with the axis 18-*a* of the second leg opening 18 (for ease of reference, the foregoing attachment of the second gear 75 and the bracket 10 shall be referred to as a "bracket-gear subassembly"). In the preferred embodiment, the second gear 75 is attached to the second inner leg surface 12-*b* via a plurality of stainless steel pins 75-*a*, 75-*b*, 75-*c*, 75-*d*. After the bracket-gear subassembly is completed, the bracket-gear subassembly is assembled onto the out-of-round shaft section 394 of the shaft 390.

In the preferred embodiment, the out-of-round shaft section 394 of the shaft 390 is hexagonal in shape and closely fits within the hexagonal shape of the second leg opening 18 of the bracket 10. The out-of-round shaft section 394 of the shaft 390 and the out-of-round second leg opening 18 are dimensioned so that each is provided with a diameter that is less than the diameter 392 of the cylindrical shaft section 393. As one of ordinary skill in the art will appreciate, the shape of a hexagon is provided with at least two diameters: a diameter extending through the center between opposing sides (as shown in FIG. 43 and designated "392-a") and a diameter extending through the center between opposing vertices (as shown in FIG. 43 and designated "392"). As one of ordinary skill in the art will also appreciate, the diameter between opposing sides of a hexagon is less than the diameter between opposing vertices.

Figure 66:
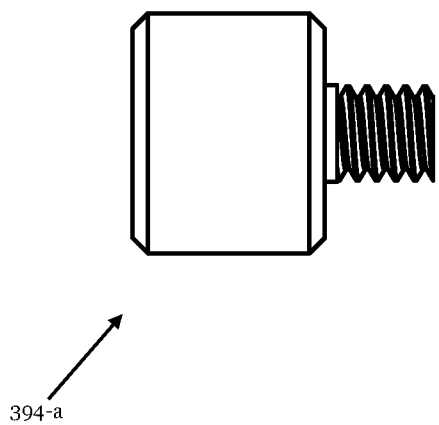
FIG. 66 is a perspective view of the thumb screw included with the extractor.

Because the diameter 392 of the cylindrical shaft section 393 is larger than a diameter 392-a of the out-of-round leg opening 18, the larger diameter 392 of the cylindrical shaft section 393 acts as a stop for the axial positioning of the bracket-gear subassembly on the shaft 390. After the bracket-gear subassembly is positioned onto the out-of-round section 394 of the shaft 390, a thumb screw fastener 394-a (shown in FIG. 66) is torqued into the second shaft hole 397 extending axially into the shaft 390 from the out-of-round extreme end 399 of the shaft 390. Thus, the bracket-gear subassembly is firmly secured to the shaft 390.

The bracket-gear subassembly, the shaft 390, and the body 200 are secured so that the shaft 390 extends through the body 200 and the body 200 is positioned between the inner leg surfaces 11-a, 12-a of the bracket 10. Because the first gear 74 is attached to the body 200 and the body 200 is positioned between the inner leg surfaces 11-a, 12-a, the first gear 74 is also positioned between the inner leg surfaces 11-a, 12-a. With the second gear 75 secured to the second inner leg surface 12-a, the body 200 with the first gear 74 attached thereto is positioned between the inner leg surfaces 11-a, 12-a so that the first gear 74 faces the second gear 75 and the gears 74, 75 are in axial alignment with each other.

With the gears 74, 75 placed in axial alignment, the axis 18-a of the leg openings 17, 18 is aligned with the axis of the circular hole 202 extending through the body 200. After being thus positioned in axial alignment, the shaft 390 is placed through the hole 202 defined within the body 200 and secured to the bracket-gear subassembly. Thus, when the extractor 100 is fully assembled, the gears 74, 75, the shaft 390, and the leg openings 17, 18 defined within the legs 11, 12 of the bracket 10 are all in axial alignment.

As the foregoing indicates, the hole 202 extending through the body 200 is dimensioned at least in part according to the shaft 390. In the preferred embodiment, and as FIG. 17 illustrates, the hole 202 is generally cylindrical in shape and provided with a first cylindrical surface 202-a, a second cylindrical surface 202-b, and a bearing surface 202-c. As FIG. 17 also illustrates, the cylindrical surfaces 202-a, 202-b extend radially around an axis 202-d and are each provided with a diameter (referred to herein as a "hole diameter"). The hole diameter of the first cylindrical surface 202-a (referred to as the "first" hole diameter 202-e) is dimensioned according to the cylindrical shaft section 393 to provide a "close fit" between the first cylindrical surface 202-a and the cylindrical shaft section 393. The term "close fit" is used with respect to the cylindrical shaft section 393 and the hole 202 to refer to diameters of the cylindrical shaft section 393 and the hole 202 being dimensioned so that the axes of the cylindrical shaft section 393 and the hole 202 are maintained in alignment while, at the same time, allowing rotation and axial movement of the cylindrical shaft section 393 linearly within the hole 202.

The extractor 100 is shown in FIGS. 59-62 provided with a mounting plate 200-a. The mounting plate 200-a is attached to the body 200 via a plurality of flat head cap screws 200-d, 200-e and tapped holes 200-f, 200-g. (In an alternative embodiment, however, the mounting plate 200-a is welded to the body 200.) The mounting plate 200-a provides the extractor 100 with a suitable structure upon which to mount at least a portion of the angle selector 70.

In the preferred embodiment, the mounting plate 200-a is shaped to cooperate with the shaft 390. As FIGS. 59-62 illustrate, the mounting plate 200-a is generally in the shape of a disc with a cylindrical surface 200-b defining the outside edge and a circular through-hole 200-c located at the center. The through-hole 200-c is provided with a diameter dimensioned to provide a close fit with the cylindrical shaft section 393 of the shaft 390. Thus, the through-hole 200-c is dimensioned so that the shaft 390 is firmly held therewithin with sufficient clearance that the shaft 390 moves axially and rotates within the through-hole 200-c.

The mounting plate 200-a is provided with a first side 200-d and a second side 200-e. The sides 200-d, 200-e extend radially from the through-hole 200-c to the cylindrical surface 200-b that defines the outer extent of the mounting plate 200-a. To facilitate attaching the mounting plate 200-a to the body 200, the mounting plate 200-a is provided with a cylindrical surface 200-f that extends across the second side 200-e and through the center of the mounting plate 200-a. In the preferred embodiment, the cylindrical surface 200-f is dimensioned according to the body 200 and therefore is cylindrically-shaped with a diameter that matches the diameter 203 of the body 200.

The first side 200-d of the mounting plate 200-a is shaped for the purpose of mounting the first gear 74 thereon. In the preferred embodiment, the mounting plate 200-a is shaped to orient the first gear 74 to be generally orthogonal to the axis 202-d of the hole 202 extending through the body 200. Thus, the first side 200-d of the mounting plate 200-a is substantially flat. The first side 200-d also acts as a stop that prevents the second gear 75 from moving axially beyond the plane of the first gear 74.

Figure 63:
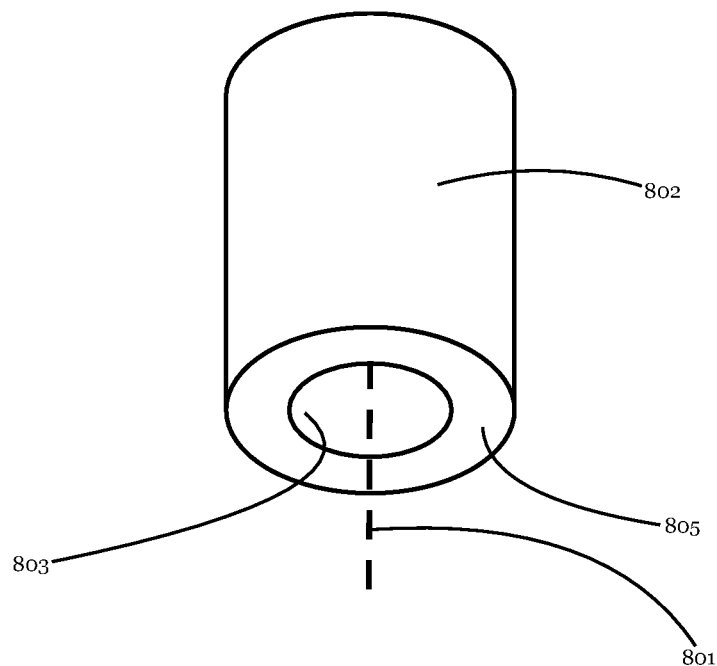
FIG. 63 is a perspective view of the tightening collar included with the extractor.
Figure 64:
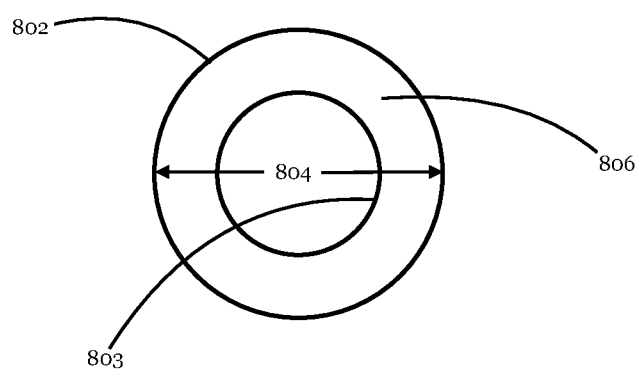
FIG. 64 is a perspective view of the tightening collar included with the extractor.
Figure 65:
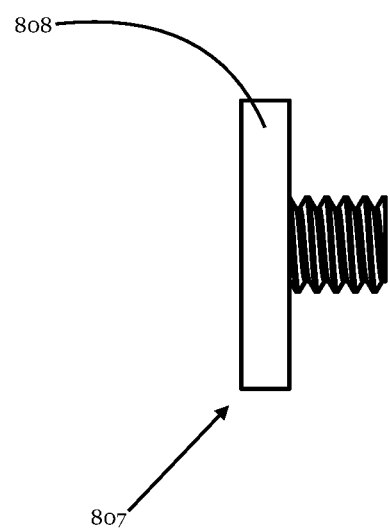
FIG. 65 is a perspective view of the male threaded fastener included with the extractor.

As FIGS. 2, 4, and 6 illustrate, the extractor 100 is provided with a tightening collar 800. As FIGS. 63 and 64 show, the tightening collar 800 includes an outer surface 802, an inner surface 803, and collar bearing surfaces 805, 806 located at the extreme ends of the tightening collar 800. As the foregoing implies, the outer and inner surfaces 802, 803 terminate at the collar bearing surfaces 805, 806, which are annular in shape (but in an alternative embodiment are frusto-conically shaped).

The outer surface 802 is shaped to cooperate with the first leg opening 17 defined within the end 15 of the first leg section 11 of the bracket 10. The outer surface 802 is shaped so that the tightening collar 800 supports the bracket 10 (at least partially) while, at the same time, rotating within the first leg opening 17. In the preferred embodiment, the outer surface 802 of the tightening collar 800 is cylindrical about an axis 801 and provided with a diameter 804. The diameter 804 is dimensioned so that a close fit is achieved between the outer surface 802 of the tightening collar 800 and the first leg opening 17 of the bracket 10; thus, the axes of the tightening collar 800 and the first leg opening 17 are maintained in alignment while at the same time allowing the tightening collar 800 to rotate and move axially within the first leg opening 17. The diameter 804 of the tightening collar 800 is also dimensioned so that a close fit is achieved between the outer surface 802 of the tightening collar 800 and the second cylindrical surface 202-b of the hole 202 extending through the body 200.

The inner surface 803 of the tightening collar 800 is provided with a thread profile that complements the threaded shaft section 395; consequently, the tightening collar 800 moves axially on the shaft 390 as the tightening collar 800 is rotated on the threaded shaft section 395. The tightening collar 800 is retained on the threaded shaft section 395 via the head 808 of a male threaded fastener 807 (shown in FIG.

65); thus, the shaft 390 extends through the tightening collar 800 (and the first leg opening 17 of the bracket 10). As FIG. 11 illustrates, the male threaded fastener 807 is torqued into the first shaft hole 396 with the head 808 extending radially around the threaded shaft section 395 to act as a stop that retains the tightening collar 800 on the shaft 390.

As noted above, the first and second gears 74, 75 are in the form of a ring gear and a spur gear respectively wherein teeth of the first gear 74 (the ring gear) extend radially inward toward the axis of rotation while the teeth of the second gear 75 (the spur gear) extend radially outward away from the axis of rotation. Consequently, the teeth of the first and second gears 74, 75 mesh when the gears 74, 75 are co-planar; thus, the angle settings 72 of the angle selector 70 are fixed. Conversely, the teeth of the first and second gears 74, 75 are disengaged when the gears 74, 75 are spaced axially (and therefore not co-planar); thus, the angle settings 72 are rotable and a predetermined angle can be selected.

The first gear 74 is provided with 180 internal teeth while the second gear 75 is provide with 180 external teeth. Thus, in the preferred embodiment, each tooth is radially positioned about the axis of rotation every 2 degrees, and hence, the teeth of the first and second gears 74, 75 mesh in 2-degree increments.

As is noted above, the first gear 74 is fixed in place on the body 200 while the second gear 75 is attached to the second inner leg surface 12-a of the bracket 10, which is itself attached to the shaft 390. As is also noted above, the shaft 390 is rotably secured within the hole 202 of the body 200. Thus, the teeth of the second gear 75 are rotatable with the shaft 390. As a result, the second gear 75 is free to rotate with the shaft 390 (when the teeth of the second gear 75 are not meshed with the teeth of the first gear 74). However, when the teeth of the second gear 75 are meshed with the teeth of the first gear 74, the first gear 74 prevents the second gear 75 from rotating (because the first gear 74 is fixed in place on the body 200).

As noted above, the teeth of the first and second gears 74, 75 mesh when the first and second gears 74, 75 are co-planar but are disengaged when the first and second gears 74, 75 are spaced axially. Thus, by axially spacing the first and second gears 74, 75, the teeth are disengaged and the second gear 75 can rotate freely with the shaft 390. Conversely, by positioning the first and second gears 74, 75 to be co-planar, the teeth are meshed and the second gear 75 is locked into place thereby preventing rotational motion with the shaft 390.

As the foregoing illustrates, by moving the shaft 390 axially within the hole 202 of the body 200, the second gear 75 (which is attached to the shaft 390) is moved axially relative to the first gear 74, and therefore, the second gear 75 can be positioned to be co-planar with the first gear 74 (and the teeth meshed) or spaced from each other axially (and the teeth not meshed). Thus, by moving the shaft 390 axially within the hole 202, the second gear 75 is positioned to rotate or remain fixed in place, thereby moving the angle selector 70 into the rotating configuration 77 or the locking configuration 78. For ease of reference, the distance between the locking configuration 78 (where the gears 74, 75 are co-planar) and the rotating configuration 77 (where the gears 74, 75 are rotating) shall be referred to as "axial spacing" and designated "79."

As described above, the cylindrical shaft section 393 and the second gear 75 are axially aligned with the leg openings 17, 18 and secured between the leg sections 11, 12 of the bracket 10. As is also described above, the plate section 13 provides a spacing distance 19 between the leg sections 11, 12 of the bracket 10. The spacing distance 19 between the leg sections 11, 12 is dimensioned so that the bracket 10 moves the angle selector 70 axially between the rotating configuration 77 and the locking configuration 78, and hence, the spacing distance 19 between the leg sections 11, 12 is dimensioned to provide the extractor with axial spacing 79. In the preferred embodiment, first gear 74 and the second gear 75 are separated by axial spacing 79 that is at least the width of the first gear 74 (which measures ⅛ inches); however, in alternative embodiments, the first gear 74 is provided with a greater width, such as 10 mm.

By separating the second gear 75 axially from the first gear 74 by axial spacing 79, the bracket 10, and hence the plate section 13, is free to rotate about the first end 210 of the body 200. Thus, the plate section 13 is free to form an angle with respect to the axis 201 of the body 200. Then, by removing the axial spacing 79 separating the second gear 75 from the first gear 74, the gears 74, 75 are co-planar and the teeth of the second gear 75 are meshed with the teeth of the first gear 74. Because the first gear 74 is fixed in place on the body 200 and because the teeth of the second gear 75 (which is attached to the bracket 10) are meshed with the teeth of the first gear 74, the bracket 10 is fixed in place with the body 200 and cannot rotate about the first end 210 of the body 200. Because the bracket 10 cannot rotate about the first end 210 of the body 200, the plate section 13 of the bracket 10 cannot rotate either, and, as a result, the angle with respect to the axis 201 of the body 200 is fixed.

In the preferred embodiment, the second gear 75 is axially separated from the first gear 74 by simply pulling the second leg section 12 of the bracket 10 away from the body 200. Because the first gear 74 is fixed in place on the body 200 and because the second gear 75 is attached to the second leg section 12 of the bracket 10, the action of pulling the second leg section 12 away from the body 200 has the effect of axially separating the second gear 75 from the first gear 74 thereby placing the extractor 100 into the rotating configuration 77.

Conversely, the axial spacing 79 between the gears 74, 75 is removed when the second leg section 12 of the bracket 10 is pushed toward the body 200. As noted above, because the first gear 74 is fixed to the body 200 while the second gear 75 attached to the second leg section 12 of the bracket 10, the action of pushing the second leg section 12 toward the body 200 has the effect of pushing the second gear 75 into being co-planar with the first gear 74 so that the gears 74, 75 mesh, thereby placing the extractor 100 into the locking configuration 78.

As FIGS. 50 and 53 illustrate, the second outer leg surface 12-b of the second leg section 12 of the bracket 10 is provided with an indicator 12-c. In the preferred embodiment, the indicator 12-c is pressed into the second outer leg surface 12-b; however, in an alternative embodiment, the indicator 12-c is engraved into the second outer leg surface 12-b. The indicator 12-c extends in an orthogonal orientation relative to the plane 13-a of the plate section 13 of the bracket 10, and the second gear 75 is mounted to the second inner leg surface 12-a so a tooth is aligned with the indicator 12-c.

As FIG. 58 illustrates, the first gear 74 is provided with a plurality of marks 74-a, 74-b, which extend radially from the teeth of the first gear 74. The preferred embodiment is provided with two sets of marks 74-a, 74-b, a first set of marks 74-a wherein each of the marks 74-a is aligned with each tooth on the first gear 74 and a second set of a marks 75-b wherein each of the marks is aligned with every fifth tooth on the first gear 74. Because each of the gears 74, 75 has a tooth every two degrees around the circumference and because the first set of marks 74-*a* is aligned with each tooth, the first set of marks 74-*a* delineates two degrees of rotation while the second set of marks 74-*b* delineates ten degrees of rotation. Thus, in the preferred embodiment, the angle settings 72 provide over 145 predetermined angles between the axis 201 of the body 200 and the plane 13-*a* of the plate section 13 of the bracket 10 to be selected and fixed in place in the locking configuration.

To maintain a desirable angle in a locked position, the tightening collar 800 on the threaded shaft section 395 is torqued so that the tightening collar 800 moves axially from the extreme end 398 of the shaft to a position where the tightening collar 800 bears against the bearing surface 202-*c* of the body 200. As the tightening collar 800 is being torqued, one of the tightening collar bearing surfaces 805, 806 bears against the bearing surface 202-*c* within the body 200. As the tightening collar 800 is torqued into the bearing surface 202-*c* of the body 200, the second gear 75 is clamped in place with its teeth meshed with the teeth of the first gear 74; thus, the shaft 390 is prevented from moving axially within the first cylindrical surface 202-*a* defined within the body 200. With axial motion thus prevented, axial spacing 79 cannot be created between the gears 74, 75 unless the tightening collar 800 is loosened. Thus, the extractor 100 is secured in the locking configuration 78 and cannot slip into the rotating configuration 77.

In sum, by pulling the second leg section 12 of the bracket 10 away from the body 200, the extractor 100 is placed into the rotating configuration 77 and the angle between the plate section 13 of the bracket 10 and the axis 201 of the body 200 can be changed. As the indicator 12-*c* on the second leg section 12 of the bracket rotates past each of the marks 74-*a*, 74-*b* on the first gear 74, the angle between the plate section 13 of the bracket 10 and the axis 201 of the body 200 and the plate section 13 of the bracket 10 is changed by two degrees. By aligning the indicator 12-*c* with one of the marks 74-*a*, 74-*b* on the second gear 75 and by pushing the second leg section 12 of the bracket 10 toward the body 200, a desirable angle between the plate section 13 and the axis of the body 200 can be selected and locked into place by torqueing the tightening collar 800 on the shaft 390 onto the bearing surface 202-*c* of the body 200.

As described above, when the upper wedging surfaces 216, 218 of the body 200 are positioned under the trunnion 1102 and bear against the bottom surface 1104, the axis 201 of the body 200 is generally parallel to the axis 1101 of the trunnion 1102. As a result, when the plate section 13 of the bracket 10 is oriented at an angle relative to the axis 201 of the body 200, the plate section 13 is also oriented at the same general angle relative to the axis 1101 of the trunnion 1102.

Because surgeons practicing joint replacement are quite familiar with the angle 1411 between the trunnion axis 1101 and the impacting axis 1401 and the angle 1211 between the trunnion axis 1101 and the stem axis 1201 of a given femoral component, the indicator 12-*c* also shows the angle between the plate section 13 and the impacting axis 1401 of the femoral component 1000 and the angle between the plate section 13 and the stem axis 1201 of the femoral component 1000.

Consequently, the plate section 13 (and the strike plate 500 attached thereto) can be oriented so that, when the plate is impacted, the direction of the impulse transmitted to the femoral component 1000 can be controlled. Thus, the plate section 13 and the strike plate 500 can be oriented so that an impact is transmitted to the femoral component 1000 in a direction that is advantageous to extracting the femoral component 1000 from the patient's femur.

By way of example and not limitation, it may be desirable to orient the plate section 13 and the strike plate 500 to be orthogonal to the impacting axis 1401 so that when the strike plate 500 is impacted, the impulse delivered to the femoral component 1000 is in a direction out of the femur. Those with skill in the art will appreciate that the plate section 13 can be rotated into a plurality of orientations so that the femoral component 1000 is impacted at different angles that are advantageous to breaking the bonds of osseointegration and/or cement that fix the femoral component within a patient's femur.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An extractor with a first end and a second end configured to extract a femoral component with a neck and a trunnion that includes a top trunnion surface and a bottom trunnion surface, comprising,
    a) a body provided with an axis, an outer body surface, a first body end that includes a first body end surface, and a second body end that includes a second body end surface, wherein the body extends axially and terminates at each of the body end surfaces and each of the body end surfaces terminates at the outer body surface wherein:
        i) a wedging structure located at the second end of the body provided with a first wedging surface, a second wedging surface, a first upper wedging surface, and a second upper wedging surface wherein:
            (1) the first and second wedging surfaces are configured to wedge the second end of the body at least partially around the neck of the femoral component;
            (2) the upper wedging surfaces are configured to be placed into contact with the bottom trunnnion surface;
            (3) the first wedging surface and the second wedging surface form an angle between each other measuring less than 40 degrees;
        ii) a lever opening that includes a first lever wall, a second lever wall, and a lever ceiling, wherein, the lever walls oppose one another and the lever ceiling extends from the first lever wall to the second lever wall;
        iii) a first fulcrum hole defined within the body and located to extend in a generally orthogonal orientation through the first and second lever walls so as to provide the extractor with a first force section that generally extends from the first fulcrum hole toward the first end of the body and a first resistance section that generally extends from the first fulcrum hole toward the second end of the body;
        iv) a threaded surface located within the first force section that cooperates with a threaded fastener;
    b) a lever provided with a first lever end, a second lever end, and a second fulcrum hole wherein:
        i) the lever extends through the lever opening defined within the body at an angle relative to the axis of the body;
        ii) the second fulcrum hole is defined within the lever and located to provide the extractor with a second force section that generally extends from the second fulcrum hole towards the first end of the lever and a second resistance section that generally extends from the second fulcrum hole towards the second end of the lever;
c) a fulcrum comprising a stainless steel pin extending through the first fulcrum hole defined within the body and the second fulcrum hole defined within the lever;
d) a clamping arrangement that includes opposing clamping sections located within the first and second resistance sections, which generally extend towards the second end of the extractor, wherein the threaded surface located within the first force section, which generally extends towards the first end of the extractor, cooperates with the threaded fastener to draw together the opposing clamping sections; and
e) a strike plate configured to receive an impact.

2. The extractor according to claim 1 wherein the lever further includes a locking surface that cooperates with the threaded surface of the body by locking in place the lever when the threaded fastener and the threaded surface of the body are tightened together.

3. The extractor according to claim 1 wherein the first and second wedging surfaces are spaced from each other a distance that ranges between 0.2 and 0.75 inches.

4. The extractor according to claim 1 further comprising a trunnion accepting structure extending from the wedging structure that is provided with a first trunnion accepting wall and a second trunnion accepting wall, wherein:
a) the first and second trunnion accepting walls extend axially from the upper wedging surfaces; and
b) the first and second trunnion accepting walls are spaced from each other at least 14 mm.

5. The extractor according to claim 1 wherein the first wedging surface and the second wedging surface form an angle measuring 20 degrees.

6. The extractor according to claim 1 further comprising a locking component provided with:
a) a first outer surface and a second outer surface:
   i) the first outer surface is provided with a through-hole and a bearing surface for the threaded fastener;
   ii) the second outer surface is provided with a locking ridge formed where a plurality of ramps abut one another; and
b) the locking ridge is configured to lock in place the lever when the threaded fastener and the threaded surface of the body are torqued together.

7. The extractor according to claim 1 further comprising a shaft, a bracket, and an angle selector wherein:
a) the shaft is provided with a shaft axis, a cylindrical shaft section, and a threaded shaft section wherein:
   i) the cylindrical shaft section extends at least partially through the body so that the shaft rotates and slides axially within the body; and
   ii) the threaded shaft section extends at least partially through a tightening collar and the first leg opening;
b) the bracket is configured to rotate on the shaft and is provided with a first leg section and a second leg section that extend from a plate section;
   i) the first leg section includes a first leg opening that is shaped to accommodate the tightening collar;
   ii) the second leg opening accommodates, at least partially, an end of the shaft;
   iii) the plate section extends along a plane that is generally parallel to the shaft axis;
c) the angle selector is provided with a rotating configuration, a locking configuration, and a plurality of angle settings wherein:
   i) the plane of the plate section of the bracket is fixed relative to the axis of the body in the locking configuration;
   ii) the plane of the plate section of the bracket rotates freely about the first end of the body in the rotating configuration; and
   iii) the angle settings provide a plurality of predetermined angles between the axis of the body and the plane of the plate section of the bracket to be selected and fixed in place in the locking configuration.

8. An extractor that is configured to extract a femoral component with a neck and a trunnion, comprising:
a) a first extractor end and a second extractor end wherein the first end is provided with a strike plate that includes a plane and that is rotatably connected to the extractor and the second end is configured to clamp the neck of the femoral component;
b) a body provided with an outer body surface that encloses an axis, a first end that includes a first end surface, and a second end that includes a second end surface, wherein:
   i) the body extends axially and terminates at each of the end surfaces;
   ii) each of the end surfaces terminates at the outer body surface;
   iii) a lever opening defined within the body that includes a first lever wall, a second lever wall, and a lever ceiling, wherein, the lever walls oppose one another and the lever ceiling extends from the first lever wall to the second lever wall;
   iv) a first fulcrum hole defined within the body and extending in a generally orthogonal orientation through the lever walls and located to provide the extractor with a first force section that generally extends from the first fulcrum hole towards the first end of the body and a first resistance section that generally extends from the first fulcrum hole towards the second end of the body;
c) a lever extending through the lever opening at an angle relative to the axis of the body wherein:
   i) the lever includes a first lever end and a second lever end;
   ii) a second fulcrum hole defined within the lever and located to provide the extractor with a second force section that generally extends from the second fulcrum hole towards the first end of the lever and a second resistance section that generally extends from the second fulcrum hole towards the second end of the lever;
d) a fulcrum comprising a stainless steel pin extending through the first fulcrum hole defined within the body and the second fulcrum hole defined within the lever;
e) a clamping arrangement that includes the first and second resistance sections that generally extend towards the second end of the extractor and the first and second force sections that generally extend towards the first end of the extractor, wherein the first and second resistance sections are drawn together to clamp the femoral component; and
f) an angle selector provided with a rotating configuration, a locking configuration, and a plurality of angle settings wherein:
   i) the plane of the strike plate rotates freely in the rotating configuration to form a plurality of angles between the plane of the strike plate and the axis of the body;

ii) the plane of the strike plate is fixed in the locking configuration to form a single angle between the plane of the strike plate and the axis of the body; and iii) the angle settings provide a plurality of selectable angles between the plane of the strike plate and the axis of the body are fixed in place in the locking configuration.

9. The extractor according to claim 8, wherein the angle settings are in the form of teeth on interlocking gears wherein:

a) the interlocking gears include a first gear and a second gear which are in axial alignment;

b) the first gear includes an axis of rotation and a plurality of teeth that extend radially inward toward the axis of rotation;

c) the second gear includes a plurality of teeth that extend radially outward;

d) the teeth of the first gear and the teeth of the second gear mesh in the locking configuration; and e) an axial spacing separates the teeth of the first gear and the teeth of the second in the rotating configuration.

10. The extractor according to claim 9, further comprising a shaft that includes a shaft axis wherein:

a) the first and second gears are in axial alignment with the shaft;

b) the first gear is fixed to the body while the second gear is fixed to the shaft; and c) the shaft is rotatably mounted within the body.

11. The extractor according to claim 10, further comprising a bracket wherein:

a) the bracket is provided with a first leg section and a second leg section that extend from a plate section, which extends along a plane that is generally parallel to the shaft axis and provides the extractor with a strike plate; and b) the shaft is fixed to at least one of the leg sections of the bracket.

12. The extractor according to claim 11, further comprising a tightening collar wherein:

a) the shaft is provided with a threaded shaft section;

b) the first leg section of the bracket includes a leg opening;

c) the tightening collar is threaded onto the threaded shaft section and extends at least partially through the leg opening of the first leg section of the bracket whereby:

i) the extractor is secured in the locking configuration when the tightening collar is tightened, and ii) the extractor is placed into the rotating configuration when the tightening collar is loosened.

13. An extractor according to claim 8, further comprising a wedging arrangement located at the second end of the body provided with a first wedging surface, a second wedging surface, a first upper wedging surface, and a second upper wedging surface wherein:

a) the first and second wedging surfaces are configured to wedge the second end of the body at least partially around the neck of the femoral component;

b) the upper wedging surfaces are configured to be placed into contact with the bottom trunnnion surface; and c) the first wedging surface and the second wedging surface form an angle between each other measuring less than 40 degrees.

14. The extractor according to claim 8 wherein the clamping arrangement further includes a threaded surface located within at least one of the force sections of the extractor that cooperates with a threaded fastener to draw together the first and second force sections.

15. An extractor that is configured to clamp and extract a femoral component with a neck and a trunnion, comprising, a) a body provided with an axis, an outer body surface, a first end that includes a first end surface, and a second end that includes a second end surface, wherein the body extends axially and terminates at each of the end surfaces and each of the end surfaces terminates at the outer body surface:

i) a lever opening that includes a first lever wall, and a second lever wall, wherein, the lever walls oppose one another;

ii) a first fulcrum hole defined within the body and located to extend in a generally orthogonal orientation through the first and second lever walls so as to provide the extractor with a first force section that generally extends from the first fulcrum hole towards the first end of the body and a first resistance section that generally extends from the first fulcrum hole towards the second end of the body;

iii) the first force section includes a threaded surface that cooperates with a threaded fastener;

b) a lever extending through the lever opening defined within the body at an angle relative to the axis of the body wherein, i) the lever includes a first end, and a second end;

ii) a second fulcrum hole defined within the lever and located to provide the extractor with a second force section that generally extends from the second fulcrum hole towards the first end of the lever and a second resistance section that generally extends from the second fulcrum hole towards the second end of the lever;

iii) the clamping surface is located in the second resistance section;

c) a fulcrum comprising a stainless steel pin extending through the first fulcrum hole defined within the body and the second fulcrum hole defined within the lever;

d) the threaded surface of the first force section and the locking surface of the second force section are configured to be drawn together, at least in part, by a threaded fastener;

e) a clamping arrangement wherein:

i) the fulcrum is located between the force sections and the resistance sections of the extractor;

ii) the resistance sections of the extractor form opposing clamping sections wherein at least one of the opposing clamping sections includes a tooth; and iii) the threaded fastener at least in part exerts a clamping force at the resistance sections of the extractor; and f) a strike plate configured to receive an impact.

16. The extractor according to claim 15 wherein the threaded surface is a nut.

17. The extractor according to claim 15 wherein the threaded surface is a male threaded stud.

18. The extractor according to claim 15 wherein the threaded surface is defined within the body.

19. The extractor according to claim 15 wherein the threaded surface is a first threaded surface defined within the body and generally extending orthogonally relative to the axis of the body and the extractor further includes a second threaded surface defined within the body and extending from the first end surface of the body.

20. The extractor according to claim 19 wherein the second threaded surface defined within the body extends from the first end surface of the body in an orientation that is generally parallel relative to the axis of the body and the extractor further includes a locking component provided with:
- a) an outer surface that includes a through-hole and a bearing surface for a male threaded fastener that is configured to cooperate with the second threaded surface; and
- b) a locking ridge that is configured to lock in place the lever after the male threaded fastener and the second threaded surface of the body have been torqued together.

21. The extractor according to claim 17 wherein the male threaded stud includes a spherically-shaped surface.

22. An extractor that is configured to extract a femoral component with a neck and a trunnion, comprising:
- a) a first extractor end and a second extractor end wherein the first extractor end is provided with a strike plate and the second extractor end is configured to clamp the neck of the femoral component;
- b) a body provided with an outer body surface that encloses an axis, a first body end that includes a first body end surface, and a second body end that includes a second body end surface, wherein:
  - i) the body extends axially and terminates at each of the body end surfaces;
  - ii) each of the body end surfaces terminates at the outer body surface;
  - iii) a lever opening defined within the body that includes a first lever wall and a second lever wall wherein the lever walls oppose one another;
  - iv) a first fulcrum hole defined within the first and second lever walls of the body wherein: (1) the first fulcrum hole extends through the first and second lever wall in a generally orthogonal orientation relative to the body axis, and (2) the first fulcrum hole is located to provide the extractor with a first force section that generally extends from the first fulcrum hole towards the first end of the body and a first resistance section that generally extends from the first fulcrum hole towards the second end of the body;
- c) a lever extending through the lever opening at an angle relative to the axis of the body wherein:
  - i) the lever is provided with a first lever end and a second lever end;
  - ii) a second fulcrum hole is defined within the lever between the first lever end and the second lever end;
  - iii) the second fulcrum hole is located so that the extractor is provided with a second force section that generally extends from the second fulcrum hole towards the first end of the lever and a second resistance section that generally extends from the second fulcrum hole towards the second end of the lever;
- d) a fulcrum comprising a pin extending through the first fulcrum hole defined within the body and the second fulcrum hole defined within the lever;
- e) a male threaded fastener that torques into a threaded surface defined within the extractor wherein the male threaded fastener includes a spherically shaped bearing surface;
- f) a clamping arrangement that includes the first and second force sections, which generally extend from the fulcrum towards the first end of the extractor and the first and second resistance sections, which generally extend from the fulcrum towards the second end of the extractor, wherein the threaded surface of the extractor cooperates with the male threaded fastener to draw together the first and second resistance sections; and
- g) the strike plate is configured to receive an impact.

23. The extractor according to claim 22 wherein the second resistance section of the extractor further includes a lever clamping section that is provided with a tooth.

24. The extractor according to claim 22 wherein the lever further includes a lever angled section that defines the fulcrum hole.

25. The extractor according to claim 22 wherein the second force section of extractor further includes a locking section that cooperates with the threaded surface of the extractor by locking the extractor onto the femoral component when the male threaded fastener and the threaded surface of the extractor are tightened together.

* * * * *